US008883737B2

(12) United States Patent
Reddy et al.

(10) Patent No.: US 8,883,737 B2
(45) Date of Patent: Nov. 11, 2014

(54) METHODS OF TREATING CANCER

(75) Inventors: Joseph Anand Reddy, West Lafayette, IN (US); Christopher Paul Leamon, West Lafayette, IN (US)

(73) Assignee: Endocyte, Inc., West Lafayette (IN)

( * ) Notice: Subject to any disclaimer, the term of this patent is extended or adjusted under 35 U.S.C. 154(b) by 0 days.

(21) Appl. No.: 13/884,842

(22) PCT Filed: Nov. 11, 2011

(86) PCT No.: PCT/US2011/060407
§ 371 (c)(1), (2), (4) Date: Aug. 20, 2013

(87) PCT Pub. No.: WO2012/065085
PCT Pub. Date: May 18, 2012

(65) Prior Publication Data

US 2013/0330326 A1 Dec. 12, 2013

Related U.S. Application Data

(60) Provisional application No. 61/413,275, filed on Nov. 12, 2010.

(51) Int. Cl.

| | |
|---|---|
| *A61K 38/00* | (2006.01) |
| *A61K 39/00* | (2006.01) |
| *A61K 33/24* | (2006.01) |
| *A61K 31/7068* | (2006.01) |
| *A61K 31/337* | (2006.01) |
| *A61K 31/4745* | (2006.01) |
| *A61K 31/704* | (2006.01) |
| *A61K 39/395* | (2006.01) |
| *A61K 38/08* | (2006.01) |
| *A61K 45/06* | (2006.01) |
| *A61K 31/517* | (2006.01) |
| *A61K 31/282* | (2006.01) |
| *A61K 31/519* | (2006.01) |

(52) U.S. Cl.
CPC ............. *A61K 38/08* (2013.01); *A61K 31/7068* (2013.01); *A61K 31/337* (2013.01); *A61K 31/4745* (2013.01); *A61K 33/24* (2013.01); *A61K 31/704* (2013.01); *A61K 39/3955* (2013.01); *A61K 45/06* (2013.01); *A61K 31/517* (2013.01); *A61K 31/282* (2013.01); *A61K 31/519* (2013.01)
USPC ........................ 514/19.3; 424/133.1; 424/649

(58) Field of Classification Search
CPC .. A61K 38/00; A61K 2039/505; A61K 33/24
USPC .............................. 514/19.3; 424/133.1, 649
See application file for complete search history.

(56) References Cited

U.S. PATENT DOCUMENTS

| | | | |
|---|---|---|---|
| 7,601,332 | B2 | 10/2009 | Vlahov et al. |
| 8,105,568 | B2 | 1/2012 | Vlahov et al. |
| 2006/0024692 | A1 | 2/2006 | Nakamura et al. |
| 2007/0065449 | A1 | 3/2007 | Verschraegen |
| 2010/0004276 | A1 | 1/2010 | Vlahov et al. |
| 2010/0323973 | A1 | 12/2010 | Leamon et al. |
| 2012/0122893 | A1 | 5/2012 | Reddy et al. |
| 2012/0128587 | A1 | 5/2012 | Leamon et al. |
| 2013/0330326 | A1 | 12/2013 | Reddy et al. |

FOREIGN PATENT DOCUMENTS

| | | |
|---|---|---|
| WO | WO 2004/069159 | 8/2004 |

OTHER PUBLICATIONS

PCT Search Report and Written Opinion for PCT/US2011/060407, completed Mar. 21, 2012.
Reddy, Joseph A., et al., "Preclinical Evaluation of EC145, a Folate-Vinca Alkaloid Conjugate", May 1, 2007, Cancer Res., No. 67, pp. 4434.
Reddy, et al., "Preclinical Evaluation of EC145, a Folate-Vinca Alkaloid Conjugate," Cancer Research, 2007, vol. 67, p. 4434-4442.

*Primary Examiner* — Raymond Henley, III
(74) *Attorney, Agent, or Firm* — Barnes & Thornburg LLP

(57) ABSTRACT

Described are methods and compositions for treating epithelial tumors with a folate-vinca conjugate in combination with at least one other chemotherapeutic agent in which the tumors include ovarian, endometrial or non-small cell lung cancer tumors, including platinum-resistant ovarian tumors and platinum-sensitive ovarian tumors.

29 Claims, 44 Drawing Sheets

Same indicators as in FIG. 40

| Lapatinib Conc. with EC145 | $IC_{50}$, nM (Fold Reduction) | | |
|---|---|---|---|
| | *NCI/ADR-cl2* | *KB-DR300* | *KB* |
| 0 nM | 16,400 | 53,200 | 3.2 |
| 100 nM | 5700(3x) | 16400(3x) | 3.2 |
| 500 nM | 320(51x) | 220(242x) | 2.8 |
| 1000 nM | 38(432x) | 6.2(8600x) | 3.1 |

Fig 3. Median steady-state serum concentration profiles at each daily dose of lapatinib.

Burris (2005) JCO 23:5305.

METHODS OF TREATING CANCER

CROSS REFERENCE TO RELATED APPLICATIONS

This application is a U.S. national application under 35 U.S.C. §371(b) of International Application Serial No. PCT/US2011/060407 filed Nov. 11, 2011, and claims priority under 35 U.S.C. §119(e) to U.S. Provisional Application Ser. No. 61/413,275, each of which is incorporated herein by reference in its entirety.

TECHNICAL FIELD

The invention relates to methods and compositions for the treatment of a cancer with a folate-vinca conjugate in combination with at least one additional chemotherapeutic agent. The invention includes methods and compositions for the treatment of tumors including ovarian, endometrial or non-small cell lung cancers.

BACKGROUND AND SUMMARY

Despite the fact that there have been significant developments in anti-cancer technology, such as radiotherapy, chemotherapy and hormone therapy, cancer still remains the second leading cause of death following heart disease in the United States. Most often, cancer is treated with chemotherapy utilizing highly potent drugs, such as mitomycin, paclitaxel and camptothecin. In many cases, these chemotherapeutic agents show a dose responsive effect, and cell killing is proportional to drug dose. A highly aggressive style of dosing is thus necessary to eradicate neoplasms. However, high-dose chemotherapy is hindered by poor selectivity for cancer cells and severe toxicity to normal cells. This lack of tumor-specific treatment is one of the many hurdles that needs to be overcome by current chemotherapy.

One solution to current chemotherapy limitations would be to deliver a biologically effective concentration of anti-cancer agents to the tumor tissues with very high specificity. To reach this goal, much effort has been undertaken to develop tumor-selective drugs by conjugating anti-cancer drugs to such ligands as hormones, antibodies, or vitamins. For example, the low molecular weight vitamin compound, folate, is useful as a tumor-targeting agent.

Another approach to overcoming current chemotherapeutic limitations would be to deliver a combination of a tumor-targeted drug with one or more chemotherapeutic agents where the toxicity profile of the tumor-targeted drug and the chemotherapeutic agent are different. A further modification of this approach is to use the tumor-targeted drug and the chemotherapeutic agent in the combination treatment in amounts of each lower than typically used when the tumor-targeted drug or the chemotherapeutic agent is used alone for treatment.

Folate is a member of the B family of vitamins and plays an essential role in cell survival by participating in the biosynthesis of nucleic acids and amino acids. This essential vitamin is also a high affinity ligand that enhances the specificity of conjugated anti-cancer drugs by targeting folate receptor (FR)-positive cancer cells. The FR, a tumor associated glycosylphosphatidylinositol anchored protein, can actively internalize bound folates and folate conjugated compounds via receptor-mediated endocytosis. It has been found that the FR is up-regulated in more than 90% of non-mucinous ovarian carcinomas. The FR is also found at high to moderate levels in kidney, brain, lung, and breast carcinomas while it occurs at low levels in most normal tissues. The FR density also appears to increase as the stage of the cancer becomes more advanced.

Folate-targeted drugs have been developed and are being tested in clinical trials as cancer therapeutics. EC145 comprises a highly potent vinca alkaloid cytotoxic chemotherapeutic agent, desacetylvinblastine hydrazide (DAVLBH), conjugated to folate. The EC145 molecule targets the folate receptor found at high levels on the surface of epithelial tumors, including non-small cell lung carcinomas (NSCLC), ovarian, endometrial and renal cancers, and others, including fallopian tube and primary peritoneal carcinoma. Without being bound by theory, it is believed that EC145 binds to tumors that express the folate receptor delivering the vinca moiety directly to cancer cells while avoiding normal tissue. Upon binding, EC145 enters the cancer cell via endocytosis, releases DAVLBH and causes cell death by inhibiting formation of the mitotic assembly required for cell division. EC145 has the Chemical Abstracts Registry Number 742092-03-1 and the following formula

EC145

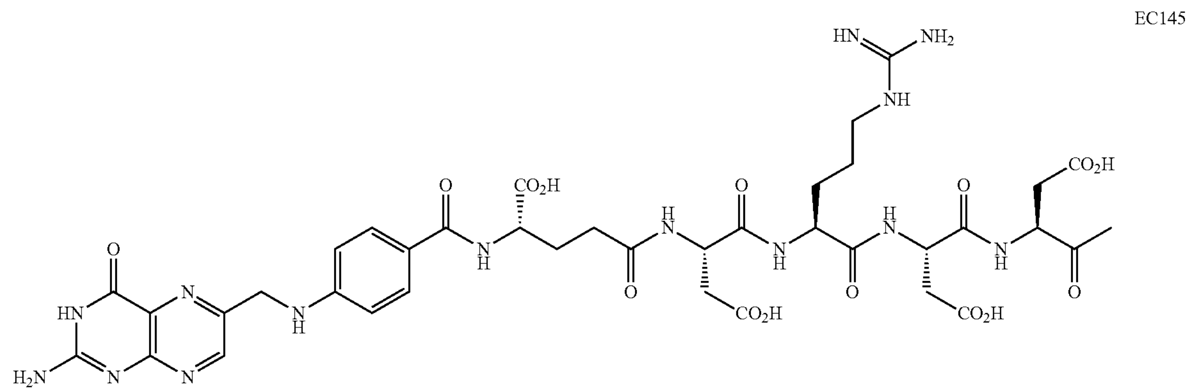

-continued

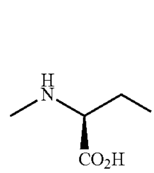
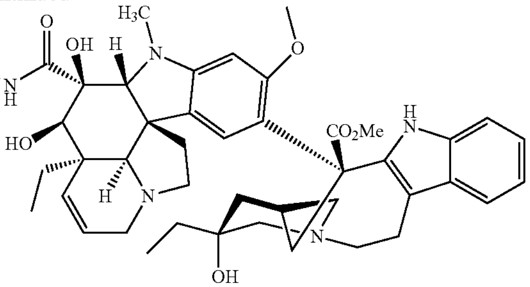

As used herein, in the context of a method of treatment, a use, a composition, a pharmaceutical composition, a kit, or a combination, the term EC145 means the chemotherapeutic agent, as indicated above, or a pharmaceutically acceptable salt thereof, and the chemotherapeutic agent may be present in solution or suspension in an ionized form, including a protonated form. EC145 can be synthesized, for example, by the method described in PCT/US11/037,134, incorporated herein by reference. EC145 is used interchangeably with the term "conjugate" herein.

In one embodiment, a method of treatment of a cancer is provided. The method comprises administering EC145 in combination with one or more chemotherapeutic agents having a mode of action selected from the group consisting of angiogenesis inhibition, microtubule assembly inhibition, DNA cross-linking, topoisomerase inhibition, apoptosis induction, DNA intercalation, DNA synthesis inhibition, tyrosine kinase inhibition, and mitosis inhibition.

In another embodiment, the preceding method wherein the one or more chemotherapeutic agents are selected from the group consisting of cisplatin (e.g., PLATINOLT™), carboplatin (e.g., PARAPLATIN™), topotecan (e.g., HYCAMTIN™), irinotecan (e.g., CAMTOSAR™), bevacizumab (e.g., AVASTIN™), erlotinib (e.g., TARCEVA™), lapatinib (e.g., TYKERB™), and pemetrexed (e.g., ALIMTA™) is described.

In another embodiment, use of EC145 in combination with one or more chemotherapeutic agents having a mode of action selected from the group consisting of angiogenesis inhibition, microtubule assembly inhibition, apoptosis induction, DNA cross-linking, topoisomerase inhibition, DNA intercalation, DNA synthesis inhibition, tyrosine kinase inhibition, and mitosis inhibition for the treatment of folate receptor expressing cancer cells is described.

In another embodiment, the use described above is provided wherein the one or more chemotherapeutic agents are selected from the group consisting of cisplatin, carboplatin, topotecan, irinotecan, bevacizumab, erlotinib, lapatinib, and pemetrexed.

In another embodiment, the use is provided of EC145 for the manufacture of a medicament for the treatment of folate receptor expressing cancer cells in combination with one or more chemotherapeutic agents having a mode of action selected from the group consisting of angiogenesis inhibition, microtubule assembly inhibition, apoptosis induction, DNA cross-linking, topoisomerase inhibition, DNA intercalation, DNA synthesis inhibition, tyrosine kinase inhibition, and mitosis inhibition.

In another embodiment, the use for manufacture of a medicament described above wherein the one or more chemotherapeutic agents are selected from the group consisting of cisplatin, carboplatin, topotecan, irinotecan, bevacizumab, erlotinib, lapatinib, and pemetrexed is described.

In another embodiment, a pharmaceutical composition or combination comprising EC145 and one or more chemotherapeutic agents having a mode of action selected from the group consisting of angiogenesis inhibition, microtubule assembly inhibition, DNA cross-linking, topoisomerase inhibition, DNA intercalation, apoptosis induction, DNA synthesis inhibition, tyrosine kinase inhibition, and mitosis inhibition.

In another embodiment, the pharmaceutical composition or combination described in the preceding embodiment wherein the one or more chemotherapeutic agents are selected from the group consisting of cisplatin, carboplatin, topotecan, irinotecan, bevacizumab, erlotinib, lapatinib, and pemetrexed is described.

In another embodiment, a composition comprising EC145 and one or more chemotherapeutic agents having a mode of action selected from the group consisting of angiogenesis inhibition, microtubule assembly inhibition, apoptosis induction, DNA cross-linking, topoisomerase inhibition, DNA intercalation, DNA synthesis inhibition, tyrosine kinase inhibition, and mitosis inhibition.

In another embodiment, the composition described in the preceding embodiment wherein the one or more chemotherapeutic agents are selected from the group consisting of cisplatin, carboplatin, topotecan, irinotecan, bevacizumab, erlotinib, lapatinib, and pemetrexed is described.

In any of the above-described embodiments, the chemotherapeutic agent can also be doxorubicin, or a modified form of doxorubicin such as pegylated doxorubicin (e.g., DOXIL™). The doxorubicin (e.g., DOXIL™) can be liposome-encapsulated.

Several embodiments of the invention are described by the following enumerated clauses:

1. A method of treatment of a cancer, the method comprising the step of administering EC145 in combination with one or more chemotherapeutic agents having a mode of action selected from the group consisting of angiogenesis inhibition, microtubule assembly inhibition, DNA cross-linking, topoisomerase inhibition, DNA intercalation, DNA synthesis inhibition, tyrosine kinase inhibition, and mitosis inhibition.

2. The method of clause 1 wherein the one or more chemotherapeutic agents are selected from the group consisting of cisplatin, carboplatin, topotecan, irinotecan, bevacizumab, erlotinib, lapatinib, and pemetrexed.

3. The method of clause 1 or 2 wherein the chemotherapeutic agent is carboplatin.

4. The method of clause 1 or 2 wherein the chemotherapeutic agent is bevacizumab.

5. Use of EC145 in combination with one or more chemotherapeutic agents having a mode of action selected from the group consisting of angiogenesis inhibition, microtubule assembly inhibition, DNA cross-linking, topoisomerase inhibition, DNA intercalation, DNA synthesis inhibition, tyrosine kinase inhibition, and mitosis inhibition for the treatment of folate receptor expressing cancer cells.

6. The use of clause 5 wherein the one or more chemotherapeutic agents are selected from the group consisting of cisplatin, carboplatin, topotecan, irinotecan, bevacizumab, erlotinib, lapatinib, and pemetrexed.

7. The use of clause 5 or 6 wherein the chemotherapeutic agent is carboplatin.

8. The use of clause 5 or 6 wherein the chemotherapeutic agent is bevacizumab.

9. Use of EC145 for the manufacture of a medicament for the treatment of folate receptor expressing cancer cells in combination with one or more chemotherapeutic agents having a mode of action selected from the group consisting of angiogenesis inhibition, microtubule assembly inhibition, DNA cross-linking, topoisomerase inhibition, DNA intercalation, DNA synthesis inhibition, tyrosine kinase inhibition, and mitosis inhibition.

10. The use of clause 9 wherein the one or more chemotherapeutic agents are selected from the group consisting of cisplatin, carboplatin, topotecan, irinotecan, bevacizumab, erlotinib, lapatinib, and pemetrexed.

11. The use of clause 9 or 10 wherein the chemotherapeutic agent is carboplatin.

12. The use of clause 9 or 10 wherein the chemotherapeutic agent is bevacizumab.

13. The method or use of any one of the preceding clauses wherein the folate receptor expressing cells are epithelial tumor cells.

14. The method or use of clause 13 wherein the epithelial tumor is an ovarian, an endometrial or a non-small cell lung tumor.

15. The method or use of any one of clauses 13 to 14 wherein the folate receptor expressing epithelial tumor is an ovarian tumor.

16. The method or use of any one of clauses 13 to 15 wherein the tumor is a primary tumor.

17. The method or use of any one of clauses 13 to 15 wherein the tumor is a metastatic tumor.

18. The method or use of any one of the preceding clauses wherein the chemotherapeutic agent is administered in a dose that is 50 to 80% of the maximum tolerated dose for the chemotherapeutic agent.

19. A pharmaceutical composition comprising EC145 and one or more chemotherapeutic agents having a mode of action selected from the group consisting of angio genesis inhibition, microtubule assembly inhibition, DNA cross-linking, topoisomerase inhibition, DNA intercalation, DNA synthesis inhibition, tyrosine kinase inhibition, and mitosis inhibition.

20. The composition of clause 19 wherein the one or more chemotherapeutic agents are selected from the group consisting of cisplatin, carboplatin, topotecan, irinotecan, bevacizumab, erlotinib, lapatinib, and pemetrexed.

21. The composition of clause 19 to 20 wherein the chemotherapeutic agent is carboplatin.

22. The composition of clause 19 to 20 wherein the chemotherapeutic agent is bevacizumab.

23. A composition comprising EC145 and one or more chemotherapeutic agents having a mode of action selected from the group consisting of angiogenesis inhibition, microtubule assembly inhibition, DNA cross-linking, topoisomerase inhibition, DNA intercalation, DNA synthesis inhibition, tyrosine kinase inhibition, and mitosis inhibition for treating a cancer.

24. The composition of clause 23 wherein the one or more chemotherapeutic agents are selected from the group consisting of cisplatin, carboplatin, topotecan, irinotecan, bevacizumab, erlotinib, lapatinib, and pemetrexed.

25. The composition of clause 23 or 24 wherein the chemotherapeutic agent is carboplatin.

26. The composition of clause 23 or 24 wherein the chemotherapeutic agent is bevacizumab.

27. The composition, method, or use of any one of the preceding clauses wherein the EC145 or the chemotherapeutic agent is in a parenteral dosage form.

28. The composition, method, or use of any one of the preceding clauses wherein the dosage form is selected from the group consisting of intradermal, subcutaneous, intramuscular, intraperitoneal, intravenous, and intrathecal.

29. The composition, method, or use of any one of the preceding clauses wherein the EC145 or the chemotherapeutic agent is in a composition and wherein the composition further comprises a pharmaceutically acceptable carrier.

30. The composition, method or use of clause 29 wherein the pharmaceutically acceptable carrier is a liquid carrier.

31. The composition, method or use of clause 30 wherein the liquid carrier is selected from the group consisting of saline, glucose, alcohols, glycols, esters, amides, and a combination thereof.

32. The composition, method, or use of any one of the preceding clauses wherein the EC145 or the chemotherapeutic agent is administered in a therapeutically effective amount.

33. The composition, method, or use of clause 32 wherein the effective amount ranges from about 1 ng to about 1 mg per kilogram of body weight.

34. The composition, method, or use of clause 33 wherein the effective amount ranges from about 100 ng to about 500 μg per kilogram of body weight.

35. The composition, method, or use of clause 34 wherein the effective amount ranges from about 100 ng to about 50 μg per kilogram of body weight.

36. The composition, method, or use of any one of the preceding clauses wherein the tumor is a platinum-resistant ovarian tumor.

37. A method of treatment of a cancer, the method comprising the steps of administering EC145 to a patient; and administering to the patient one or more additional chemotherapeutic agents having a mode of action selected from the group consisting of angiogenesis inhibition, microtubule assembly inhibition, DNA cross-linking, topoisomerase inhibition, DNA intercalation, DNA synthesis inhibition, tyrosine kinase inhibition, and mitosis inhibition.

38. Use of EC145 in combination with one or more additional chemotherapeutic agents having a mode of action selected from the group consisting of angiogenesis inhibition, microtubule assembly inhibition, DNA cross-linking, topoisomerase inhibition, DNA intercalation, DNA synthesis inhibition, tyrosine kinase inhibition, and mitosis inhibition for the treatment of folate receptor expressing cancer cells.

39. Use of EC145 for the manufacture of a medicament for the treatment of folate receptor expressing cancer cells in combination with one or more additional chemotherapeutic agents having a mode of action selected from the group consisting of angiogenesis inhibition, microtubule assembly inhibition, DNA cross-linking, topoisomerase inhibition, DNA intercalation, DNA synthesis inhibition, tyrosine kinase inhibition, and mitosis inhibition.

40. The method or use of any one of clauses 37 to 39 wherein the additional chemotherapeutic agent is selected from the group consisting of cisplatin, carboplatin, topotecan, irinotecan, bevacizumab, erlotinib, lapatinib, and pemetrexed.

41. The method or use of any one of clauses 37 to 40 wherein the additional chemotherapeutic agent is selected from the group consisting of carboplatin and bevacizumab.

42. The method or use of any one of clauses 37 to 41 wherein the additional chemotherapeutic agent is carboplatin.

43. The method or use of any one of clauses 37 to 41 wherein the additional chemotherapeutic agent is bevacizumab.

44. The use of any one of clauses 38 to 43 wherein the folate receptor expressing cells are epithelial tumor cells.

45. The use of clause 44 wherein the epithelial tumor is an ovarian, an endometrial, or a non-small cell lung tumor.

46. The use of clause 45 wherein the folate receptor expressing epithelial tumor is an ovarian tumor.

47. The use of clause 45 wherein the folate receptor expressing epithelial tumor is a non-small cell lung tumor.

48. The method of any one of clauses 37 or 40 to 43 wherein the cancer is an epithelial cancer.

49. The method of clause 48 wherein the epithelial cancer is an ovarian, an endometrial, or a non-small cell lung cancer.

50. The method of clause 49 wherein the epithelial cancer is an ovarian cancer.

51. The method of clause 49 wherein the epithelial cancer is a non-small cell lung cancer.

52. The method or use of any one of clauses 37 to 51 wherein the cancer or the cancer cells comprise a primary tumor.

53. The method or use of any of one of clauses 37 to 51 wherein the cancer or the cancer cells comprise metastatic tumor cells.

54. The method or use of any one of clauses 37 to 53 wherein the additional chemotherapeutic agent is administered at a dose that is 50 to 80% of the maximum tolerated dose for the chemotherapeutic agent.

55. The method or use of any one of clauses 37 to 54 wherein the EC145 and the additional chemotherapeutic agent are in parenteral dosage forms.

56. The method or use of clause 55 wherein the dosage forms are independently selected from the group consisting of intradermal, subcutaneous, intramuscular, intraperitoneal, intravenous, and intrathecal.

57. The method or use of any one of clauses 37 to 56 wherein the EC145 is in a composition and the additional chemotherapeutic agent is in a composition and wherein the compositions further comprise pharmaceutically acceptable carriers.

58. The method or use of clause 57 wherein the pharmaceutically acceptable carriers are liquid carriers.

59. The method or use of clause 58 wherein the liquid carriers are independently selected from the group consisting of saline, glucose, alcohols, glycols, esters, amides, and a combination thereof.

60. The method or use of any one of clauses 37 to 59 wherein the EC145 and the chemotherapeutic agent are administered in therapeutically effective amounts.

61. The method or use of clause 60 wherein the effective amounts range from about 1 $\mu g/m^2$ to about 500 $mg/m^2$ of body surface area.

62. The method or use of clause 61 wherein the effective amounts range from about 1 $\mu g/m^2$ to about 300 $mg/m^2$ of body surface area.

63. The method or use of clause 60 wherein the effective amounts range from about 10 μg/kg to about 100 μg/kg of patient body weight.

64. The method of clause 50 wherein the cancer is a platinum-resistant ovarian cancer.

65. The use of clause 46 wherein the tumor is a platinum-resistant ovarian tumor.

66. The method or use of any one of clauses 37 to 65 wherein the EC145 and the additional chemotherapeutic agent are in sterile containers or packages.

67. The method or use of any one of clauses 37 to 66 wherein the EC145 and the additional chemotherapeutic agent have a purity of at least 90% based on weight percentage.

68. The method or use of any one of clauses 37 to 67 wherein the EC145 is in the form of a reconstitutable lyophilizate.

69. The method or use of any one of clauses 37 to 68 wherein the EC145 and the additional chemotherapeutic agent are in sterile, pyrogen-free aqueous solutions.

70. A composition or combination comprising EC145 and one or more additional chemotherapeutic agents having a mode of action selected from the group consisting of angiogenesis inhibition, microtubule assembly inhibition, DNA cross-linking, topoisomerase inhibition, DNA intercalation, DNA synthesis inhibition, tyrosine kinase inhibition, and mitosis inhibition.

71. A composition or combination for treating a cancer comprising EC145 and one or more additional chemotherapeutic agents having a mode of action selected from the group consisting of angiogenesis inhibition, microtubule assembly inhibition, DNA cross-linking, topoisomerase inhibition, DNA intercalation, DNA synthesis inhibition, tyrosine kinase inhibition, and mitosis inhibition.

72. A kit comprising EC145 and one or more additional chemotherapeutic agents having a mode of action selected from the group consisting of angiogenesis inhibition, microtubule assembly inhibition, DNA cross-linking, topoisomerase inhibition, DNA intercalation, DNA synthesis inhibition, tyrosine kinase inhibition, and mitosis inhibition.

73. The composition, combination, or kit of any one of clauses 70 to 72 wherein the additional chemotherapeutic agent is selected from the group consisting of cisplatin, carboplatin, topotecan, irinotecan, bevacizumab, erlotinib, lapatinib, and pemetrexed.

74. The composition, combination, or kit of any one of clauses 70 to 73 wherein the additional chemotherapeutic agent is selected from the group consisting of carboplatin and bevacizumab.

75. The composition, combination, or kit of any one of clauses 70 to 74 wherein the additional chemotherapeutic agent is carboplatin.

76. The composition, combination, or kit of any one of clauses 70 to 74 wherein the additional chemotherapeutic agent is bevacizumab.

77. The composition, combination, or kit of any one of clauses 70 to 76 wherein the EC145 and the additional chemotherapeutic agent are in parenteral dosage forms.

78. The composition, combination, or kit of clause 77 wherein the dosage forms are independently selected from the group consisting of intradermal, subcutaneous, intramuscular, intraperitoneal, intravenous, and intrathecal.

79. The composition, combination, or kit of any one of clauses 70 to 78 wherein the EC145 and the additional chemotherapeutic agent are in pharmaceutical compositions and the compositions further comprise pharmaceutically acceptable carriers.

80. The composition, combination, or kit of clause 79 wherein the pharmaceutically acceptable carriers are liquid carriers.

81. The composition, combination, or kit of clause 80 wherein the liquid carriers are independently selected from the group consisting of saline, glucose, alcohols, glycols, esters, amides, and a combination thereof.

82. The composition, combination, or kit of any one of clauses 70 to 81 wherein the EC145 and the chemotherapeutic agent are in therapeutically effective amounts.

83. The composition, combination, or kit of any one of clauses 70 to 82 wherein the EC145 and the additional chemotherapeutic agent are in sterile containers or packages.

84. The composition, combination, or kit of any one of clauses 70 to 83 wherein the EC145 and the additional chemotherapeutic agent have a purity of at least 90% based on weight percentage.

85. The composition, combination, or kit of any one of clauses 70 to 83 wherein the EC145 and the additional chemotherapeutic agent have a purity of at least 95% based on weight percentage.

86. The composition, combination, or kit of any one of clauses 70 to 85 wherein the EC145 is in the form of a reconstitutable lyophilizate.

87. The composition, combination, or kit of any one of clauses 70 to 86 wherein the EC145 and the additional chemotherapeutic agent are in sterile, pyrogen-free aqueous solutions.

88. The method or use of any one of clauses 37 to 59 wherein the EC145 and/or the additional chemotherapeutic agent are administered at doses lower than their maximum tolerable doses.

89. The composition, combination, or kit of any one of clauses 70 to 85 or the method or use of any one of clauses 37 to 67 wherein the EC145 is in the form of a lyophilizate.

DEFINITIONS

Figure 1:
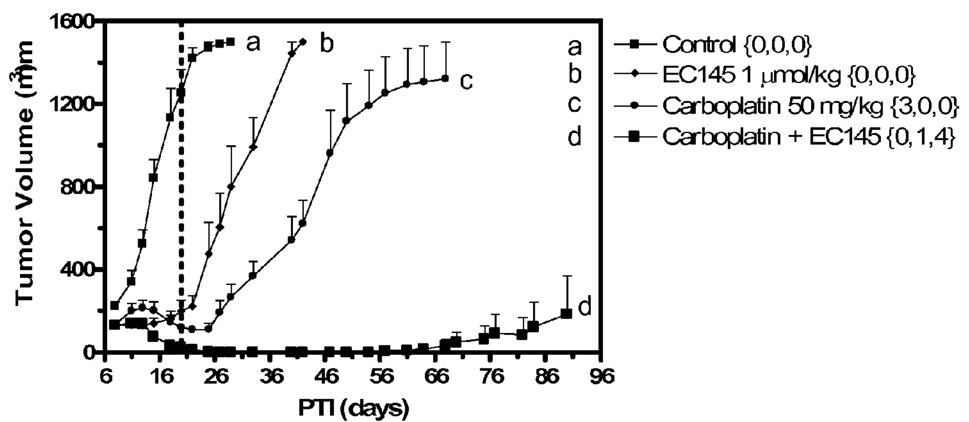
FIG. 1. Tumor volume (average for the five animals in each treatment group) measured for nu/nu mice with KB tumors (109-188 $mm^3$ range) that were (a) untreated; or treated with either: (b) EC145 at 1 μmol/kg/injection, TIW for 2 weeks; or (c) Carboplatin at 50 mg/kg, TIW for 1 week or (d) EC145 at 1 μmol/kg/injection, TIW for 2 weeks+Carboplatin at 50 mg/kg, TIW for 1 week. Treatment with EC145 alone resulted in 0 partial responses, 0 complete responses, and 0 Cures. Treatment with Carboplatin alone resulted in 3 partial responses. The combination treatment resulted in 1 complete response and 4 Cures.

As used herein, the term "inhibition of tumor growth" means reduction in tumor size, complete disappearance of a tumor, or growth of a patient's tumor of less than 30% over the course of therapy with EC145 and the additional chemotherapeutic drug.

As used herein, in the context of a method of treatment, a use, a composition, a pharmaceutical composition, a combination, or a kit, the term topotecan means a composition comprising the chemotherapeutic agent identified by the Chemical Abstracts registry number 123948-87-8, or a pharmaceutically acceptable salt thereof; and the chemotherapeutic agent may be present in solution or suspension in an ionized form or non-ionized form.

As used herein, in the context of a method of treatment, a use, a composition, a pharmaceutical composition, a combination, or a kit, the term cisplatin means a composition comprising the chemotherapeutic agent identified by the Chemical Abstracts registry number 15663-27-1; and the chemotherapeutic agent may be present in solution or suspension.

As used herein, in the context of a method of treatment, a use, a composition, a pharmaceutical composition, a combination, or a kit, the term carboplatin means a composition comprising the chemotherapeutic agent identified by the Chemical Abstracts registry number 41575-94-4; and the chemotherapeutic agent may be present in solution or suspension.

As used herein, in the context of a method of treatment, a use, a composition, a pharmaceutical composition, a combination, or a kit, the term irinotecan means a composition comprising the chemotherapeutic agent identified by the Chemical Abstracts registry number 100286-90-6, or a pharmaceutically acceptable salt thereof; and the chemotherapeutic agent may be present in solution or suspension.

As used herein, in the context of a method of treatment, a use, a composition, a pharmaceutical composition, a combination, or a kit, the term bevacizumab means a composition comprising the chemotherapeutic agent identified by the Chemical Abstracts registry number 216974-75-3, or a pharmaceutically acceptable salt thereof; and the chemotherapeutic agent may be present in solution or suspension.

As used herein, in the context of a method of treatment, a use, a composition, a pharmaceutical composition, a combination, or a kit, the term gemcitabine means a composition comprising the chemotherapeutic agent identified by the Chemical Abstracts registry number 95058-81-4, or a pharmaceutically acceptable salt thereof; and the chemotherapeutic agent may be present in solution or suspension.

As used herein, in the context of a method of treatment, a use, a composition, a pharmaceutical composition, a combination, or a kit, the term erlotinib means a composition comprising the chemotherapeutic agent identified by the Chemical Abstracts registry number 183321-74-6, or a pharmaceutically acceptable salt thereof; and the chemotherapeutic agent may be present in solution or suspension.

As used herein, in the context of a method of treatment, a use, a composition, a pharmaceutical composition, a combination, or a kit, the term lapatinib means a composition comprising the chemotherapeutic agent identified by the Chemical Abstracts registry number 231277-92-2, or a pharmaceutically acceptable salt thereof; and the chemotherapeutic agent may be present in solution or suspension.

As used herein, in the context of a method of treatment, a use, a composition, a pharmaceutical composition, a combination, or a kit, the term pemetrexed means a composition comprising the chemotherapeutic agent identified by the Chemical Abstracts registry number 137281-23-3, or a pharmaceutically acceptable salt thereof; and the chemotherapeutic agent may be present in solution or suspension.

As used herein, in the context of a method of treatment, a use, a composition, a pharmaceutical composition, a combination, or a kit, the term vinorelbine means a composition comprising the chemotherapeutic agent identified by the Chemical Abstracts registry number 71486-22-1; or a pharmaceutically acceptable salt thereof; and the chemotherapeutic agent may be present in solution or suspension.

DETAILED DESCRIPTION OF ILLUSTRATIVE EMBODIMENTS

Several embodiments of the invention are described by the following enumerated clauses and each of the embodiments described in this Detailed Description section of this application apply to each of the following embodiments:

1. A method of treatment of a cancer, the method comprising the step of administering EC145 in combination with one or more chemotherapeutic agents having a mode of action selected from the group consisting of angiogenesis inhibition, microtubule assembly inhibition, DNA cross-linking, topoisomerase inhibition, DNA intercalation, DNA synthesis inhibition, tyrosine kinase inhibition, and mitosis inhibition.

2. The method of clause 1 wherein the one or more chemotherapeutic agents are selected from the group consisting of doxorubicin, cisplatin, carboplatin, topotecan, irinotecan, bevacizumab, erlotinib, lapatinib, and pemetrexed.

3. The method of clause 1 or 2 wherein the chemotherapeutic agent is carboplatin.

4. The method of clause 1 or 2 wherein the chemotherapeutic agent is bevacizumab.

5. Use of EC145 in combination with one or more chemotherapeutic agents having a mode of action selected from the group consisting of angiogenesis inhibition, microtubule assembly inhibition, DNA cross-linking, topoisomerase inhibition, DNA intercalation, DNA synthesis inhibition, tyrosine kinase inhibition, and mitosis inhibition for the treatment of folate receptor expressing cancer cells.

6. The use of clause 5 wherein the one or more chemotherapeutic agents are selected from the group consisting of doxorubicin, cisplatin, carboplatin, topotecan, irinotecan, bevacizumab, erlotinib, lapatinib, and pemetrexed.

7. The use of clause 5 or 6 wherein the chemotherapeutic agent is carboplatin.

8. The use of clause 5 or 6 wherein the chemotherapeutic agent is bevacizumab.

9. Use of EC145 for the manufacture of a medicament for the treatment of folate receptor expressing cancer cells in combination with one or more chemotherapeutic agents having a mode of action selected from the group consisting of angiogenesis inhibition, microtubule assembly inhibition, DNA cross-linking, topoisomerase inhibition, DNA intercalation, DNA synthesis inhibition, tyrosine kinase inhibition, and mitosis inhibition.

10. The use of clause 9 wherein the one or more chemotherapeutic agents are selected from the group consisting of doxorubicin, cisplatin, carboplatin, topotecan, irinotecan, bevacizumab, erlotinib, lapatinib, and pemetrexed.

11. The use of clause 9 or 10 wherein the chemotherapeutic agent is carboplatin.

12. The use of clause 9 or 10 wherein the chemotherapeutic agent is bevacizumab.

13. The method or use of any one of the preceding clauses wherein the folate receptor expressing cells are epithelial tumor cells.

14. The method or use of clause 13 wherein the epithelial tumor is an ovarian, an endometrial or a non-small cell lung tumor.

15. The method or use of any of one clauses 13 to 14 wherein the folate receptor expressing epithelial tumor is an ovarian tumor.

16. The method or use of any of one clauses 13 to 15 wherein the tumor is a primary tumor.

17. The method or use of any of one clauses 13 to 15 wherein the tumor is a metastatic tumor.

18. The method or use of any one of the preceding clauses wherein the chemotherapeutic agent is administered in a dose that is 50-80% of the maximum tolerated dose for the chemotherapeutic agent.

19. A pharmaceutical composition comprising EC145 and one or more chemotherapeutic agents having a mode of action selected from the group consisting of angiogenesis inhibition, microtubule assembly inhibition, DNA cross-linking, topoisomerase inhibition, DNA intercalation, DNA synthesis inhibition, tyrosine kinase inhibition, and mitosis inhibition.

20. The composition of clause 19 wherein the one or more chemotherapeutic agents are selected from the group consisting of doxorubicin, cisplatin, carboplatin, topotecan, irinotecan, bevacizumab, erlotinib, lapatinib, and pemetrexed.

21. The composition of clause 19 to 20 wherein the chemotherapeutic agent is carboplatin.

22. The composition of clause 19 to 20 wherein the chemotherapeutic agent is bevacizumab.

23. A composition comprising EC145 and one or more chemotherapeutic agents having a mode of action selected from the group consisting of angiogenesis inhibition, microtubule assembly inhibition, DNA cross-linking, topoisomerase inhibition, DNA intercalation, DNA synthesis inhibition, tyrosine kinase inhibition, and mitosis inhibition for treating a cancer.

24. The composition of clause 23 wherein the one or more chemotherapeutic agents are selected from the group consisting of doxorubicin, cisplatin, carboplatin, topotecan, irinotecan, bevacizumab, erlotinib, lapatinib, and pemetrexed.

25. The composition of clause 23 or 24 wherein the chemotherapeutic agent is carboplatin.

26. The composition of clause 23 or 24 wherein the chemotherapeutic agent is bevacizumab.

27. The composition, method, or use of any one of the preceding clauses wherein the EC145 or the chemotherapeutic agent is in a parenteral dosage form.

28. The composition, method, or use of any one of the preceding clauses wherein the dosage form is selected from the group consisting of intradermal, subcutaneous, intramuscular, intraperitoneal, intravenous, and intrathecal.

29. The composition, method, or use of any one of the preceding clauses wherein the EC145 or the chemotherapeutic agent is in a composition and wherein the composition further comprises a pharmaceutically acceptable carrier.

30. The composition, method or use of clause 29 wherein the pharmaceutically acceptable carrier is a liquid carrier.

31. The composition, method or use of clause 30 wherein the liquid carrier is selected from the group consisting of saline, glucose, alcohols, glycols, esters, amides, and a combination thereof.

32. The composition, method, or use of any one of the preceding clauses wherein the EC145 or the chemotherapeutic agent is administered in a therapeutically effective amount.

33. The composition, method, or use of clause 32 wherein the effective amount ranges from about 1 ng to about 1 mg per kilogram of body weight.

34. The composition, method, or use of clause 33 wherein the effective amount ranges from about 100 ng to about 500 μg per kilogram of body weight.

35. The composition, method, or use of clause 34 wherein the effective amount ranges from about 100 ng to about 50 μg per kilogram of body weight.

36. The composition, method, or use of any one of the preceding clauses wherein the tumor is a platinum-resistant ovarian tumor.

37. A method of treatment of a cancer, the method comprising the steps of administering EC145 to a patient; and administering to the patient one or more additional chemotherapeutic agents having a mode of action selected from the group consisting of angiogenesis inhibition, microtubule assembly inhibition, DNA cross-linking, topoisomerase inhibition, DNA intercalation, DNA synthesis inhibition, tyrosine kinase inhibition, and mitosis inhibition.

38. Use of EC145 in combination with one or more additional chemotherapeutic agents having a mode of action selected from the group consisting of angiogenesis inhibition, microtubule assembly inhibition, DNA cross-linking, topoisomerase inhibition, DNA intercalation, DNA synthesis inhibition, tyrosine kinase inhibition, and mitosis inhibition for the treatment of folate receptor expressing cancer cells.

39. Use of EC145 for the manufacture of a medicament for the treatment of folate receptor expressing cancer cells in combination with one or more additional chemotherapeutic agents having a mode of action selected from the group consisting of angiogenesis inhibition, microtubule assembly inhibition, DNA cross-linking, topoisomerase inhibition, DNA intercalation, DNA synthesis inhibition, tyrosine kinase inhibition, and mitosis inhibition.

40. The method or use of any one of clauses 37 to 39 wherein the additional chemotherapeutic agent is selected from the group consisting of doxorubicin, cisplatin, carboplatin, topotecan, irinotecan, bevacizumab, erlotinib, lapatinib, and pemetrexed.

41. The method or use of any one of clauses 37 to 40 wherein the additional chemotherapeutic agent is selected from the group consisting of carboplatin and bevacizumab.

42. The method or use of any one of clauses 37 to 41 wherein the additional chemotherapeutic agent is carboplatin.

43. The method or use of any one of clauses 37 to 41 wherein the additional chemotherapeutic agent is bevacizumab.

44. The use of any one of clauses 38 to 43 wherein the folate receptor expressing cells are epithelial tumor cells.

45. The use of clause 44 wherein the epithelial tumor is an ovarian, an endometrial, or a non-small cell lung tumor.

46. The use of clause 45 wherein the folate receptor expressing epithelial tumor is an ovarian tumor.

47. The use of clause 45 wherein the folate receptor expressing epithelial tumor is a non-small cell lung tumor.

48. The method of any one of clauses 37 or 40 to 43 wherein the cancer is an epithelial cancer.

49. The method of clause 48 wherein the epithelial cancer is an ovarian, an endometrial, or a non-small cell lung cancer.

50. The method of clause 49 wherein the epithelial cancer is an ovarian cancer.

51. The method of clause 49 wherein the epithelial cancer is a non-small cell lung cancer.

52. The method or use of any one of clauses 37 to 51 wherein the cancer or the cancer cells comprise a primary tumor.

53. The method or use of any of one of clauses 37 to 51 wherein the cancer or the cancer cells comprise metastatic tumor cells.

54. The method or use of any one of clauses 37 to 53 wherein the additional chemotherapeutic agent is administered at a dose that is 50 to 80% of the maximum tolerated dose for the chemotherapeutic agent.

55. The method or use of any one of clauses 37 to 54 wherein the EC145 and the additional chemotherapeutic agent or agents are in parenteral dosage forms.

56. The method or use of clause 55 wherein the dosage forms are independently selected from the group consisting of intradermal, subcutaneous, intramuscular, intraperitoneal, intravenous, and intrathecal.

57. The method or use of any one of clauses 37 to 56 wherein the EC145 is in a composition and the additional chemotherapeutic agent is in a composition and wherein the compositions further comprise pharmaceutically acceptable carriers.

58. The method or use of clause 57 wherein the pharmaceutically acceptable carriers are liquid carriers.

59. The method or use of clause 58 wherein the liquid carriers are independently selected from the group consisting of saline, glucose, alcohols, glycols, esters, amides, and a combination thereof.

60. The method or use of any one of clauses 37 to 59 wherein the EC145 and the chemotherapeutic agent are administered in therapeutically effective amounts.

61. The method or use of clause 60 wherein the effective amounts range from about 1 $\mu g/m^2$ to about 500 $mg/m^2$ of body surface area.

62. The method or use of clause 61 wherein the effective amounts range from about 1 $\mu g/m^2$ to about 300 $mg/m^2$ of body surface area.

63. The method or use of clause 60 wherein the effective amounts range from about 10 μg/kg to about 100 μg/kg of patient body weight.

64. The method of clause 50 wherein the cancer is a platinum-resistant ovarian cancer.

65. The use of clause 46 wherein the tumor is a platinum-resistant ovarian tumor.

66. The method or use of any one of clauses 37 to 65 wherein the EC145 and the additional chemotherapeutic agent are in sterile containers or packages.

67. The method or use of any one of clauses 37 to 66 wherein the EC145 and the additional chemotherapeutic agent have a purity of at least 90% based on weight percentage.

68. The method or use of any one of clauses 37 to 67 wherein the EC145 is in the form of a reconstitutable lyophilizate.

69. The method or use of any one of clauses 37 to 68 wherein the EC145 and the additional chemotherapeutic agent are in sterile, pyrogen-free aqueous solutions.

70. A composition or combination comprising EC145 and one or more additional chemotherapeutic agents having a mode of action selected from the group consisting of angiogenesis inhibition, microtubule assembly inhibition, DNA cross-linking, topoisomerase inhibition, DNA intercalation, DNA synthesis inhibition, tyrosine kinase inhibition, and mitosis inhibition.

71. A composition or combination for treating a cancer comprising EC145 and one or more additional chemotherapeutic agents having a mode of action selected from the group consisting of angiogenesis inhibition, microtubule assembly inhibition, DNA cross-linking, topoisomerase inhibition, DNA intercalation, DNA synthesis inhibition, tyrosine kinase inhibition, and mitosis inhibition.

72. A kit comprising EC145 and one or more additional chemotherapeutic agents having a mode of action selected from the group consisting of angiogenesis inhibition, microtubule assembly inhibition, DNA cross-linking, topoisomerase inhibition, DNA intercalation, DNA synthesis inhibition, tyrosine kinase inhibition, and mitosis inhibition.

73. The composition, combination, or kit of any one of clauses 70 to 72 wherein the additional chemotherapeutic agent is selected from the group consisting of doxorubicin, cisplatin, carboplatin, topotecan, irinotecan, bevacizumab, erlotinib, lapatinib, and pemetrexed.

74. The composition, combination, or kit of any one of clauses 70 to 73 wherein the additional chemotherapeutic agent is selected from the group consisting of carboplatin and bevacizumab.

75. The composition, combination, or kit of any one of clauses 70 to 74 wherein the additional chemotherapeutic agent is carboplatin.

76. The composition, combination, or kit of any one of clauses 70 to 74 wherein the additional chemotherapeutic agent is bevacizumab.

77. The composition, combination, or kit of any one of clauses 70 to 76 wherein the EC145 and the additional chemotherapeutic agent are in parenteral dosage forms.

78. The composition, combination, or kit of clause 77 wherein the dosage forms are independently selected from the group consisting of intradermal, subcutaneous, intramuscular, intraperitoneal, intravenous, and intrathecal.

79. The composition, combination, or kit of any one of clauses 70 to 78 wherein the EC145 and the additional chemotherapeutic agent are in pharmaceutical compositions and the compositions further comprise pharmaceutically acceptable carriers.

80. The composition, combination, or kit of clause 79 wherein the pharmaceutically acceptable carriers are liquid carriers.

81. The composition, combination, or kit of clause 80 wherein the liquid carriers are independently selected from the group consisting of saline, glucose, alcohols, glycols, esters, amides, and a combination thereof.

82. The composition, combination, or kit of any one of clauses 70 to 81 wherein the EC145 and the chemotherapeutic agent are in therapeutically effective amounts.

83. The composition, combination, or kit of any one of clauses 70 to 82 wherein the EC145 and the additional chemotherapeutic agent are in sterile containers or packages.

84. The composition, combination, or kit of any one of clauses 70 to 83 wherein the EC145 and the additional chemotherapeutic agent have a purity of at least 90% based on weight percentage.

85. The composition, combination, or kit of any one of clauses 70 to 83 wherein the EC145 and the additional chemotherapeutic agent have a purity of at least 95% based on weight percentage.

86. The composition, combination, or kit of any one of clauses 70 to 85 wherein the EC145 is in the form of a reconstitutable lyophilizate.

87. The composition, combination, or kit of any one of clauses 70 to 86 wherein the EC145 and the additional chemotherapeutic agent are in sterile, pyrogen-free aqueous solutions.

88. The method or use of any one of clauses 37 to 59 wherein the EC145 and/or the additional chemotherapeutic agent are administered at doses lower than their maximum tolerable doses.

In any of the various embodiments described herein, the following features may be present where applicable, providing additional embodiments of the invention.

For all of the embodiments, any applicable combination of embodiments is also contemplated. Any applicable combination of the above-described embodiments is considered to be in accordance with the invention.

In various embodiments of the methods, uses, compositions, combinations, pharmaceutical combinations, or kits described herein, the EC145 may be administered alone or in combination with one or more of the additional chemotherapeutic agents (cisplatin, carboplatin, topotecan, irinotecan, bevacizumab, erlotinib, lapatinib, or pemetrexed, or with any combination of these agents). In various embodiments described herein, the other chemotherapeutic agents may be selected from a drug that has a mode of action selected from the group consisting of angiogenesis inhibition, microtubule assembly inhibition, DNA cross-linking, topoisomerase inhibition, DNA intercalation, DNA synthesis inhibition, tyrosine kinase inhibition, and mitosis inhibition. It is appreciated that the other drug may have more than one mode of action. In one illustrative embodiment, the EC145 can be administered in combination with at least one chemotherapeutic agent selected from the group consisting of cisplatin, carboplatin, topotecan, irinotecan, bevacizumab, erlotinib, lapatinib, and pemetrexed.

In other embodiments of the compositions, methods, uses, pharmaceutical compositions, combinations, or kits described herein, pharmaceutically acceptable salts of the conjugates described herein are described. Pharmaceutically acceptable salts of the conjugates described herein include the acid addition and base salts thereof.

Suitable acid addition salts are formed from acids which form non-toxic salts. Illustrative examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts of the conjugates described herein are formed from bases which form non-toxic salts. Illustrative examples include the arginine, benzathine, calcium, choline, diethylamine, diolamine, glycine, lysine, magnesium, meglumine, olamine, potassium, sodium, tromethamine and zinc salts. Hemi-salts of acids and bases may also be formed, for example, hemi-sulphate and hemi-calcium salts.

In one embodiment, the conjugates or additional chemotherapeutic agents described herein may be administered as a formulation in association with one or more pharmaceutically acceptable carriers. The carriers can be excipients. The choice of carrier will to a large extent depend on factors such as the particular mode of administration, the effect of the carrier on solubility and stability, and the nature of the dosage form. Pharmaceutical compositions suitable for the delivery of conjugates or additional chemotherapeutic agents described herein and methods for their preparation will be readily apparent to those skilled in the art. Such compositions and methods for their preparation may be found, for example, in Remington: The Science & Practice of Pharmacy, 21st Edition (Lippincott Williams & Wilkins, 2005), incorporated herein by reference.

In one illustrative aspect, a pharmaceutically acceptable carrier includes any and all solvents, dispersion media, coatings, antibacterial and antifungal agents, isotonic and absorption delaying agents, and the like, and combinations thereof, that are physiologically compatible. In some embodiments, the carrier is suitable for parenteral administration. Pharmaceutically acceptable carriers include sterile aqueous solutions or dispersions and sterile powders for the extemporaneous preparation of sterile injectable solutions or dispersions. Supplementary active compounds can also be incorporated into compositions of the invention.

In various embodiments, liquid formulations may include suspensions and solutions. Such formulations may comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

In one embodiment, an aqueous suspension may contain the active materials in admixture with appropriate excipients. Such excipients are suspending agents, for example, sodium carboxymethylcellulose, methylcellulose, hydroxypropylmethylcellulose, sodium alginate, polyvinylpyrrolidone, gum tragacanth and gum acacia; dispersing or wetting agents which may be a naturally-occurring phosphatide, for example, lecithin; a condensation product of an alkylene oxide with a fatty acid, for example, polyoxyethylene stearate; a condensation product of ethylene oxide with a long chain aliphatic alcohol, for example, heptadecaethyleneoxycetanol; a condensation product of ethylene oxide with a partial ester derived from fatty acids and a hexitol such as polyoxyethylene sorbitol monooleate; or a condensation product of ethylene oxide with a partial ester derived from fatty acids and hexitol anhydrides, for example, polyoxyethylene sorbitan monooleate. The aqueous suspensions may also contain one or more preservatives, for example, ascorbic acid, ethyl, n-propyl, or p-hydroxybenzoate; or one or more coloring agents.

In one illustrative embodiment, dispersible powders and granules suitable for preparation of an aqueous suspension by the addition of water provide the active ingredient in admixture with a dispersing or wetting agent, suspending agent and one or more preservatives. Additional excipients, for example, coloring agents, may also be present.

Suitable emulsifying agents may be naturally-occurring gums, for example, gum acacia or gum tragacanth; naturally-occurring phosphatides, for example, soybean lecithin; and esters including partial esters derived from fatty acids and hexitol anhydrides, for example, sorbitan mono-oleate, and condensation products of the said partial esters with ethylene oxide, for example, polyoxyethylene sorbitan monooleate.

In other embodiments, isotonic agents, for example, sugars, polyalcohols such as mannitol, sorbitol, or sodium chloride can be included in the composition. Prolonged absorption of the injectable compositions can be brought about by including in the composition an agent which delays absorption, for example, monostearate salts and gelatin.

In one aspect, a conjugate or additional chemotherapeutic agent as described herein may be administered directly into the blood stream, into muscle, or into an internal organ. Suitable routes for such parenteral administration include intravenous, intraarterial, intraperitoneal, intrathecal, epidural, intracerebroventricular, intraurethral, intrasternal, intracranial, intratumoral, intramuscular and subcutaneous delivery.

Suitable means for parenteral administration include needle (including microneedle) injectors, needle-free injectors and infusion techniques.

In one illustrative aspect, parenteral formulations are typically aqueous solutions which may contain carriers or excipients such as salts, carbohydrates and buffering agents (preferably at a pH of from 3 to 9), but, for some applications, they may be more suitably formulated as a sterile non-aqueous solution or as a dried form to be used in conjunction with a suitable vehicle such as sterile, pyrogen-free water. In other embodiments, any of the liquid formulations described herein may be adapted for parenteral administration of the conjugates or additional chemotherapeutic agents described herein. The preparation of parenteral formulations under sterile conditions, for example, by lyophilization under sterile conditions, may readily be accomplished using standard pharmaceutical techniques well-known to those skilled in the art. EC145, for example, can be lyophilized by the method described in U.S. Appl. Ser. No. 61/474,428, incorporated herein by reference. In another embodiment, the EC145 can be present as a reconstitutable lyophilizate. In one embodiment, the solubility of a conjugate or additional chemotherapeutic agent used in the preparation of a parenteral formulation may be increased by the use of appropriate formulation techniques, such as the incorporation of solubility-enhancing agents. EC145 formulations are described in U.S. Appl. Ser. No. 61/474,428, PCT/US11/037,134, and WO 2011/014821, each incorporated herein by reference in its entirety.

In various embodiments, formulations for parenteral administration may be formulated for immediate and/or modified release. In one illustrative aspect, active agents of the invention may be administered in a time release formulation, for example in a composition which includes a slow release polymer. The active compounds can be prepared with carriers that will protect the compound against rapid release, such as a controlled release formulations, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PGLA). Methods for the preparation of such formulations are generally known to those skilled in the art. In another embodiment, the conjugates or additional chemotherapeutic agents described herein or compositions comprising the conjugates or additional chemotherapeutic agents may be continuously administered, where appropriate.

In one embodiment, a kit is provided. If a combination of active compounds is to be administered, two or more pharmaceutical compositions may be combined in the form of a kit suitable for sequential administration or co-administration of the compositions. Such a kit comprises two or more separate pharmaceutical compositions, at least one of which contains a conjugate described herein, and means for separately retaining the compositions, such as a container, divided bottle, or divided foil packet. In another embodiment, compositions comprising the conjugate or additional chemotherapeutic agent described herein, in a container having a label that provides instructions for use of the conjugate treatment are provided. Instructions are also provided for use of the additional chemotherapeutic agent to be administered (e.g., cisplatin, carboplatin, topotecan, irinotecan, bevacizumab, erlotinib, lapatinib, or pemetrexed, or combinations thereof).

In one embodiment, sterile injectable solutions can be prepared by incorporating the active agent in the required amount in an appropriate solvent with one or a combination of ingredients described above, as required, followed by sterile filtration. Typically, dispersions are prepared by incorporating the active compound into a sterile vehicle which contains a dispersion medium and any additional ingredients from those described above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof, or the ingredients may be sterile-filtered together.

The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. In one embodiment, the proper fluidity can be maintained, for example, by the use of a coating such as lecithin, by the maintenance of the required particle size in the case of dispersion and by the use of surfactants.

Any effective regimen for administering the EC145 and the additional chemotherapeutic agent can be used. For example, the EC145 and the additional chemotherapeutic agent (i.e., drug) can be administered as single doses, or can be divided and administered as a multiple-dose daily regimen. Further, a staggered regimen, for example, one to five days per week can be used as an alternative to daily treatment, and for the purpose of the methods described herein, such intermittent or staggered daily regimen is considered to be equivalent to every day treatment and is contemplated. In one illustrative embodiment the patient is treated with multiple injections of the EC145 and the additional chemotherapeutic agent to eliminate the tumor. In one embodiment, the patient is injected multiple times (preferably about 2 up to about 50 times) with the EC145 and the additional chemotherapeutic agent, for example, at 12-72 hour intervals or at 48-72 hour intervals. Additional injections of the EC145 and the additional drug can be administered to the patient at an interval of days or months after the initial injections(s) and the additional injections can prevent recurrence of the cancer. In another embodiment, the regimen for the additional chemotherapeutic agent is different than for EC145.

The unitary daily dosage of the EC145 and the additional chemotherapeutic agent can vary significantly depending on the patient condition, the disease state being treated, the purity of the compounds and their route of administration and tissue distribution, and the possibility of co-usage of other therapeutic treatments, such as radiation therapy. The effective amount to be administered to a patient is based on body surface area, mass, and physician assessment of patient condition. Effective doses can range, for example, from about 1 ng/kg to about 1 mg/kg, from about 1 μg/kg to about 500 μg/kg, and from about 1 μg/kg to about 100 μg/kg. These doses are based on an average patient weight of about 70 kg, and the kg are kg of patient body weight (mass).

The EC145 and the additional chemotherapeutic agent can each be administered in a dose of from about 1.0 ng/kg to about 1000 μg/kg, from about 10 ng/kg to about 1000 μg/kg, from about 50 ng/kg to about 1000 μg/kg, from about 100 ng/kg to about 1000 μg/kg, from about 500 ng/kg to about 1000 μg/kg, from about 1 ng/kg to about 500 μg/kg, from about 1 ng/kg to about 100 μg/kg, from about 1 μg/kg to about 50 μg/kg, from about 1 μg/kg to about 10 μg/kg, from about 5 μg/kg to about 500 μg/kg, from about 10 μg/kg to about 100 μg/kg, from about 20 μg/kg to about 200 μg/kg, from about 10 μg/kg to about 500 μg/kg, or from about 50 μg/kg to about 500 μg/kg. The total dose may be administered in single or divided doses and may, at the physician's discretion, fall outside of the typical range given herein. These dosages are based on an average patient weight of about 70 kg and the "kg" are kilograms of patient body weight. The physician will readily be able to determine doses for subjects whose weight falls outside this range, such as infants and the elderly.

In another embodiment, the EC145 and the additional chemotherapeutic agent can each be administered in a dose of from about 1 μg/$m^2$ to about 500 mg/$m^2$, from about 1 μg/$m^2$ to about 300 mg/$m^2$, or from about 100 μg/$m^2$ to about 200 mg/$m^2$. In other embodiments, the EC145 and the additional drug can each be administered in a dose of from about 1 mg/$m^2$ to about 500 mg/$m^2$, from about 1 mg/$m^2$ to about 300 mg/$m^2$, from about 1 mg/$m^2$ to about 200 mg/$m^2$, from about 1 mg/$m^2$ to about 100 mg/$m^2$, from about 1 mg/$m^2$ to about 50 mg/$m^2$, or from about 1 mg/$m^2$ to about 600 mg/$m^2$. The total dose may be administered in single or divided doses and may, at the physician's discretion, fall outside of the typical range given herein. These dosages are based on $m^2$ of body surface area.

The conjugates and chemotherapeutic agents described herein may contain one or more chiral centers, or may otherwise be capable of existing as multiple stereoisomers. Accordingly, it is to be understood that the present invention includes pure stereoisomers as well as mixtures of stereoisomers, such as enantiomers, diastereomers, and enantiomerically or diastereomerically enriched mixtures. The conjugates and chemotherapeutic agents described herein may be capable of existing as geometric isomers. Accordingly, it is to be understood that the present invention includes pure geometric isomers or mixtures of geometric isomers.

It is appreciated that the conjugates and chemotherapeutic agents described herein may exist in unsolvated forms as well as solvated forms, including hydrated forms. In general, the solvated forms are equivalent to unsolvated forms and are encompassed within the scope of the present invention. The conjugates and chemotherapeutic agents described herein may exist in multiple crystalline or amorphous forms. In general, all physical forms are equivalent for the uses contemplated by the present invention and are intended to be within the scope of the present invention.

In another embodiment, compositions and/or dosage forms for administration of EC145 or the additional chemotherapeutic agent are prepared from compounds with a purity of at least about 90%, or about 95%, or about 96%, or about 97%, or about 98%, or about 99%, or about 99.5%. In another embodiment, compositions and or dosage forms for administration of EC145 or the additional drug are prepared from compounds with a purity of at least 90%, or 95%, or 96%, or 97%, or 98%, or 99%, or 99.5%.

As used herein, purity determinations may be based on weight percentage, mole percentage, and the like. In addition, purity determinations may be based on the absence or substantial absence of certain predetermined components, such as, but not limited to, folic acid, disulfide containing components not containing a vinca drug, oxidation products, disulfide components not containing a folate, and the like. It is also to be understood that purity determinations are applicable to solutions of the compounds and compositions purified by the methods described herein. In those instances, purity measurements, including weight percentage and mole percentage measurements, are related to the components of the solution exclusive of the solvent. In another embodiment, the EC145 is provided in a sterile container or package.

The purity of the EC145 or the additional drug may be measured using any conventional technique, including various chromatography or spectroscopic techniques, such as high pressure or high performance liquid chromatography (HPLC), nuclear magnetic resonance spectroscopy, TLC, UV absorbance spectroscopy, fluorescence spectroscopy, and the like.

Surface-expressed vitamin receptors, such as the high-affinity folate receptor, are overexpressed on cancer cells. Epithelial cancers of the ovary, mammary gland, colon, lung, nose, throat, and brain have all been reported to express elevated levels of the folate receptor. In fact, greater than 90% of all human ovarian tumors are known to express large amounts of this receptor. Accordingly, the combination therapy described herein can be used to treat a variety of tumor cell types.

The therapy described herein, can be used for both human clinical medicine and veterinary applications. Thus, the host animal harboring the population of pathogenic cells and treated with the combination therapy can be human (i.e., a patient) or, in the case of veterinary applications, can be a laboratory, agricultural, domestic, or wild animal. The methods described herein can be applied to humans, laboratory animals such rodents (e.g., mice, rats, hamsters, etc.), rabbits, monkeys, chimpanzees, domestic animals such as dogs, cats, and rabbits, agricultural animals such as cows, horses, pigs, sheep, goats, and wild animals in captivity such as bears, pandas, lions, tigers, leopards, elephants, zebras, giraffes, gorillas, dolphins, and whales.

In one aspect, the response to treatment is characterized utilizing Response Evaluation Criteria in Solid Tumors (RECIST) criteria. Illustratively, the criteria have been adapted from the original *WHO Handbook* (3), taking into account the measurement of the longest diameter for all target lesions: complete response, (CR) —the disappearance of all target lesions; partial response (PR) —at least a 30% decrease in the sum of the longest diameter of target lesions, taking as reference the baseline sum longest diameter; stable disease (SD) —neither sufficient shrinkage to qualify for PR nor sufficient increase to qualify for PD, taking as reference the smallest sum longest diameter since the treatment started; progressive disease (PD) —at least a 20% increase in the sum of the longest diameter of target lesions, taking as reference the smallest sum longest diameter recorded since the treatment started or the appearance of one or more new lesions. Other criteria include overall tumor response rate (ORR=CR+PR), disease control rate (DCR=CR+PR+SD), and overall survival (OS) —the time to death for a given patient defined as the number of days from the first day the patient received protocol treatment to the date of the patient's death.

In one embodiment there is provided a method of treatment of a folate receptor expressing epithelial tumor in a patient in need thereof comprising administering a therapeutically effective amount of EC145 in combination with a therapeutically effective amount of the additional chemotherapeutic agent. The EC145 and the additional chemotherapeutic agent can be administered simultaneously in one or multiple compositions, or sequentially. Another embodiment is the use of EC145 in combination with the additional chemotherapeutic agent for the treatment of a folate receptor expressing epithelial tumor in a patient. A further embodiment is the use of EC145 for the manufacture of a medicament for the treatment in combination with the additional chemotherapeutic agent of a folate receptor expressing epithelial tumor in a patient.

For any of the methods, uses, compositions, pharmaceutical compositions, combinations, or kits described herein, an embodiment of a folate receptor expressing epithelial tumor is an ovarian, endometrial or non-small cell lung (NSCLC) tumor. The treatment of NSCLC can occur at any stage including stage 0, I, II, IIIA, IIIB, or IV. For any of the above methods, uses, compositions, pharmaceutical compositions, combinations, or kits, another embodiment of a folate receptor expressing epithelial tumor is an ovarian tumor. The ovarian tumor can be platinum-resistant or platinum-sensitive.

In another embodiment for any methods, uses, compositions, pharmaceutical compositions, combinations, or kits, the EC145 is a compound having the formula

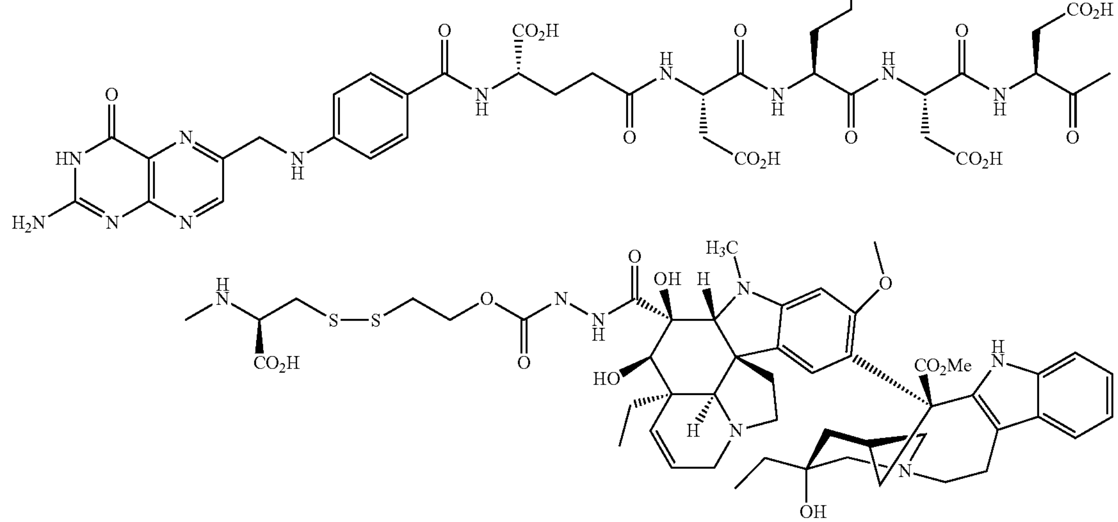

or a pharmaceutically acceptable salt thereof.

As used herein, EC145 may be present in solution or suspension in an ionized form, including a protonated form.

In one embodiment, there is provided a method of treatment of platinum-resistant ovarian cancer in a patient in need thereof comprising administering a therapeutically effective amount of EC145 in combination with a therapeutically effective amount of the additional chemotherapeutic agent. In another embodiment, there is provided use of EC145 in combination with the additional chemotherapeutic agent for the treatment of platinum-resistant ovarian cancer in a patient. In another embodiment, there is provided the use of EC145 for the manufacture of a medicament for the treatment in combination with the additional chemotherapeutic agent of platinum-resistant ovarian cancer in a patient.

For any method, use, pharmaceutical composition, composition, combination, or kit described above concerning the treatment of platinum-resistant ovarian cancer using EC145 in combination with the additional chemotherapeutic agent, one embodiment is one wherein the purity of EC145 or the additional drug is at least 90%. Another embodiment is one wherein the EC145 or the additional chemotherapeutic agent is provided in an aqueous sterile liquid formulation.

In another embodiment, a method of selecting a patient for treatment is described wherein the method comprises the step of administering to the patient a composition comprising EC20 combined with an isotope of technetium as described in PCT/US2010/043992 (the EC20 structure is described in PCT/US2010/043992, now published as WO 2011/014821), the disclosure of which is incorporated by reference herein in its entirety, wherein patients are selected for therapy if they express the folate receptor to levels of at least FR+ (i.e., at least one lesion expresses the folate receptor) or FR++ (i.e., all lesions express the folate receptor). In one embodiment of this imaging procedure, the patient is injected with 0.5 mg of folic acid, followed within 1 to 3 minutes by a 1 to 2 mL injection of 0.1 mg of EC20 labeled with 20 to 25 mCi of $^{99m}$Tc and imaging is performed 1 to 2 hours later. In one embodiment, the imaging methods are selected from the group consisting of planar, SPECT, and SPECT/CT imaging.

In another embodiment, the methods, uses, compositions, pharmaceutical compositions, combinations, or kits described herein include the following examples. The examples further illustrate additional features of the various embodiments of the invention described herein. However, it is to be understood that the examples are illustrative and are not to be construed as limiting other embodiments of the invention described herein. In addition, it is appreciated that other variations of the examples are included in the various embodiments of the invention described herein.

EXAMPLES

Materials $N^{10}$-trifluoroacetylpteroic acid was purchased from Eprova A G, Schaffhausen, Switzerland. Peptide synthesis reagents were purchased from NovaBiochem and Bachem. Cellulose plates and DEAE ion exchange plates were purchased from J. T. Baker. DOXIL® was obtained from Ortho Biotech Products, LP, Raritan, N.J. Pemetrexed disodium, Topotecan HCl, Erlotinib HCl, Irinotecan HCl, and Topotecan HCL were purchased from A. K. Scientific (Mountain View, Calif.). Cisplatin and carboplatin were purchased from Sigma (St. Louis. MO). Gemzar was purchased from Purdue Pharmacy (West Lafayette, Ind.)

Methods

Cell Growth Inhibition Studies

Figure 48:
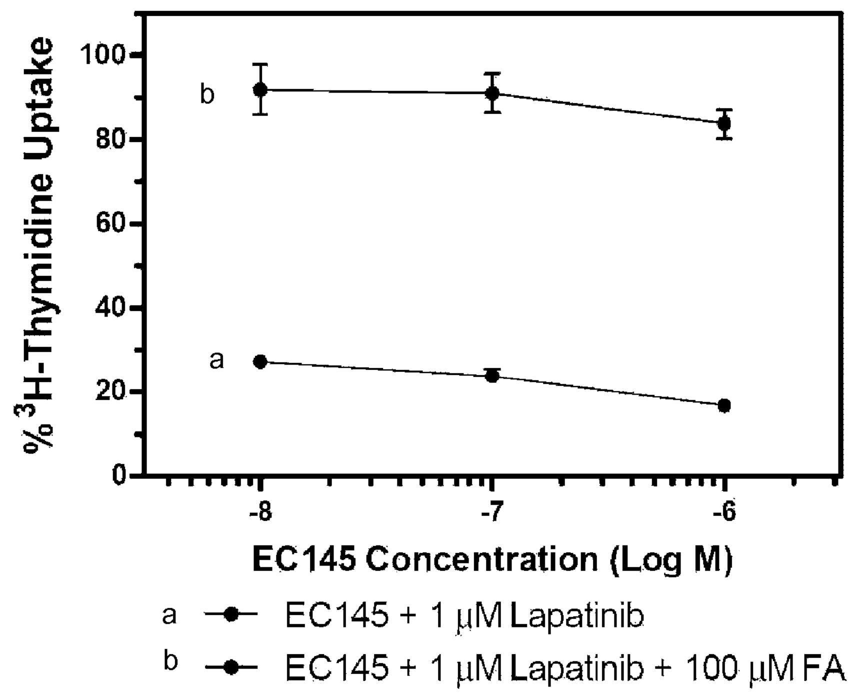
FIG. 48. Treatment of EC145 resistant KB-DR300 tumor cells with (a) EC145+1 mM Lapatinib or (b) EC145+1 μM Lapatinib+100 μM folic acid. It is believed that lapatinib blocks pgp efflux of DALVBH from the KB-DR200 cells.
Figure 49:
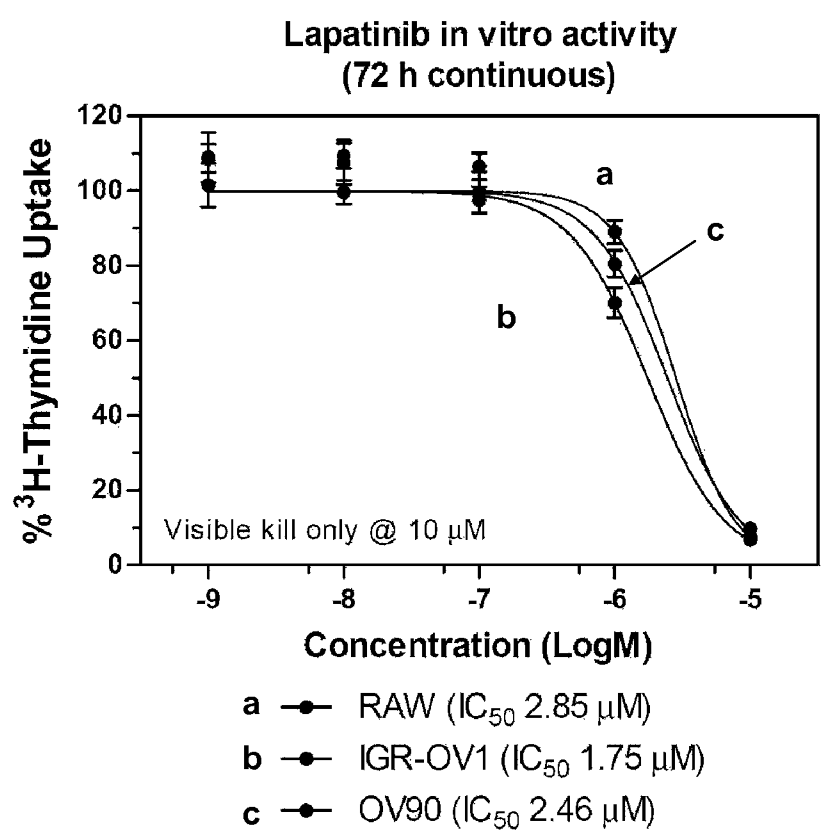
FIG. 49. Lapatinib is has little activity against three cell lines (a) RAW cells ($IC_{50}$ 2.85 μM), (b) IGR-OV1 cells ($IC_{50}$ 1.75 μM), and OV90 cells ($IC_{50}$ 2.46 μM).
Figures 50, 51:
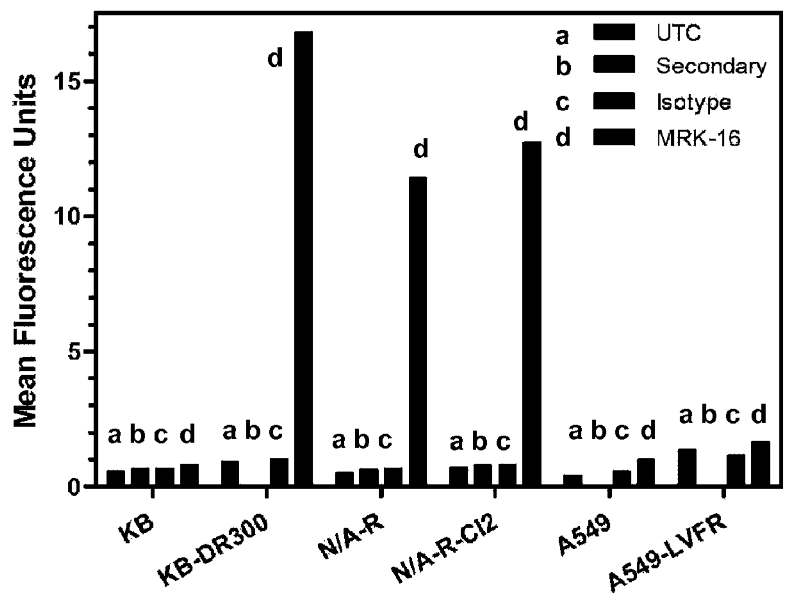
FIG. 50. Vinca alkaloid-resistant KB-DR300, NCI/ADR, and NCI.ADR-C12 have high pgp expression. MRD-16 recognizes an external pgp epitope. MRK-16 (α-P-gp) FACS analysis on KB-DR300, NCI/ADR, and NCI.ADR-C12 cell lines.
FIG. 51. Co-treating vinca resistant cell lines (NCI/ADR-c12 and KB-DR300) with lapatinib and EC145 increases the activity of EC145. The activity of EC145 on non-resistant cells (KB tumor cells) appears to be unaffected by the addition of lapatinib.
Figure 52:
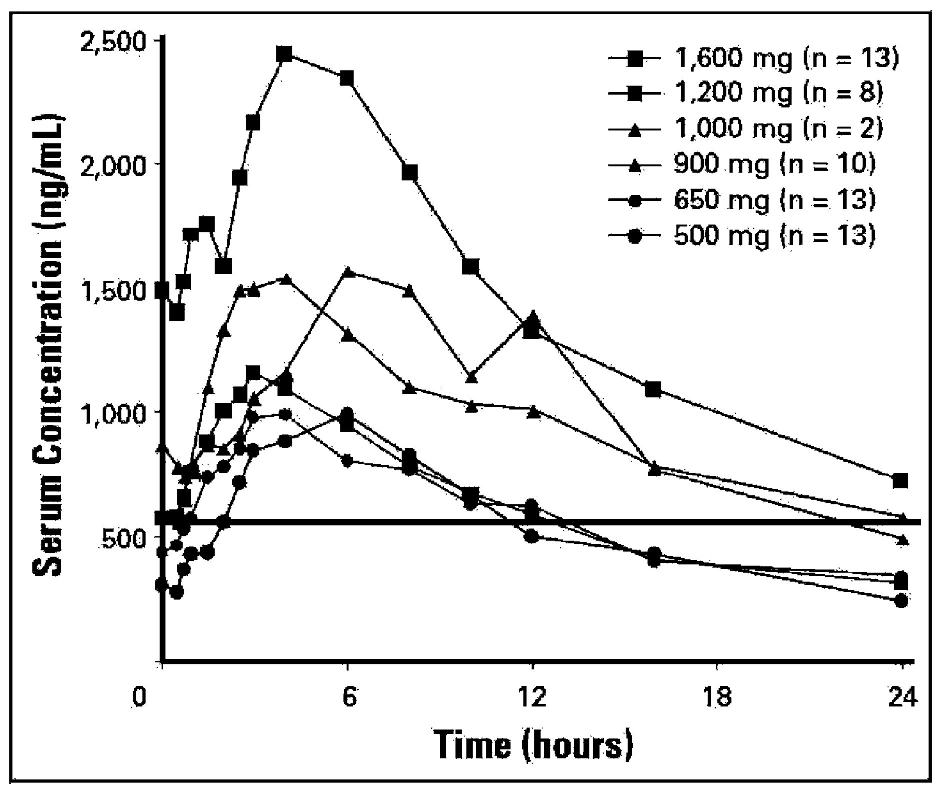
FIG. 52. Median steady state serum concentration profiles for several daily doses of lapatinib. Synergy appears at human plasma steady state lapatinib concentrations of about 1 μM.
Figure 53:
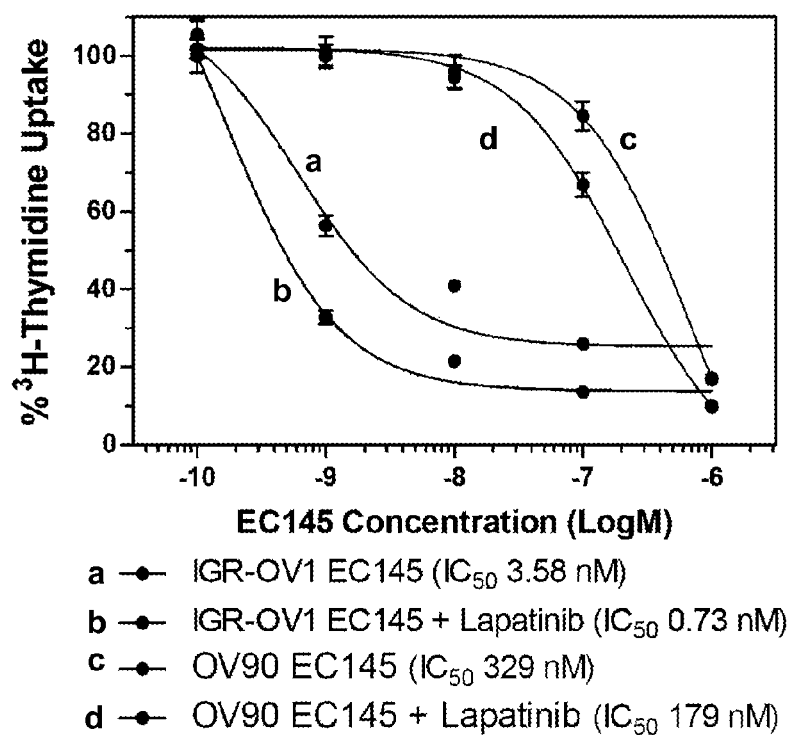
FIG. 53. Lapatinib increases EC145 activity in IGR-OV1 and OV90 tumor cells. (a) IGR-OV1 cells treated with EC145 ($IC_{50}$ 3.58 nM), (b) IGR-OV1 cell treated with EC145+Lapatinib ($IC_{50}$ 0.73 nM), (c) OV90 cells treated with EC145 ($IC_{50}$ 329 nM), and (d) OV90 cells treated with EC145+Lapatinib ($IC_{50}$ 179 nM)

Exponentially growing KB or J6456 cells were seeded in 24-well plates 24 h before treatment with drugs. Cells were exposed to graded concentrations (four replicates) of EC145 (or vindesine or DAVLBH) or combination drug (doxorubicin) either alone or in combination. Cells receiving EC145 or EC145+doxorubicin were pulsed for 2 h at 37° C., rinsed 4 times with 0.5 mL of medium and then chased in 1 mL of fresh medium or fresh medium+doxorubicin up to 72 h. Cells treated with vindesine, DAVLBH or doxorubicin alone were treated for 72 h. A total of five drug concentrations for each drug plus a drug-free control were evaluated. Cells were then treated with fresh medium containing $^3$H-thymidine for 2 h at 37° C. Cells were further washed with PBS and treated with ice-cold 5% trichloroacetic acid. After 15 min, the trichloroacetic acid was aspirated and the cells solubilized by the addition of 0.25 N sodium hydroxide for 15 min at room temperature. Each solubilized sample was transferred to scintillation vials containing Ecolume scintillation cocktail and counted in a liquid scintillation counter. Chemosensitivity values were expressed as the drug concentration that inhibited cell growth by 80% ($IC_{80}$) determined from concentration-effect relationships using GraphPad prism. The same general protocol was followed to measure the in vitro activity of lapatinib on several cell lines (see FIGS. 48 and 49) and the in vitro activity of a combination of EC145 with lapatinib on IGR-OV1 and OV90 cells (see FIG. 53). The same general protocol was used to measure the cytotoxity of EC145 in the presence or absence of lapatinib on several cell lines that are resistant to DAVLBH and EC145 (see FIG. 51).

In Vivo Antitumor Experiments.

Four to six week-old female nu/nu mice (Charles River, Wilmington, Mass.) or six to seven week-old female Balb/c mice (Harlan Sprague Dawley, Inc., Indianapolis, Ind.) or four to six week-old female DBA mice (Harlan Sprague Dawley, Inc., Indianapolis, Ind.) were maintained on a standard 12 h light-dark cycle and fed ad libitum with folate-deficient chow (Harlan diet #TD00434, Harlan Teklad, Madison, Wis.) for the duration of the experiment. FR-positive human nasopharyngeal KB cells, human ovarian IGR-OV1 cells, human ovarian OV90 cells and syngeneic mouse lymphocytic leukemia L1210 cells were grown continuously as a monolayer, using folate-free RPMI medium (FFRPMI) containing 10% heat-inactivated fetal calf serum (HIFCS) at 37° C. in a 5% $CO_2$/95% air-humidified atmosphere with no antibiotics. Syngeneic FR-positive Madison 109 (M109) lung carcinoma cells were generated from M109 tumors and cultured for a few days in FFRPMI containing 10% HIFCS for a few days before implantation in mice. KB cells ($1\times10^6$ per nu/nu mouse), M109 cells ($1\times10^6$ per Balb/c mouse), IGR-OV1 cells ($4\times10^6$ per nu/nu mouse) or OV90 cells ($1\times10^6$ per nu/nu mouse) or L1210 cells ($2\times10^5$ per DBA mouse) in 100 μL were injected in the subcutis of the dorsal medial area. Mice were divided into groups of five, and test articles were freshly prepared and injected through the lateral tail vein under sterile conditions in a volume of 200 μL of phosphate-buffered saline (PBS). Intravenous (i.v.) treatments were typically initiated when the tumors were approximately 100-200 mm$^3$ in volume. The mice in the control groups received no treatment. Growth of each s.c. tumor was followed by measuring the tumor three times per week during treatment and twice per week thereafter until a volume of 1500 mm$^3$ was reached. Tumors were measured in two perpendicular directions using Vernier calipers, and their volumes were calculated as $0.5\times L\times W^2$, where L=measurement of longest axis in mm and W=measurement of axis perpendicular to L in mm. As a general measure of toxicity, changes in body weights were determined on the same schedule as tumor volume measurements. Survival of animals was monitored daily. Animals that were moribund (or unable to reach food or water) were euthanized by $CO_2$ asphyxiation. All in vivo studies were performed in accordance with the American Accreditation Association of Laboratory Animal Care guidelines.

For individual tumors, a partial response (PR) was defined as volume regression >50% but with measurable tumor (>2 mm$^3$) remaining at all times. Complete response (CR) was defined as a disappearance of measurable tumor mass (<2 mm$^3$) at some point until the end of the study. A cure was defined as a CR without tumor re-growth within the study time frame.

Analysis of Combined Drug Effects

Drug synergy was determined by the isobologram and combination-index methods, derived from the median-effect principle. Data obtained from the growth inhibitory experiments were used to perform these analyses. The isobologram is a graphical representation of the drug interaction and is formed by selecting a desired cell kill fraction (80% in this case) and plotting the individual drug doses required to generate that fraction on their respective x- and y-axes. A straight line is then drawn to connect the points. Multiple combinations of corresponding drug concentrations that achieved the 80% growth inhibition effect are plotted in the isobologram. Combination data points that fall on the line represent an additive drug-drug interaction, whereas data points that fall below or above the line represent synergism or antagonism, respectively. The combination-index method is a quantitative representation of a two-drug interaction. For each combination of drug concentrations (for example: EC145/doxorubicin) [$D_{EC145\ (80)}$, $D_{dooxorubican\ (80)}$], producing in combination the $IC_{80}$ effect, the combination index ($\Sigma FIC_{80}$) was calculated as follows: $\Sigma FIC_{80}=(D_{EC145\ (80)}/IC_{80}$, EC145)+ $D_{doxorubicin\ (80)}/IC_{80}$, doxorubicin), where $IC_{80}$, EC145 and $IC_{80}$, doxorubicin are the concentrations of each individual drug that would produce the $IC_{80}$ effect if given alone. A $\Sigma FIC_{80}$ of 1 indicates an additive effect between two agents, whereas a $\Sigma FIC_{80}<1$ or $\Sigma FIC_{80}>1$ indicates synergism or antagonism, respectively. See FIGS. 7, 18-20, 29-30, 32-39, and 58-59.

Flow Cytometry with MRK-16 (Anti-PGP) Antibody

KB, KB-DR300, N/A-R, N/A-R—C12, A549 Parent & A549-LVFR cells (~$1\times10^6$ cells/sample) were incubated with 10 μg/ml MRK-16 or mouse $IgG_{2a}$ in 1% BSA/PBS for 1 h @ 4° C. Cells were washed twice with 1% BSA/PBS buffer and incubated with 20 μg/ml Alexa Fluor 488 or 1% BSA/PBS (untreated control) for 1 h @ 4° C. Cells were washed with 1% BSA/PBS buffer and fixed in 1% paraformaldehyde for 15 min at room temp. Cells were washed again, resuspended in 1% BSA/PBS, and analyzed on a Beckman Coulter FC-500 Flow cytometer. See FIG. 50.

Example

Combination Therapy of EC145 with Carboplatin

Figure 2:
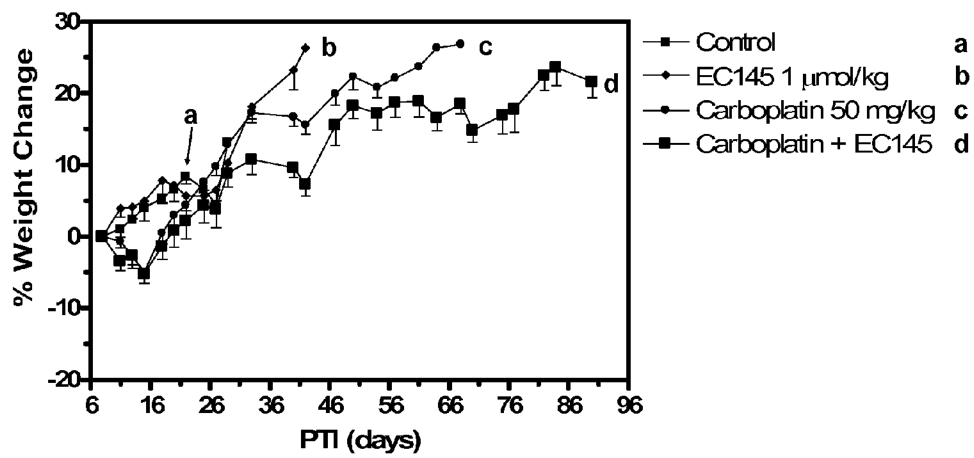
FIG. 2. Percentage weight change (average for the five animals in each treatment group) measured for nu/nu mice with KB tumors (109-188 $mm^3$ range) that were (a) untreated; or treated with either: (b) EC145 at 1 μmol/kg/injection, TIW for 2 weeks; or (c) Carboplatin at 50 mg/kg, TIW for 1 week or (d) EC145 at 1 μmol/kg/injection, TIW for 2 weeks+Carboplatin at 50 mg/kg, TIW for 1 week.

Randomized nu/nu mice with KB tumors (109-188 mm$^3$ range) were (a) untreated; or treated with either: (b) EC145 at 1 μmol/kg/injection, TIW for 2 weeks; or (c) Carboplatin at 50 mg/kg, TIW for 1 week or (d) EC145 at 1 μmol/kg/injection, TIW for 2 weeks+Carboplatin at 50 mg/kg, TIW for 1 week. See FIG. 1 for tumor response and FIG. 2 for weight change during the treatment period. Treatment with Carboplatin alone resulted in 3 partial responses. The combination treatment resulted in 1 complete response and 4 Cures.

Example

Combination Therapy of EC145 with Cisplatin

Figure 3:
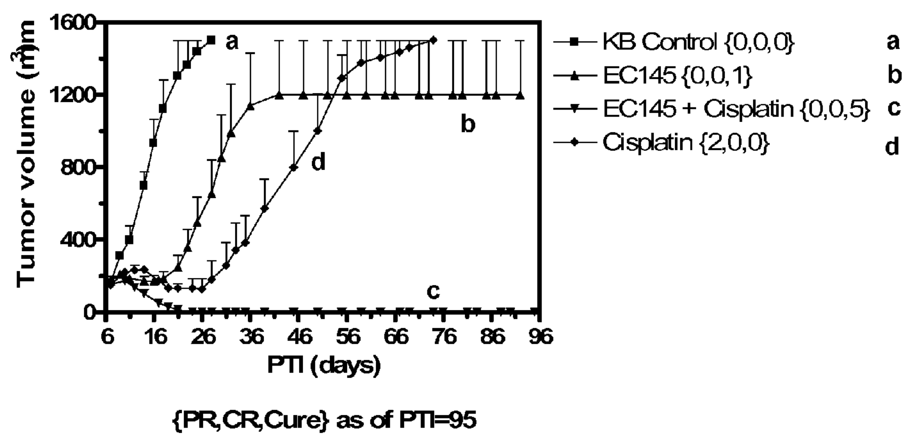
FIG. 3. Tumor volume (average for the five animals in each treatment group) measured for nu/nu mice with KB tumors (120-200 $mm^3$ range) that were (a) untreated; or treated with either: (b) EC145 at 1 μmol/kg/injection, TIW for 2 weeks; or (d) Cisplatin at 3 mg/kg, BIW for 2 weeks or (c) EC145 at 1 μmol/kg/injection, TIW for 2 weeks+Cisplatin at 3 mg/kg, BIW for 2 weeks. Treatment with EC145 alone resulted in 0 partial responses, 0 complete responses, and 1 Cure. Treatment with Cisplatin alone resulted in 2 partial responses. The combination treatment resulted in 5 Cures.
Figure 4:
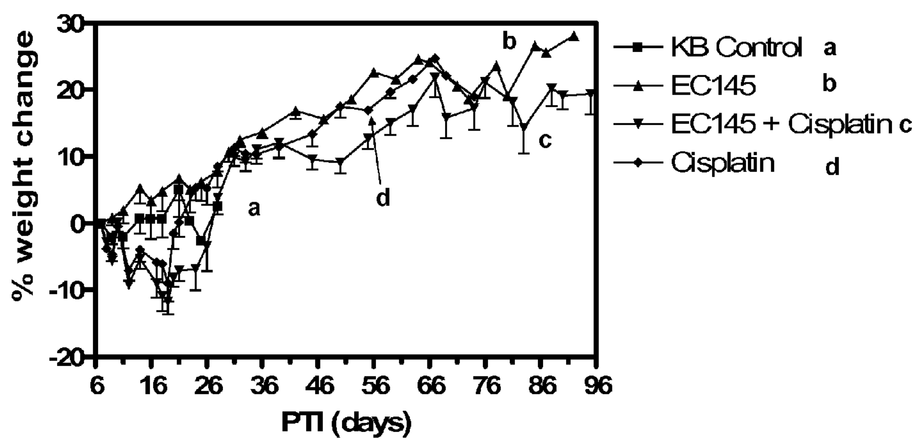
FIG. 4. Percentage weight change (average for the five animals in each treatment group) measured for nu/nu mice with KB tumors (120-200 $mm^3$ range) that were (a) untreated; or treated with either: (b) EC145 at 1 μmol/kg/injection, TIW for 2 weeks; or (d) Cisplatin at 3 mg/kg, BIW for 2 weeks or (c) EC145 at 1 μmol/kg/injection, TIW for 2 weeks+Cisplatin at 3 mg/kg, BIW for 2 weeks.

Randomized nu/nu mice with KB tumors (120-200 mm$^3$ range) were (a) untreated; or treated with either: (b) EC145 at 1 μmol/kg/injection, TIW for 2 weeks; or (d) Cisplatin at 3 mg/kg, BIW for 2 weeks or (c) EC145 at 1 μmol/kg/injection, TIW for 2 weeks+Cisplatin at 3 mg/kg, BIW for 2 weeks. See FIG. 3 for tumor response and FIG. 4 for weight change during the treatment period. Treatment with Cisplatin alone resulted in 2 partial responses. The combination treatment resulted in 5 Cures.

Example

Combination Therapy of EC145 with Topotecan

Figure 5:
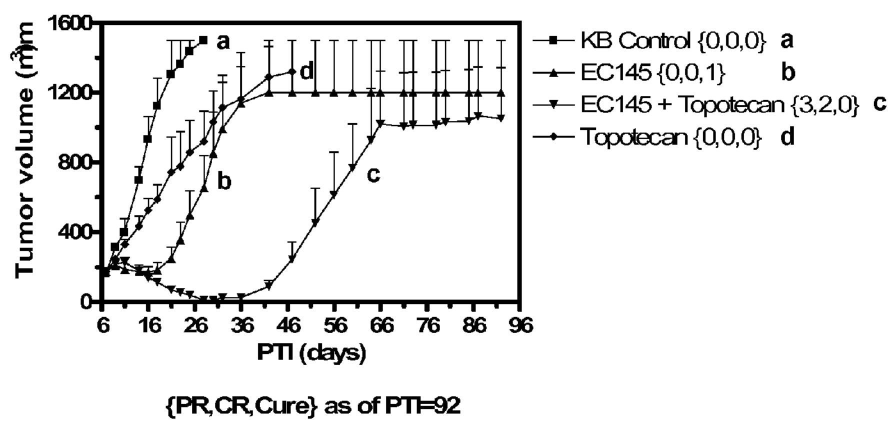
FIG. 5. Tumor volume (average for the five animals in each treatment group) measured for nu/nu mice with KB tumors (144-204 $mm^3$ range) that were (a) untreated; or treated with either: (b) EC145 at 1 μmol/kg/injection, TIW for 2 weeks; or (d) Topotecan at 5 mg/kg, TIW for 2 weeks or (c) EC145 at 1 μmol/kg/injection, TIW for 2 weeks+Topotecan at 5 mg/kg, TIW for 2 weeks. Treatment with EC145 alone resulted in 0 partial responses, 0 complete responses, and 1 Cure. Treatment with Topotecan alone resulted in no partial responses, complete responses, or Cures. The combination treatment resulted in 3 partial responses and 2 complete responses.
Figure 6:
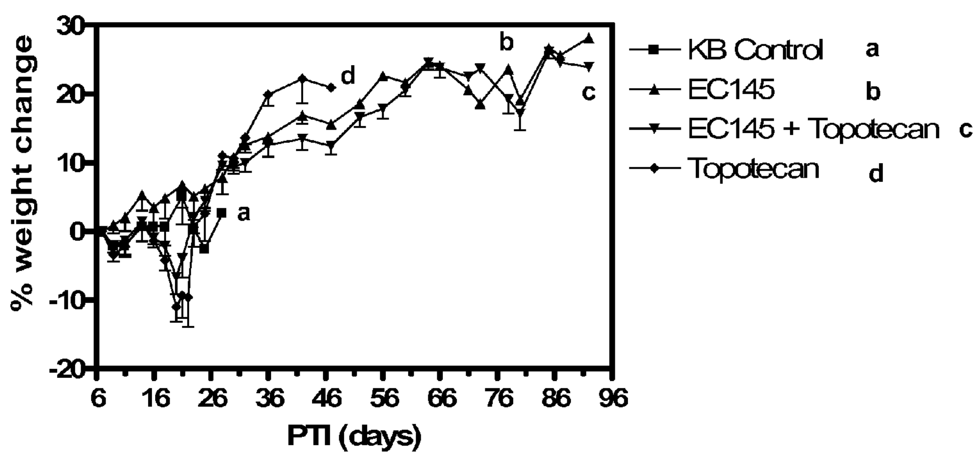
FIG. 6. Percentage weight change (average for the five animals in each treatment group) measured for nu/nu mice with KB tumors (144-204 $mm^3$ range) that were (a) untreated; or treated with either: (b) EC145 at 1 μmol/kg/injection, TIW for 2 weeks; or (d) Topotecan at 5 mg/kg, TIW for 2 weeks or (c) EC145 at 1 μmol/kg/injection, TIW for 2 weeks+Topotecan at 5 mg/kg, TIW for 2 weeks.
Figure 7:
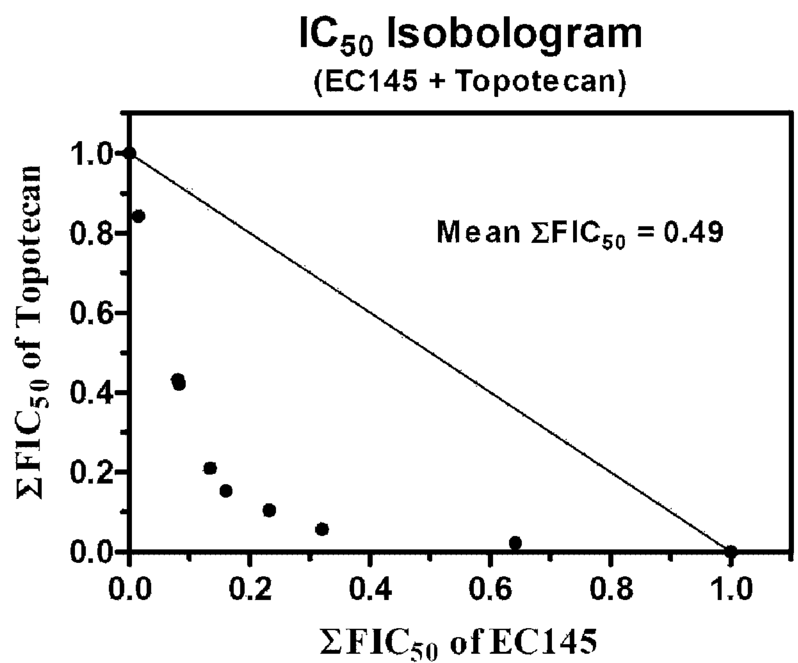
FIG. 7. The isobologram shows that in vitro activity of EC145 and Topotecan are synergistic.

Randomized nu/nu mice with KB tumors (144-204 $mm^3$ range) were (a) untreated; or treated with either: (b) EC145 at 1 μmol/kg/injection, TIW for 2 weeks; or (d) Topotecan at 5 mg/kg, TIW for 2 weeks or (c) EC145 at 1 μmol/kg/injection, TIW for 2 weeks+Topotecan at 5 mg/kg, TIW for 2 weeks. See FIG. 5 for tumor response and FIG. 6 for weight change during the treatment period. Treatment with Topotecan alone resulted in 3 partial responses and 2 complete responses. The combination treatment resulted in 3 partial responses and 2 complete responses.

Example

Combination Therapy of EC145 with DOXIL

Figure 23:
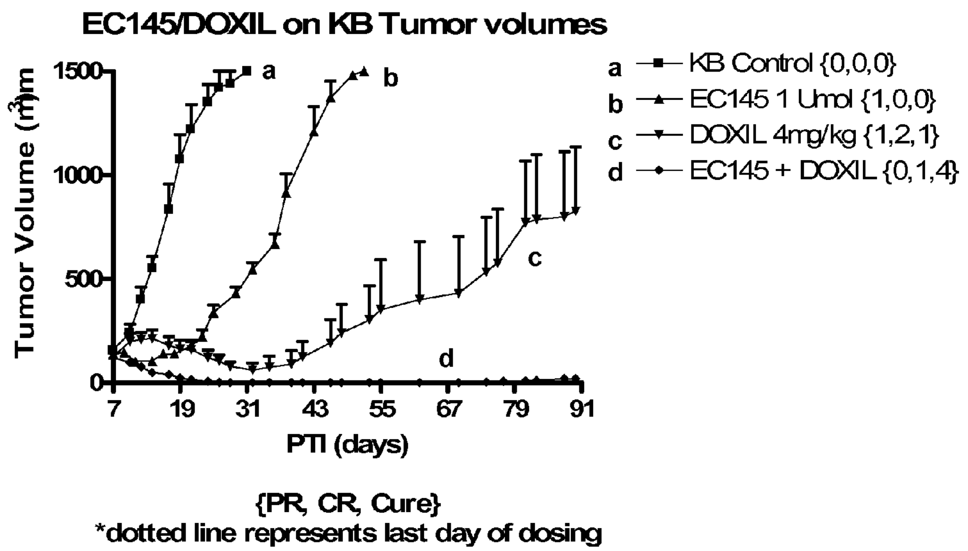
FIG. 23. Tumor volume (average for the five animals in each treatment group) measured for nu/nu mice with KB tumors (114-177 $mm^3$ range) that were (a) untreated; or treated with either: (b) EC145 at 1 μmol/kg/injection, TIW for 2 weeks; or (c) DOXIL at 4 mg/kg, BIW for 2 weeks or (d) EC145 at 1 μmol/kg/injection, TIW for 2 weeks+DOXIL at 4 mg/kg, BIW for 2 weeks. Treatment with EC145 alone resulted in 1 partial response, 0 complete responses, and 0 Cures. Treatment with DOXIL alone resulted in 1 partial response, 2 complete responses, and 1 Cure. The combination treatment resulted in 1 complete response and 4 Cures.
Figure 24:
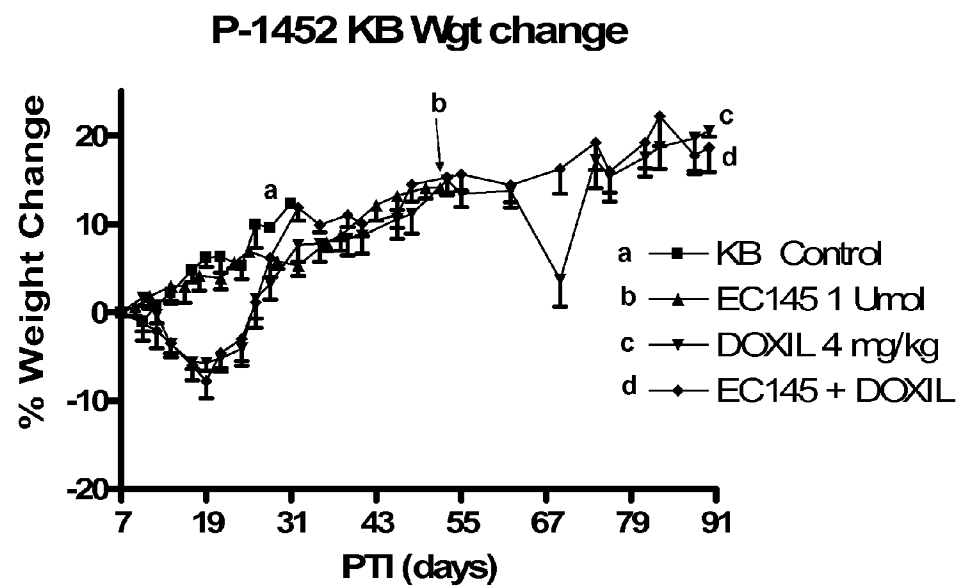
FIG. 24. Percentage weight change (average for the five animals in each treatment group) measured for nu/nu mice with KB tumors (114-177 $mm^3$ range) that were (a) untreated; or treated with either: (b) EC145 at 1 μmol/kg/injection, TIW for 2 weeks; or (c) DOXIL at 4 mg/kg, BIW for 2 weeks or (d) EC145 at 1 μmol/kg/injection, TIW for 2 weeks+DOXIL at 4 mg/kg, BIW for 2 weeks.

Randomized nu/nu mice with KB tumors (114-177 $mm^3$ range) were (a) untreated; or treated with either: (b) EC145 at 1 μmol/kg/injection, TIW for 2 weeks; or (c) DOXIL at 4 mg/kg, BIW for 2 weeks or (d) EC145 at 1 μmol/kg/injection, TIW for 2 weeks+DOXIL at 4 mg/kg, BIW for 2 weeks. See FIG. 23 for tumor response and FIG. 24 for weight change during the treatment period. Treatment with DOXIL alone resulted in 1 partial response, 2 complete responses, and 1 Cure. The combination treatment resulted in 1 complete response and 4 Cures.

Example

Combination Therapy of EC145 with Irinotecan

Figure 10:
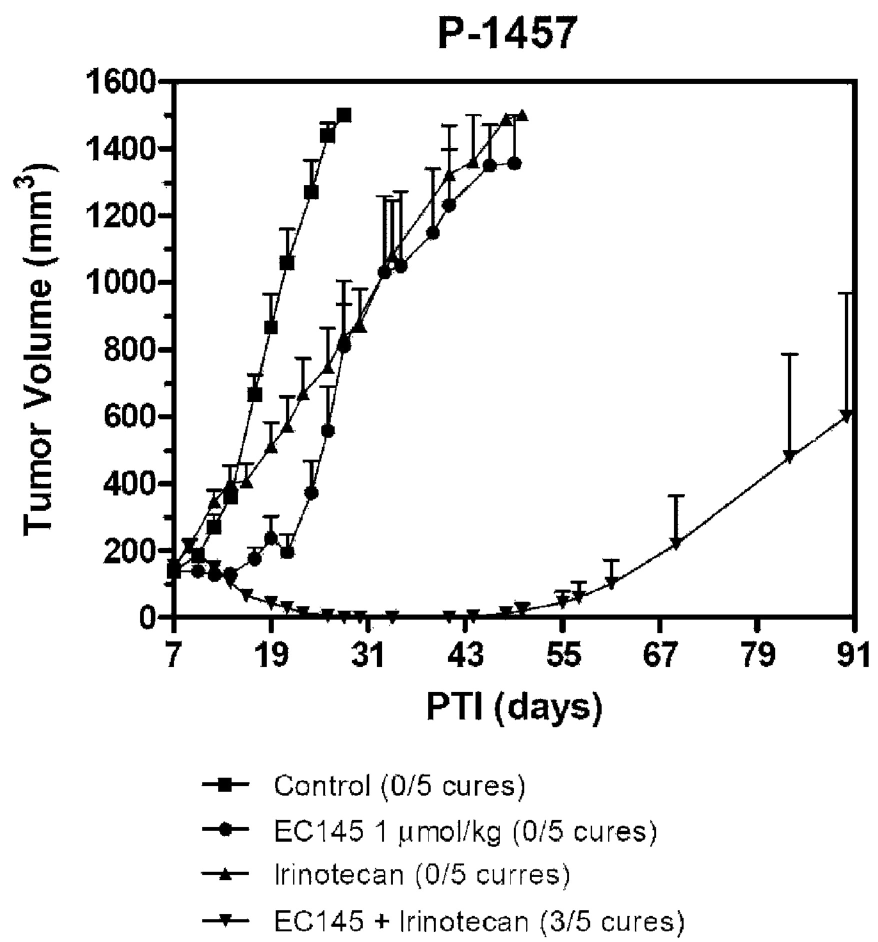
FIG. 10. Tumor volume (average for the five animals in each treatment group) measured for nu/nu mice with KB tumors (114-177 $mm^3$ range) that were (■) untreated; or treated with either: (●) EC145 at 1 μmol/kg/injection, TIW for 2 weeks; or (▲) Irinotecan at 40 mg/kg, BIW for 2 weeks or (▼) EC145 at 1 μmol/kg/injection, TIW for 2 weeks+Irinotecan at 40 mg/kg, BIW for 2 weeks. Treatment with EC145 alone resulted in 0 partial responses, 0 complete responses, and 0 Cures. Treatment with Irinotecan alone resulted in no partial responses, complete responses, or Cures. The combination treatment resulted in 1 complete response and 3 Cures.
Figure 11:
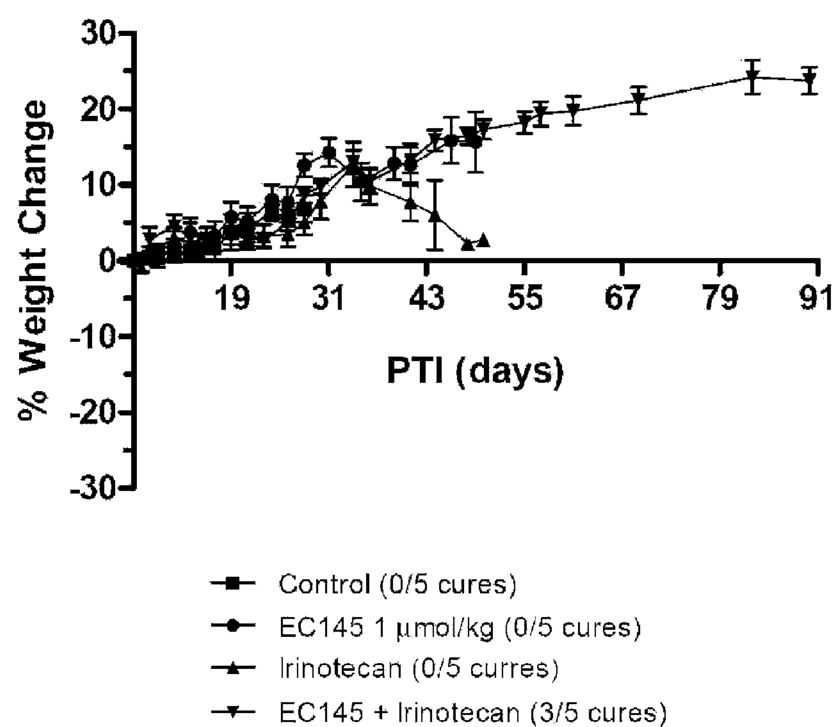
FIG. 11. Percentage weight change (average for the five animals in each treatment group) measured for nu/nu mice with KB tumors (114-177 $mm^3$ range) that were (■) untreated; or treated with either: (●) EC145 at 1 μmol/kg/injection, TIW for 2 weeks; or (▲) Irinotecan at 40 mg/kg, BIW for 2 weeks or (▼) EC145 at 1 μmol/kg/injection, TIW for 2 weeks+Irinotecan at 40 mg/kg, BIW for 2 weeks.

Randomized nu/nu mice with KB tumors (114-177 $mm^3$ range) were (a) untreated; or treated with either: (b) EC145 at 1 μmol/kg/injection, TIW for 2 weeks; or (c) Irinotecan at 40 mg/kg, BIW for 2 weeks or (d) EC145 at 1 μmol/kg/injection, TIW for 2 weeks+Irinotecan at 40 mg/kg, BIW for 2 weeks. See FIG. 10 for tumor response and FIG. 11 for weight change during the treatment period. Treatment with Irinotecan alone resulted in no partial responses, complete responses, or Cures. The combination treatment resulted in 1 complete response and 4 Cures.

Example

Combination Therapy of EC145 with Avastin

Figure 12:
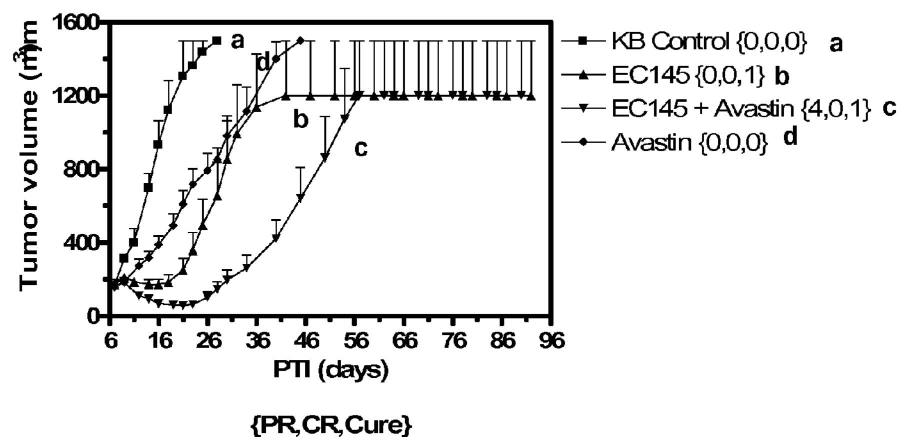
FIG. 12. Tumor volume (average for the five animals in each treatment group) measured for nu/nu mice with KB tumors (108-222 $mm^3$ range) that were (a) untreated; or treated with either: (b) EC145 at 1 μmol/kg/injection, TIW for 2 weeks; or (d) Avastin (i.e. bevacizumab) at 5 mg/kg, BIW for 2 weeks or (c) EC145 at 1 μmol/kg/injection, TIW for 2 weeks+Avastin at 5 mg/kg, BIW for 2 weeks. Treatment with EC145 alone resulted in 0 partial responses, 0 complete responses, and 1 Cure. Treatment with Avastin alone resulted in no partial responses, complete responses, or Cures. The combination treatment resulted in 4 partial responses and 1 Cure.
Figure 13:
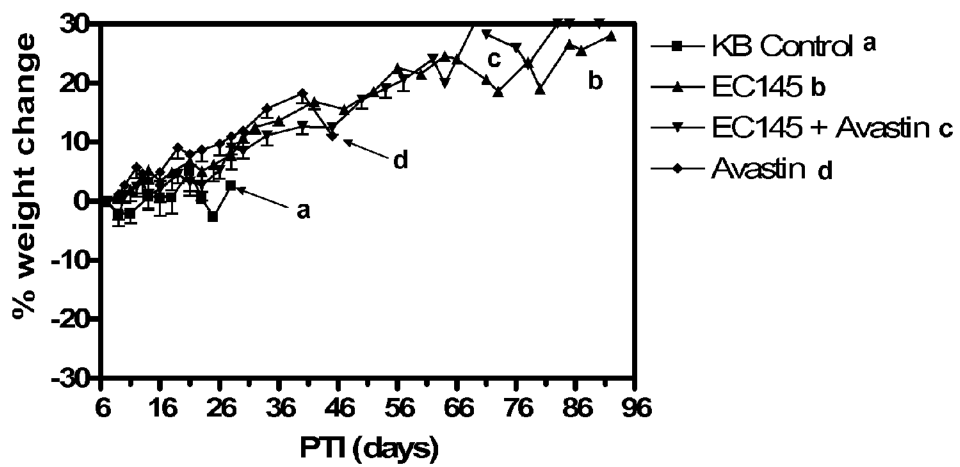
FIG. 13. Percentage weight change (average for the five animals in each treatment group) measured for nu/nu mice with KB tumors (108-222 $mm^3$ range) that were (a) untreated; or treated with either: (b) EC145 at 1 μmol/kg/injection, TIW for 2 weeks; or (d) Avastin at 5 mg/kg, BIW for 2 weeks or (c) EC145 at 1 μmol/kg/injection, TIW for 2 weeks+Avastin at 5 mg/kg, BIW for 2 weeks.

Randomized nu/nu mice with KB tumors (108-222 $mm^3$ range) were (a) untreated; or treated with either: (b) EC145 at 1 μmol/kg/injection, TIW for 2 weeks; or (d) Avastin at 5 mg/kg, BIW for 2 weeks or (c) EC145 at 1 μmol/kg/injection, TIW for 2 weeks+Avastin at 5 mg/kg, BIW for 2 weeks. See FIG. 12 for tumor response and FIG. 13 for weight change during the treatment period. Treatment with Avastin alone resulted in no partial responses, complete responses, or Cures. The combination treatment resulted in 4 partial responses and 1 Cure.

Example

Combination Therapy of EC145 with Gemcitabine

Figure 14:
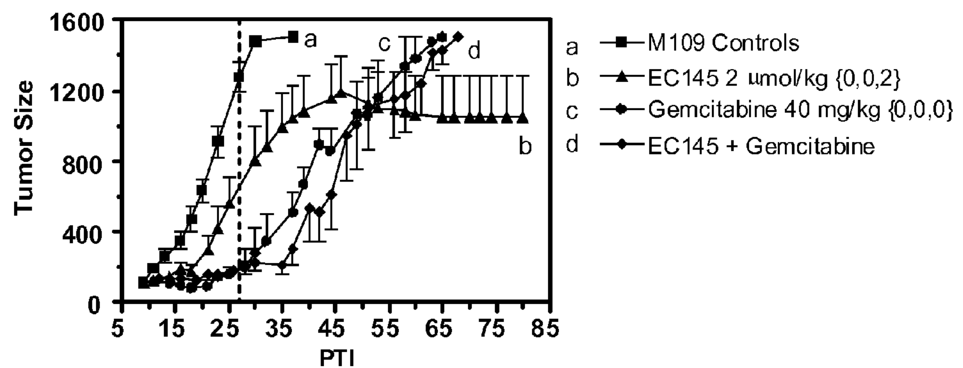
FIG. 14. Tumor volume (average for the five animals in each treatment group) measured for Balb/c mice with M109 tumors (86-149 $mm^3$ range) that were (a) untreated; or treated with either: (b) EC145 at 2 μmol/kg/injection, TIW for 2 weeks; or (c) Gemcitabine at 40 mg/kg, BIW, 5 doses or (d) EC145 at 1 μmol/kg/injection, TIW for 2 weeks+Gemcitabine at 40 mg/kg, BIW, 5 doses. Treatment with EC145 alone resulted in 0 partial responses, 0 complete responses, and 2 Cures. Treatment with Gemcitabine alone resulted in no partial responses, complete responses, or Cures. The combination treatment resulted in no partial responses, complete responses, or Cures.
Figure 15:
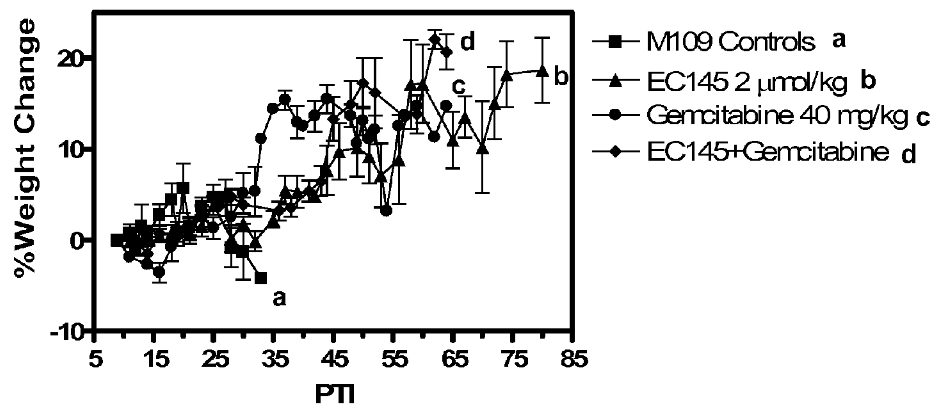
FIG. 15. Percentage weight change (average for the five animals in each treatment group) measured for Balb/c mice with M109 tumors (86-149 $mm^3$ range) that were (a) untreated; or treated with either: (b) EC145 at 2 μmol/kg/injection, TIW for 2 weeks; or (c) Gemcitabine at 40 mg/kg, BIW, 5 doses or (d) EC145 at 1 μmol/kg/injection, TIW for 2 weeks+Gemcitabine at 40 mg/kg, BIW, 5 doses.

Randomized Balb/c mice with M109 tumors (86-149 $mm^3$ range) were (a) untreated; or treated with either: (b) EC145 at 2 μmol/kg/injection, TIW for 2 weeks; or (c) Gemcitabine at 40 mg/kg, BIW, 5 doses or (d) EC145 at 1 μmol/kg/injection, TIW for 2 weeks+Gemcitabine at 40 mg/kg, BIW, 5 doses. See FIG. 14 for tumor response and FIG. 15 for weight change during the treatment period. Treatment with Gemcitabine alone resulted in no partial responses, complete responses, or Cures. The combination treatment resulted in no partial responses, complete responses, or Cures.

Example

Combination Therapy of EC145 with Tarceva (Erlotinib)

Figure 16:
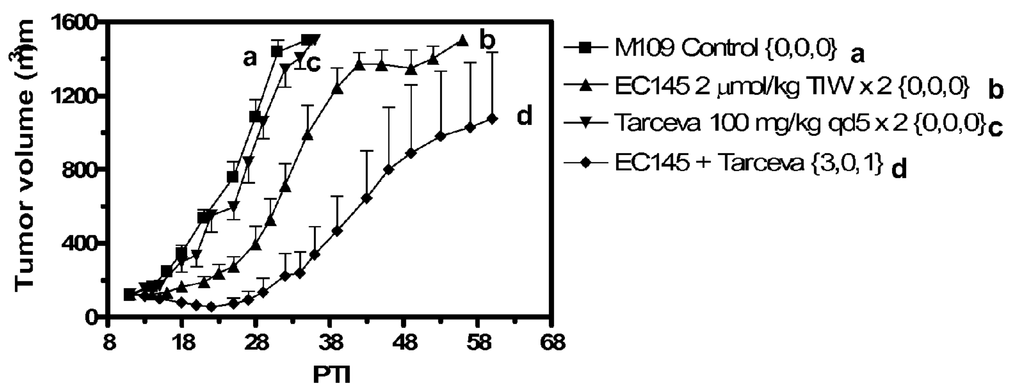
FIG. 16. Tumor volume (average for the five animals in each treatment group) measured for Balb/c mice with M109 tumors (99-164 $mm^3$ range) that were (a) untreated; or treated with either: (b) EC145 at 2 μmol/kg/injection, TIW for 2 weeks; or (c) Tarceva (i.e. erlotinib) at 100 mg/kg, qd5 for 2 weeks or (d) EC145 at 1 μmol/kg/injection, TIW for 2 weeks+Tarceva at 100 mg/kg, qd5 for 2 weeks. Treatment with EC145 alone resulted in 0 partial responses, 0 complete responses, and 0 Cures. Treatment with Tarceva alone resulted in no partial responses, complete responses, nor Cures. The combination treatment resulted in 3 partial responses and 1 Cure.
Figure 17:
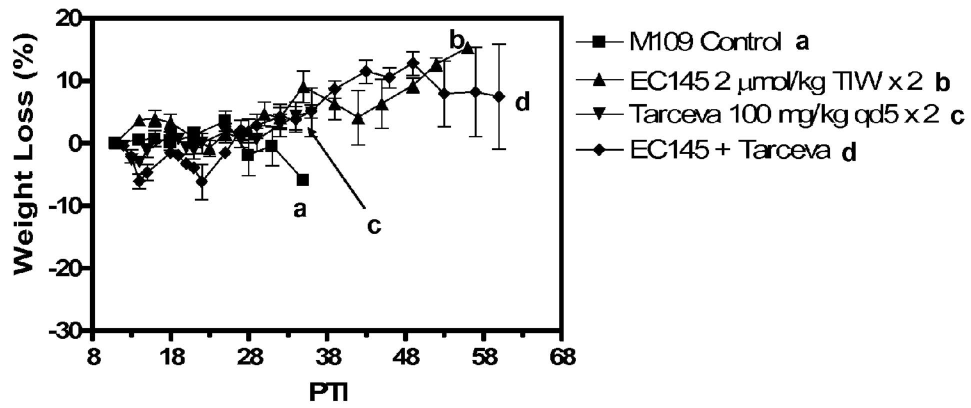
FIG. 17. Percentage weight change (average for the five animals in each treatment group) measured for Balb/c mice with M109 tumors (99-164 $mm^3$ range) that were (a) untreated; or treated with either: (b) EC145 at 2 μmol/kg/injection, TIW for 2 weeks; or (c) Tarceva at 100 mg/kg, qd5 for 2 weeks or (d) EC145 at 1 μmol/kg/injection, TIW for 2 weeks+Tarceva at 100 mg/kg, qd5 for 2 weeks.
Figure 18:
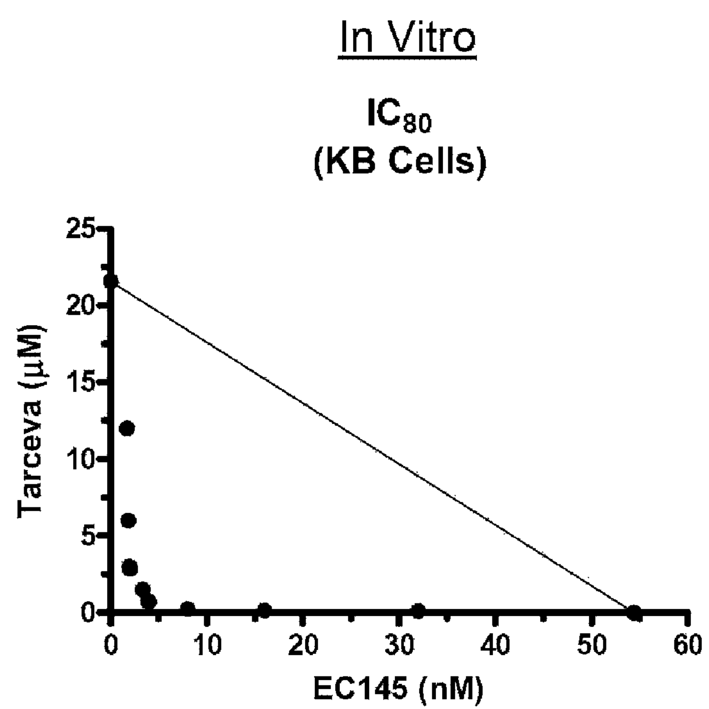
FIG. 18. The isobologram ($IC_H$) shows that in vitro activity of EC145 and Tarceva against KB tumor cells is synergistic.
Figure 19:
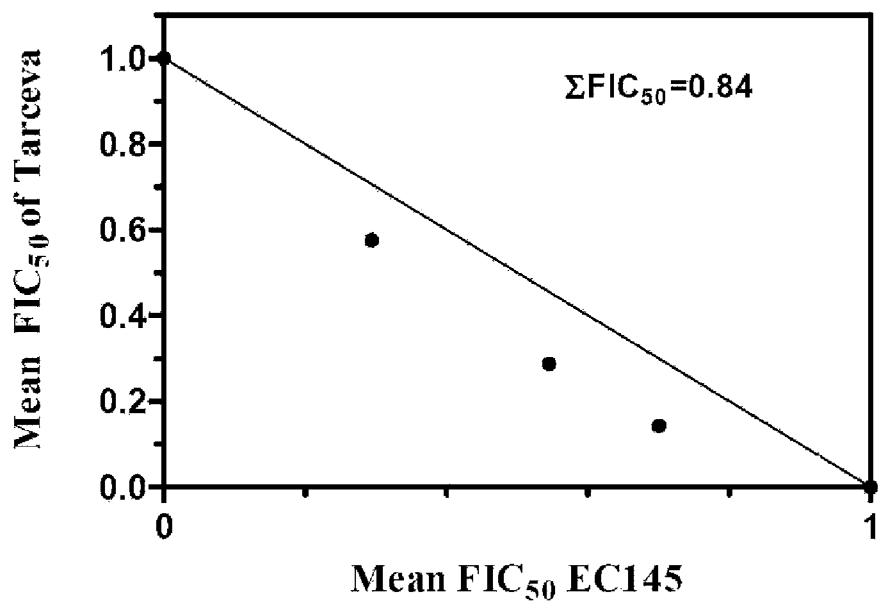
FIG. 19. The isobologram ($IC_{50}$ values) shows that the in vitro activity of Tarceva and EC145 against KB cells are additive.
Figure 20:
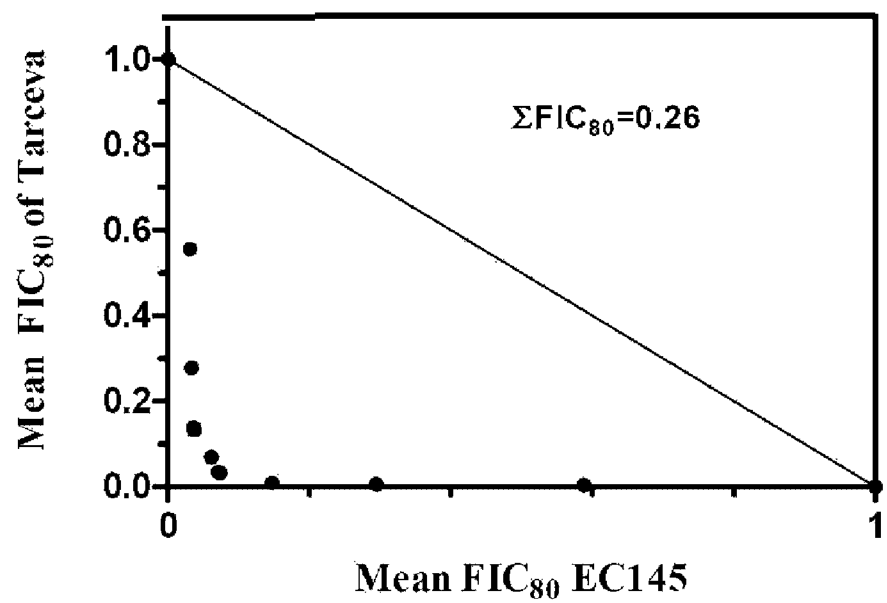
FIG. 20. The isobologram ($IC_{80}$ values) shows that the in vitro activity of Tarceva and EC145 against KB cells are synergistic.

Randomized Balb/c mice with M109 tumors (99-164 $mm^3$ range) were (a) untreated; or treated with either: (b) EC145 at 2 μmol/kg/injection, TIW for 2 weeks; or (c) Tarceva at 100 mg/kg, qd5 for 2 weeks or (d) EC145 at 1 μmol/kg/injection, TIW for 2 weeks+Tarceva at 100 mg/kg, qd5 for 2 weeks. See FIG. 16 for tumor response and FIG. 17 for weight change during the treatment period. Treatment with Tarceva alone resulted in no partial responses, complete responses, nor Cures. The combination treatment resulted in 3 partial responses and 1 Cure.

Example

Combination Therapy of EC145 with Tarceva (Erlotinib)

Figure 21:
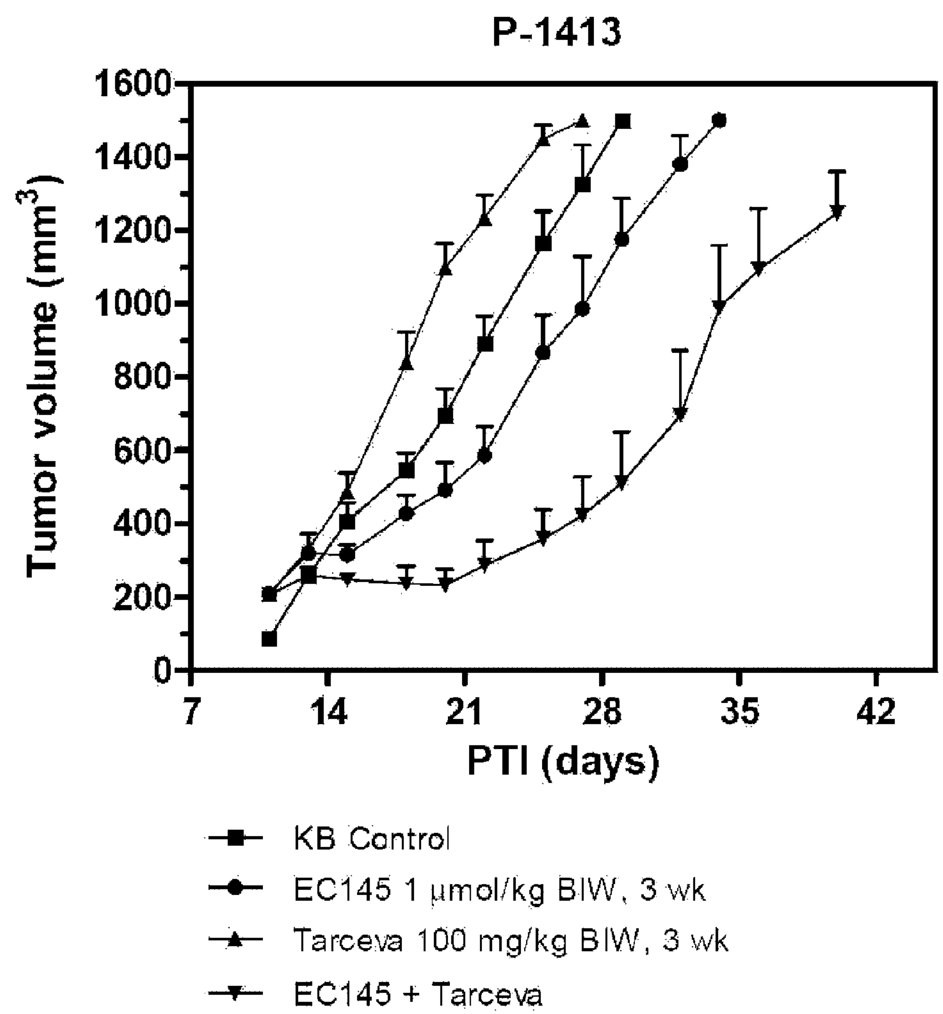
FIG. 21. Tumor volume (average) measured for nu/nu mice with KB tumors that were (■) untreated; or treated with either: (●) EC145 at 1 μmol/kg/injection, TIW for 3 weeks; or (▲) Tarceva at 100 mg/kg, BIW for 3 weeks or (▼) EC145 at 1 μmol/kg/injection, TIW for 3 weeks+Tarceva at 100 mg/kg, BIW for 3 weeks.
Figure 22:
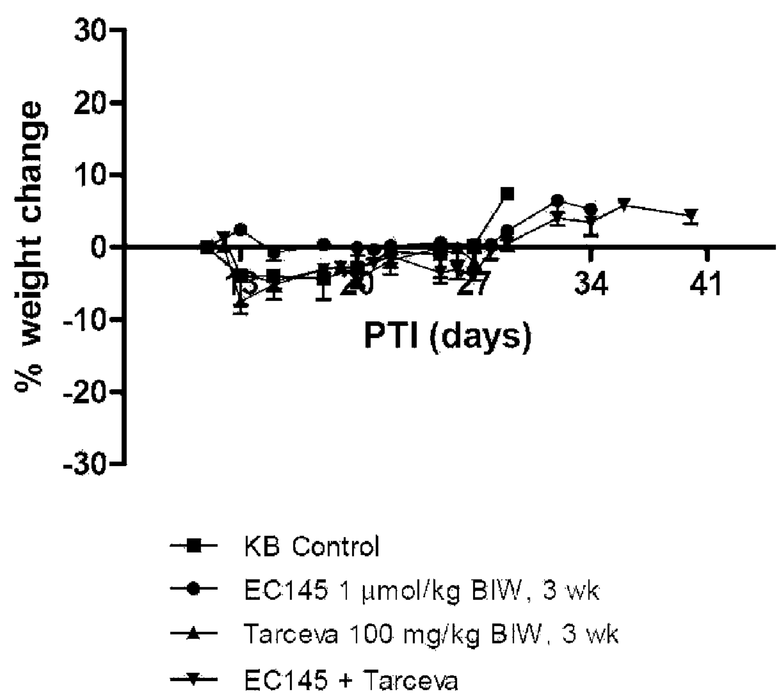
FIG. 22. Percentage weight change (average) measured for nu/nu mice with KB tumors that were (■) untreated; or treated with either: (●) EC145 at 1 μmol/kg/injection, TIW for 3 weeks; or (▲) Tarceva at 100 mg/kg, BIW for 3 weeks or (▼) EC145 at 1 μmol/kg/injection, TIW for 3 weeks+Tarceva at 100 mg/kg, BIW for 3 weeks.

Randomized nu/nu mice with KB tumors were (■) untreated; or treated with either: (●) EC145 at 1 μmol/kg/injection, TIW for 3 weeks; or (▲) Tarceva at 100 mg/kg, BIW for 3 weeks or (▼) EC145 at 1 μmol/kg/injection, TIW for 3 weeks+Tarceva at 100 mg/kg, BIW for 3 weeks. See FIG. 21 for tumor response and FIG. 22 for percentage weight change.

Example

Combination Therapy of Unconjugated Vindesine with Doxil

Figure 25:
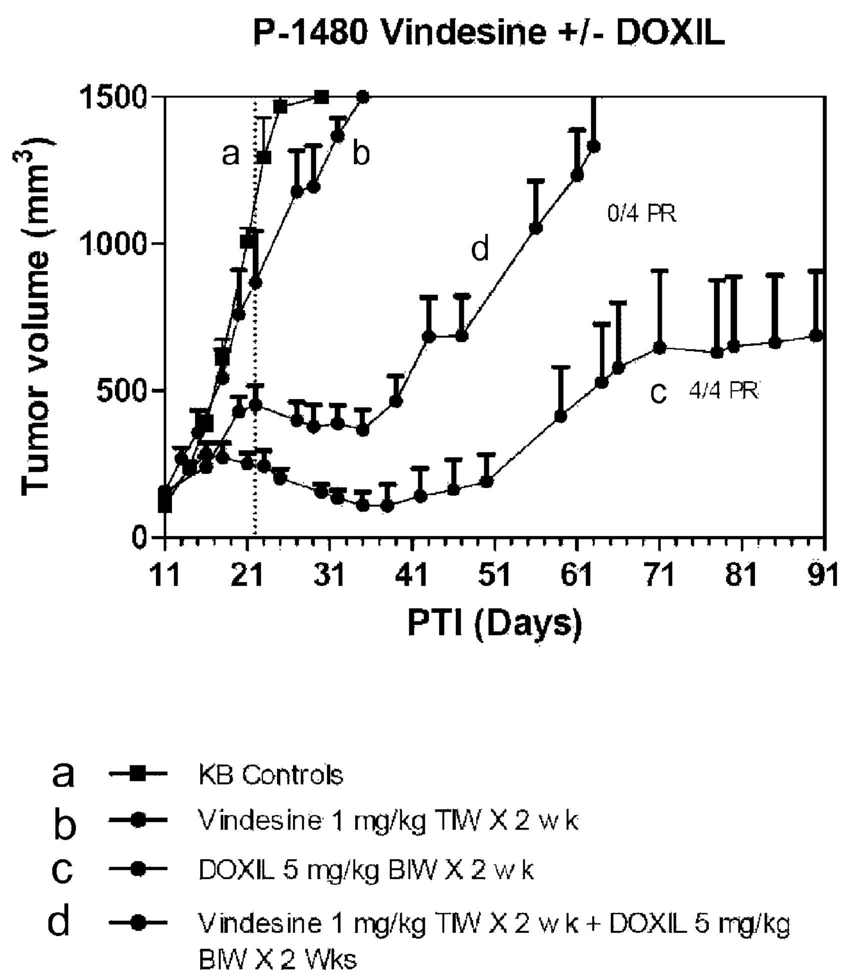
FIG. 25. Tumor volume (average for the four animals in each treatment group) measured for nu/nu mice with KB tumors (123-205 $mm^3$ range) that were (a) untreated; or treated with either: (b) vindesine at 1 mg/kg/injection, TIW for 2 weeks; or (c) DOXIL at 5 mg/kg, BIW for 2 weeks (4/4 PR) or (d) vindesine at 1 mg/kg/injection, TIW for 2 weeks+DOXIL at 5 mg/kg, BIW for 2 weeks (0/4 PR). Unconjugated vindesine antagonizes Doxil activity.
Figure 26:
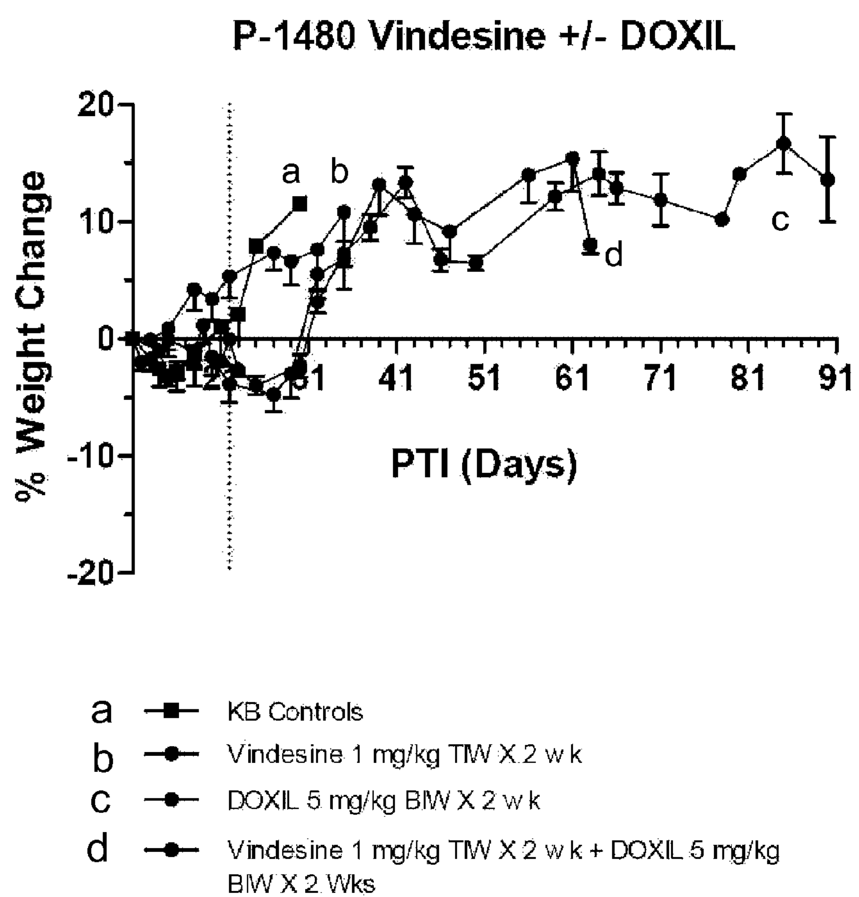
FIG. 26. Percentage weight gain (average for the four animals in each treatment group) measured for nu/nu mice with KB tumors (114-177 $mm^3$ range) that were (a) untreated; or treated with either: (b) vindesine at 1 mg/kg/injection, TIW for 2 weeks; or (c) DOXIL at 5 mg/kg, BIW for 2 weeks or (d) vindesine at 1 mg/kg/injection, TIW for 2 weeks+DOXIL at 5 mg/kg, BIW for 2 weeks. Unconjugated vindesine antagonizes Doxil activityl.

Randomized nu/nu mice with KB tumors (123-205 $mm^3$ range) were (a) untreated; or treated with either: (b) vindesine at 1 mg/kg/injection, TIW for 2 weeks; or (c) DOXIL at 5 mg/kg, BIW for 2 weeks or (d) vindesine at 1 mg/kg/injection, TIW for 2 weeks+DOXIL at 5 mg/kg, BIW for 2 weeks. See FIG. 25 for tumor response and FIG. 26 for percentage weight change. Treatment with Doxil alone resulted in 4 PRs out of 4 animals. The combination treatment resulted in 0 PRs out of animals. Unconjugated vindesine antagonizes Doxil activity.

Example

Combination Therapy of Unconjugated DAVLBH with Doxil

Randomized nu/nu mice with KB tumors (122-192 $mm^3$ range) that were (a) untreated; or treated with either: (b)

Figure 27:
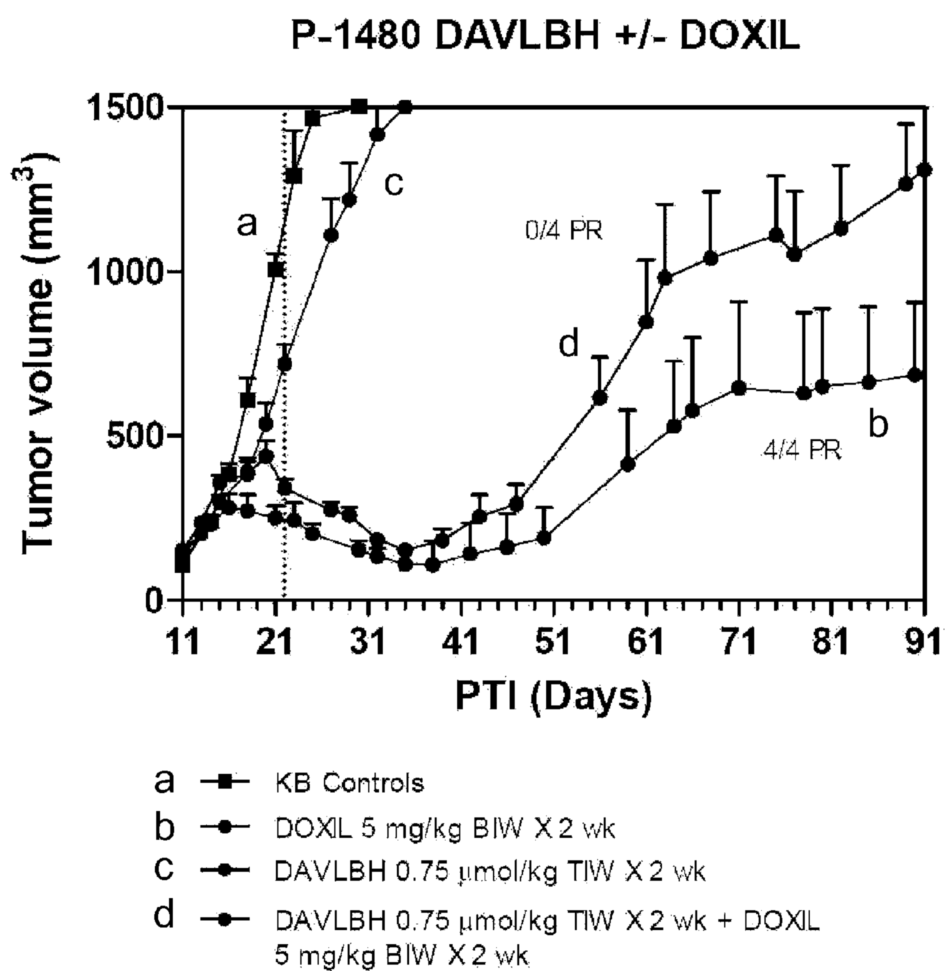
FIG. 27. Tumor volume (average for the four animals in each treatment group) measured for nu/nu mice with KB tumors (122-192 $mm^3$ range) that were (a) untreated; or treated with either: (b) DOXIL at 5 mg/kg, BIW for 2 weeks (4/4 PR); or (c) DAVLBH at 0.75 μmol/kg/injection, TIW for 2 weeks or (d) DAVLBH at 0.75 μmol/kg/injection, TIW for 2 weeks+DOXIL at 5 mg/kg, BIW for 2 weeks (0/4 PR). Unconjugated DAVLBH antagonizes Doxil activity.
Figure 28:
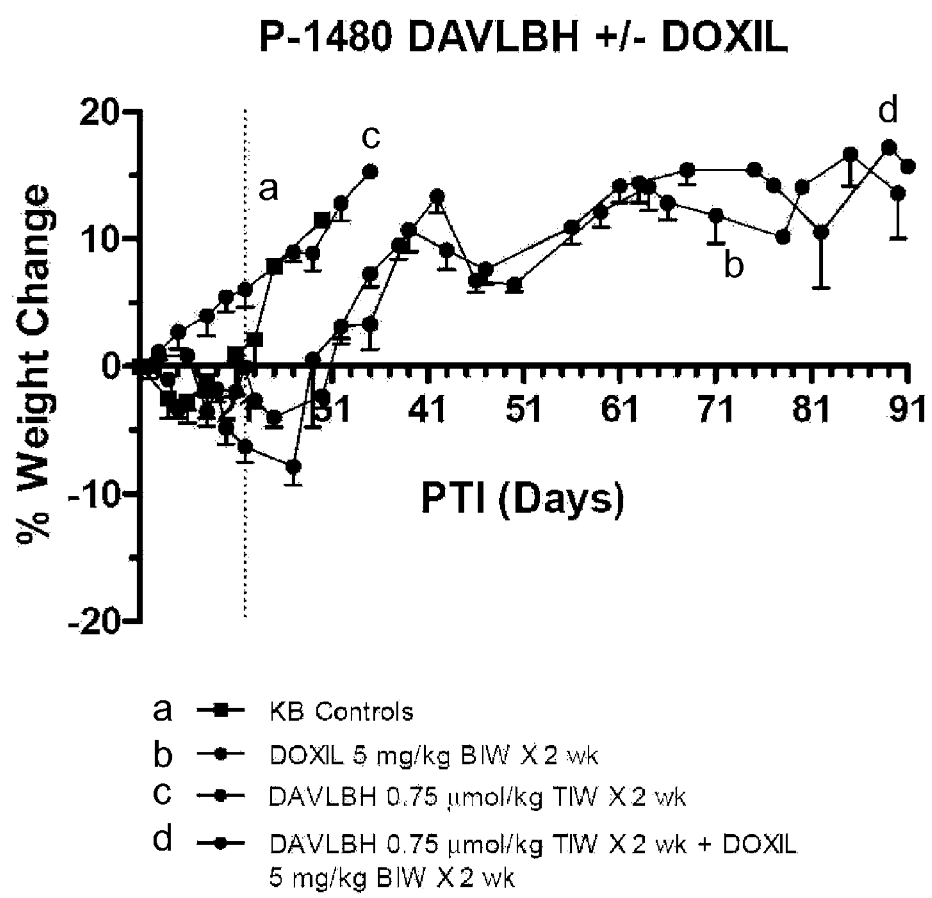
FIG. 28. Percentage weight change (average for the four animals in each treatment group) measured for nu/nu mice with KB tumors (114-177 $mm^3$ range) that were (a) untreated; or treated with either: (b) DOXIL at 5 mg/kg, BIW for 2 weeks; or (c) DAVLBH at 0.75 μmol/kg/injection, TIW for 2 weeks or (d) DAVLBH at 0.75 μmol/kg/injection, TIW for 2 weeks+DOXIL at 5 mg/kg, BIW for 2 weeks.
Figure 29:
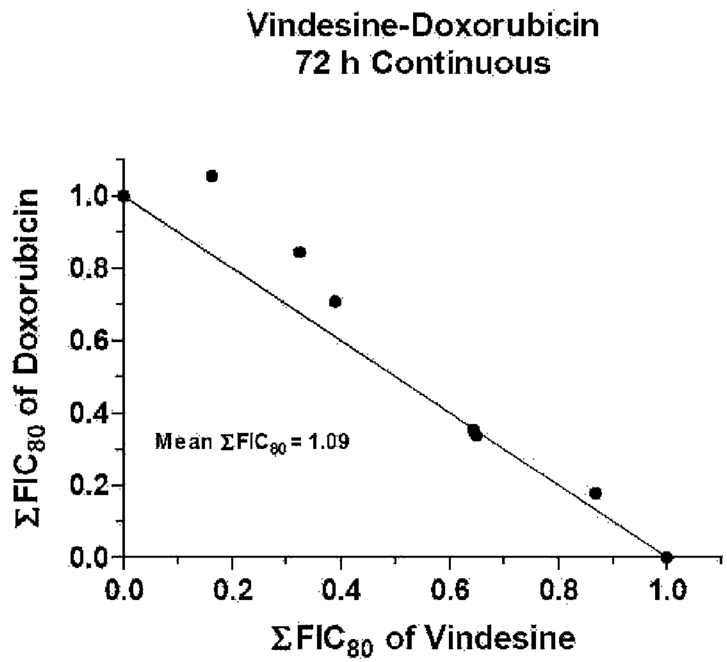
FIG. 29. Isobologram ($IC_{80}$ values) for in vitro activity (continuous 72 hour treatment) of combinations of Vindesine and Doxorubicin shows antagonism.
Figure 30:
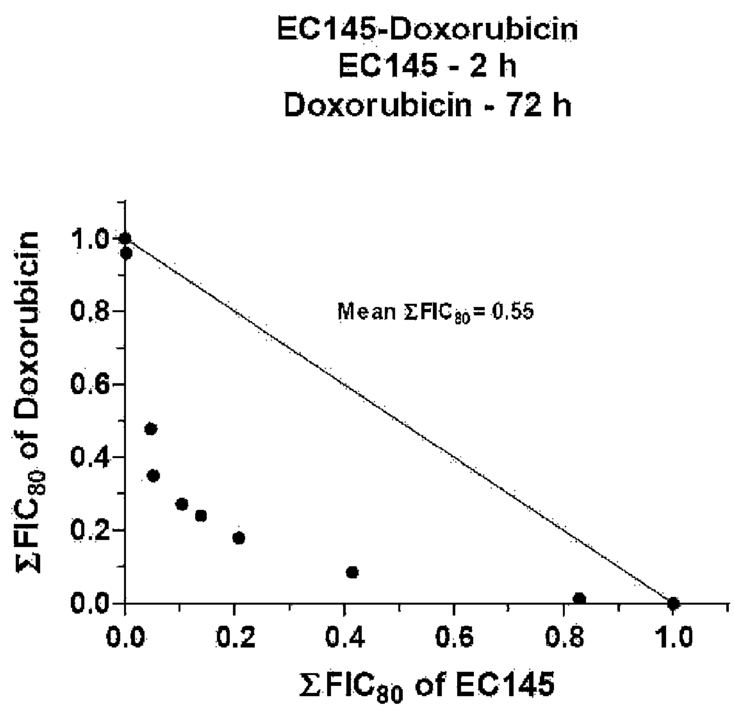
FIG. 30. Isobologram ($IC_{80}$ values) for in vitro activity (continuous 72 hour treatment with Doxorubicin, 2 hour treatment with EC145) of combinations of EC145 and Doxorubicin show synergism.
Figure 31:
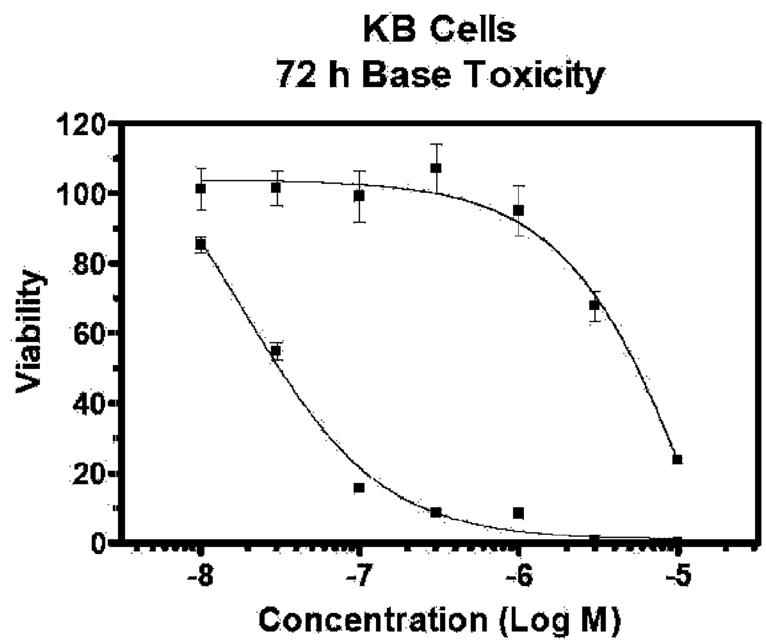
FIG. 31. In vitro cytotoxicity of Doxorubicin ($IC_{50}$ 34 nM) and Doxil (3900 nM) toward KB tumor cells.
Figure 32:
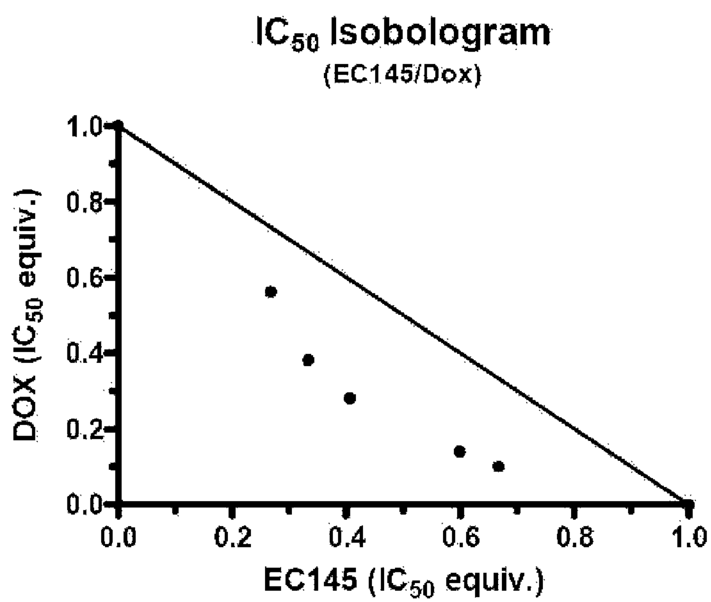
FIG. 32. Isobologram ($IC_{50}$ values) for in vitro activity for a combination of EC145 and Doxil against KB tumor cells.
Figure 33:
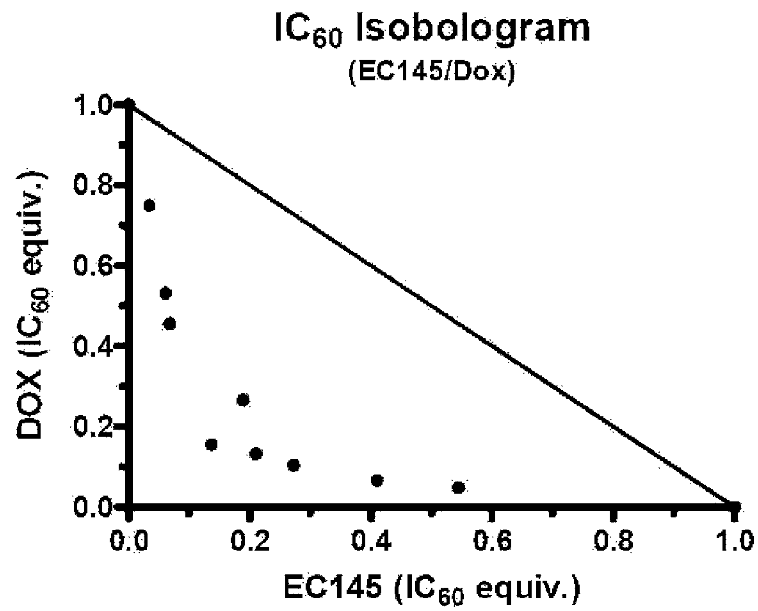
FIG. 33. Isobologram ($IC_{60}$ values) for in vitro activity for a combination of EC145 and Doxil against KB tumor cells.
Figure 34:
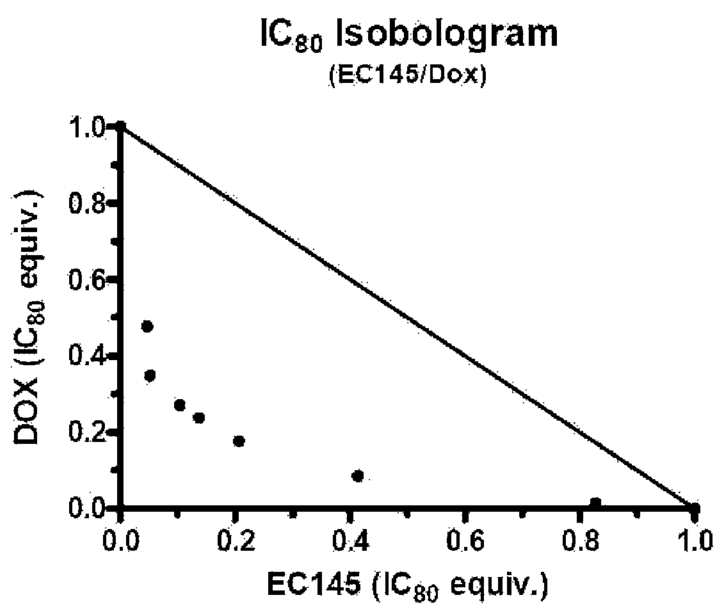
FIG. 34. Isobologram ($IC_{80}$ values) for in vitro activity for a combination of EC145 and Doxil against KB tumor cells.
Figure 35:
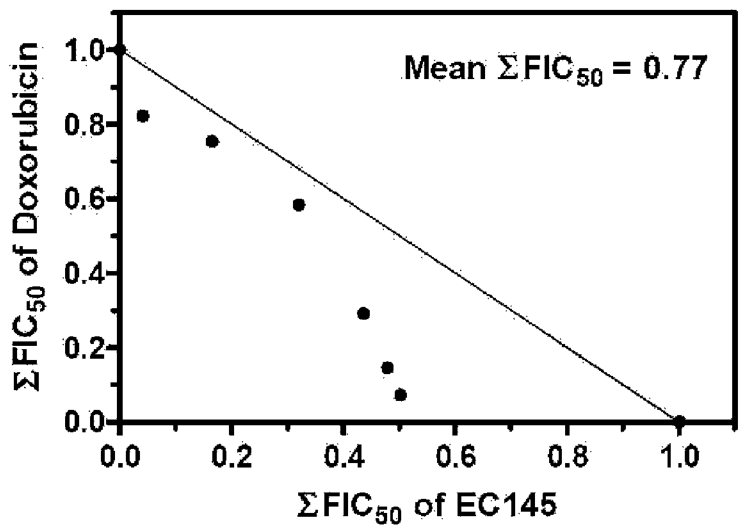
FIG. 35. Isobologram ($IC_{50}$ values) for in vitro activity for a combination of EC145 treatment (2 hours) followed by Doxorubicin treatment (24 hours) against KB tumor cells.
Figure 36:
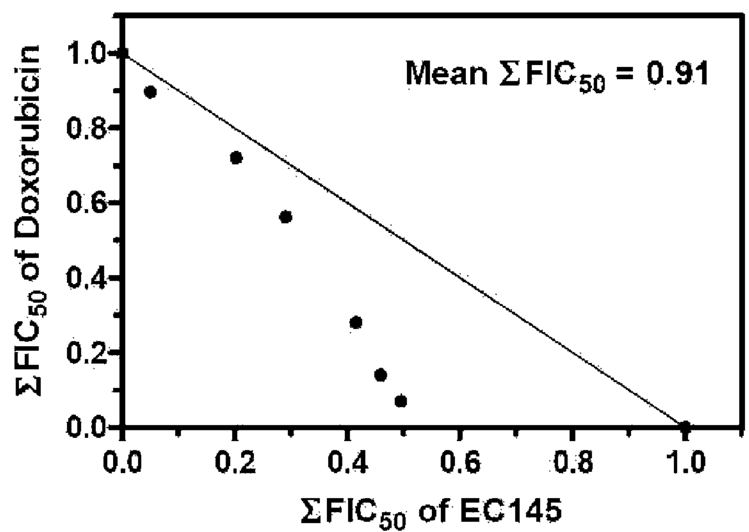
FIG. 36. Isobologram ($IC_{50}$ values) for in vitro activity for a combination of Doxorubicin treatment (24 hours) followed by EC145 treatment (2 hours) against KB tumor cells.
Figure 37:
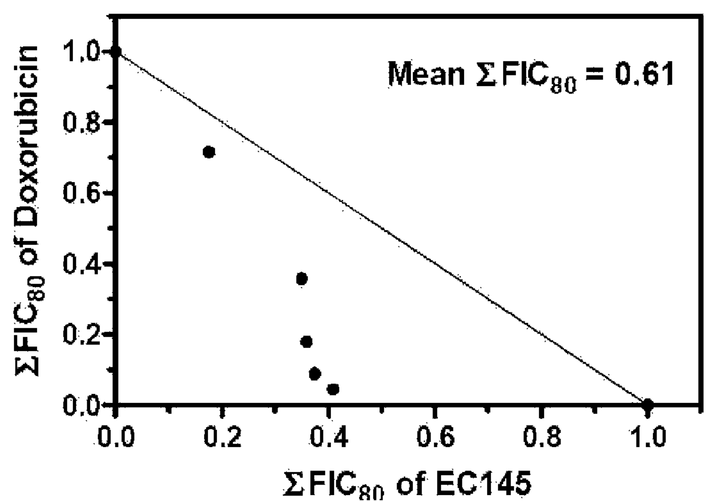
FIG. 37. Isobologram ($IC_{80}$ values) for in vitro activity for a combination of EC145 treatment (2 hours) followed by Doxorubicin treatment (24 hours) against KB tumor cells.
Figure 38:
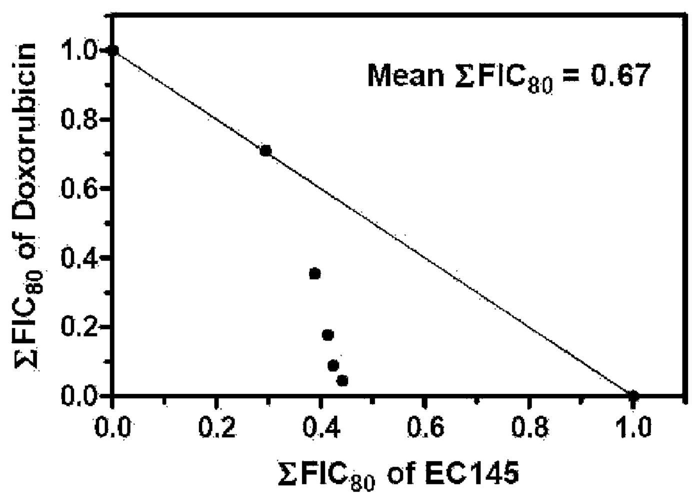
FIG. 38. Isobologram ($IC_{80}$ values) for in vitro activity for a combination of Doxorubicin treatment (24 hours) followed by EC145 treatment (2 hours) against KB tumor cells.
Figure 39:
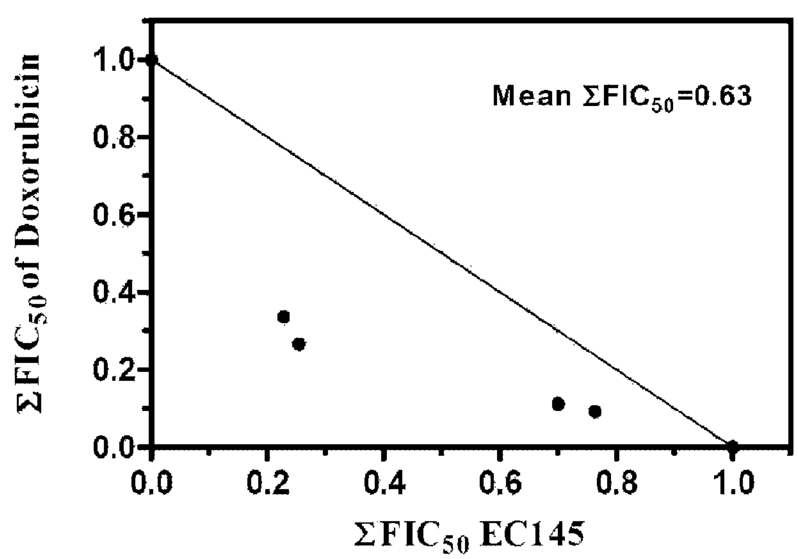
FIG. 39. Isobologram ($IC_{80}$ values) for in vitro activity for a combination of Doxorubicin treatment and EC145 treatment against J64556 lymphoma cells.
Figure 40:
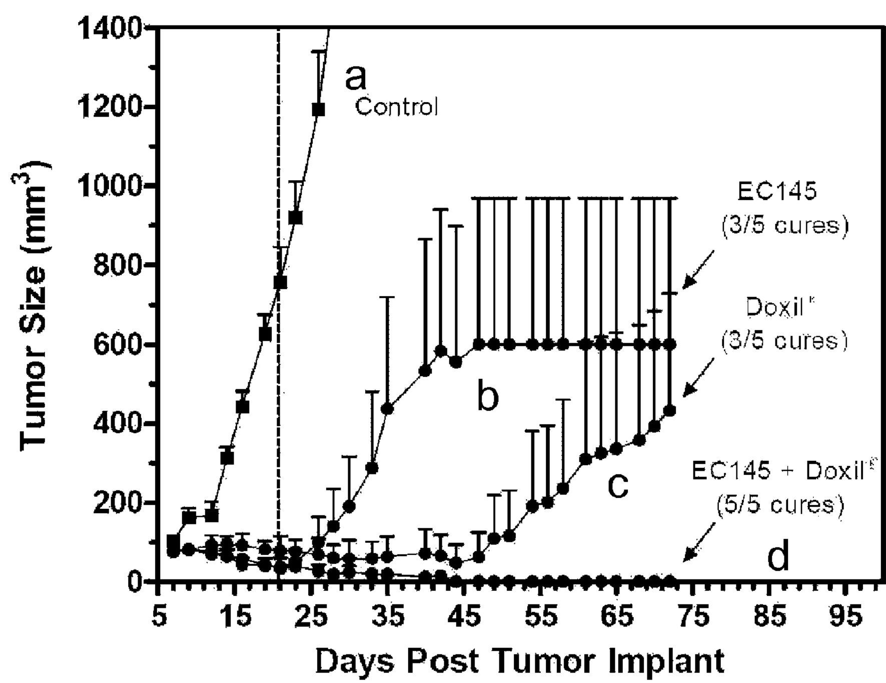
FIG. 40. Tumor volume (average for the five animals in each treatment group) measured for mice with M109 tumors that were (a) untreated; or treated with either: (b) EC145 at 1 μmol/kg/injection, TIW for 2 weeks (3/5 cures); or (c) DOXIL at 4 mg/kg, BIW for 2 weeks (3/5 cures) or (d) EC145 at 1 μmol/kg/injection, TIW for 2 weeks+DOXIL at 4 mg/kg, BIW for 2 weeks (5/5 cures).
Figure 41:
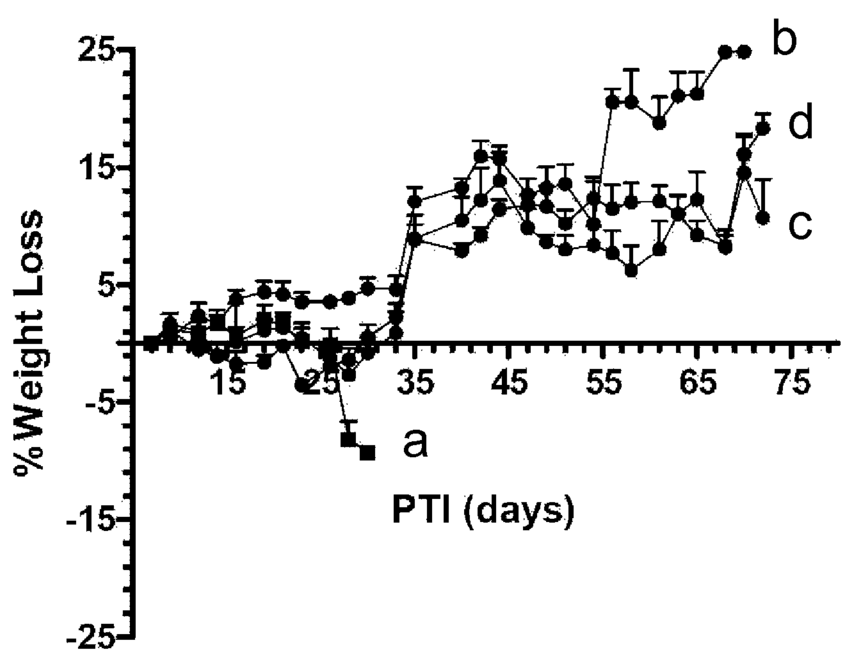
FIG. 41. Percentage weight change (average for the five animals in each treatment group) measured for mice with M109 tumors that were (a) untreated; or treated with either: (b) EC145 at 1 μmol/kg/injection, TIW for 2 weeks; or (c) DOXIL at 4 mg/kg, BIW for 2 weeks or (d) EC145 at 1 μmol/kg/injection, TIW for 2 weeks+DOXIL at 4 mg/kg, BIW for 2 weeks.
Figure 54:
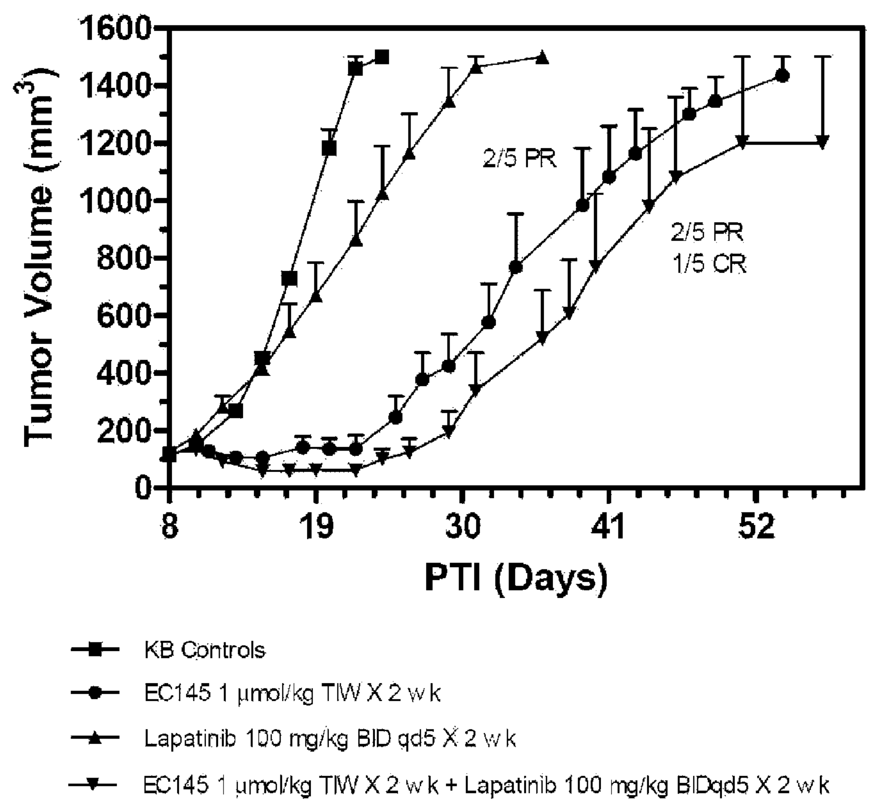
FIG. 54. Tumor volume (average for the five animals in each treatment group) measured for nu/nu mice with KB tumors (109-188 $mm^3$ range) that were (■) untreated; or treated with either: (●) EC145 at 1 μmol/kg/injection, TIW for 2 weeks; or (▲) Lapatinib at 100 mg/kg, BID qd5 for 2 weeks or (▼) EC145 at 1 μmol/kg/injection, TIW for 2 weeks+Lapatinib at 100 mg/kg, BID qd5 for 2 weeks.
Figure 55:
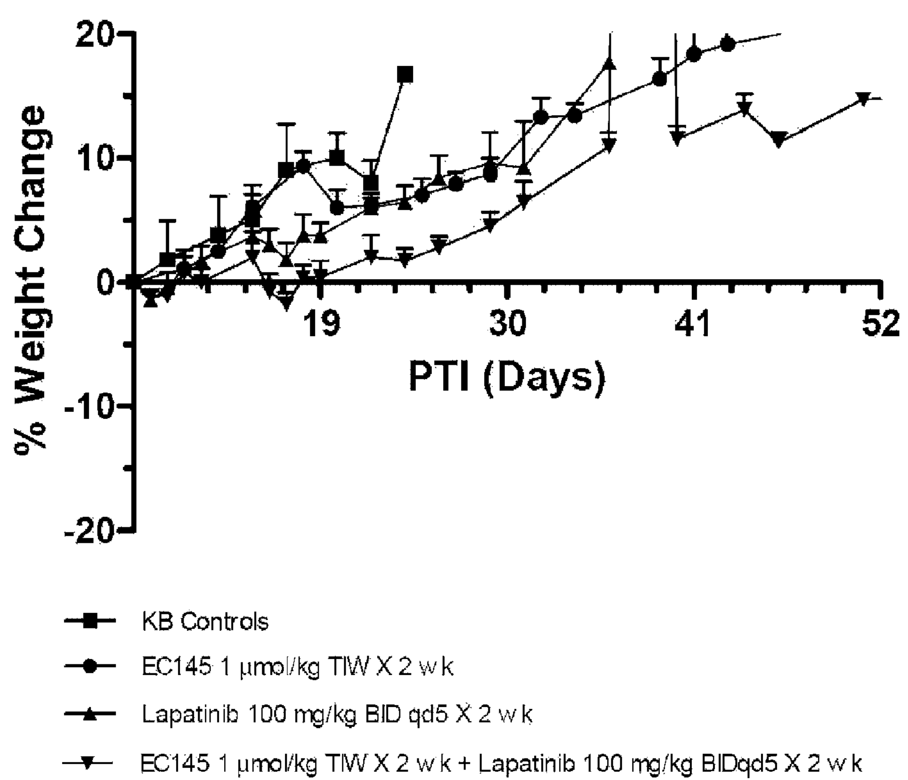
FIG. 55. Percentage weight change (average for the five animals in each treatment group) measured for nu/nu mice with KB tumors (109-188 $mm^3$ range) that were (■) untreated; or treated with either: (●) EC145 at 1 μmol/kg/injection, TIW for 2 weeks; or (▲) Lapatinib at 100 mg/kg, BID qd5 for 2 weeks or (▼) EC145 at 1 μmol/kg/injection, TIW for 2 weeks+Lapatinib at 100 mg/kg, BID qd5 for 2 weeks.

DOXIL at 5 mg/kg, BIW for 2 weeks; or (c) DAVLBH at 0.75 μmol/kg/injection, TIW for 2 weeks or (d) DAVLBH at 0.75 μmol/kg/injection, TIW for 2 weeks+DOXIL at 5 mg/kg, BIW for 2 weeks. See FIG. 27 for tumor response and FIG. 28 for percentage weight change. Treatment with Doxil alone resulted in 4 PRs out of 4 animals. The combination treatment resulted in O PRs out of animals. Unconjugated DAVLBH antagonizes Doxil activity Example Combination Therapy of EC145 with Lapatinib Randomized nu/nu mice with KB tumors (109-188 $mm^3$ range) were (■) untreated; or treated with either: (●) EC145 at 1 μmol/kg/injection, TIW for 2 weeks; or (▲) Lapatinib at 100 mg/kg, BID qd5 for 2 weeks or (▼) EC145 at 1 μmol/kg/injection, TIW for 2 weeks+Lapatinib at 100 mg/kg, BID qd5 for 2 weeks. See FIG. 54 for tumor response and FIG. 55 for percentage weight change.

Example

Combination Therapy of EC145 with Alimta (Pemetrexed)

Figure 56:
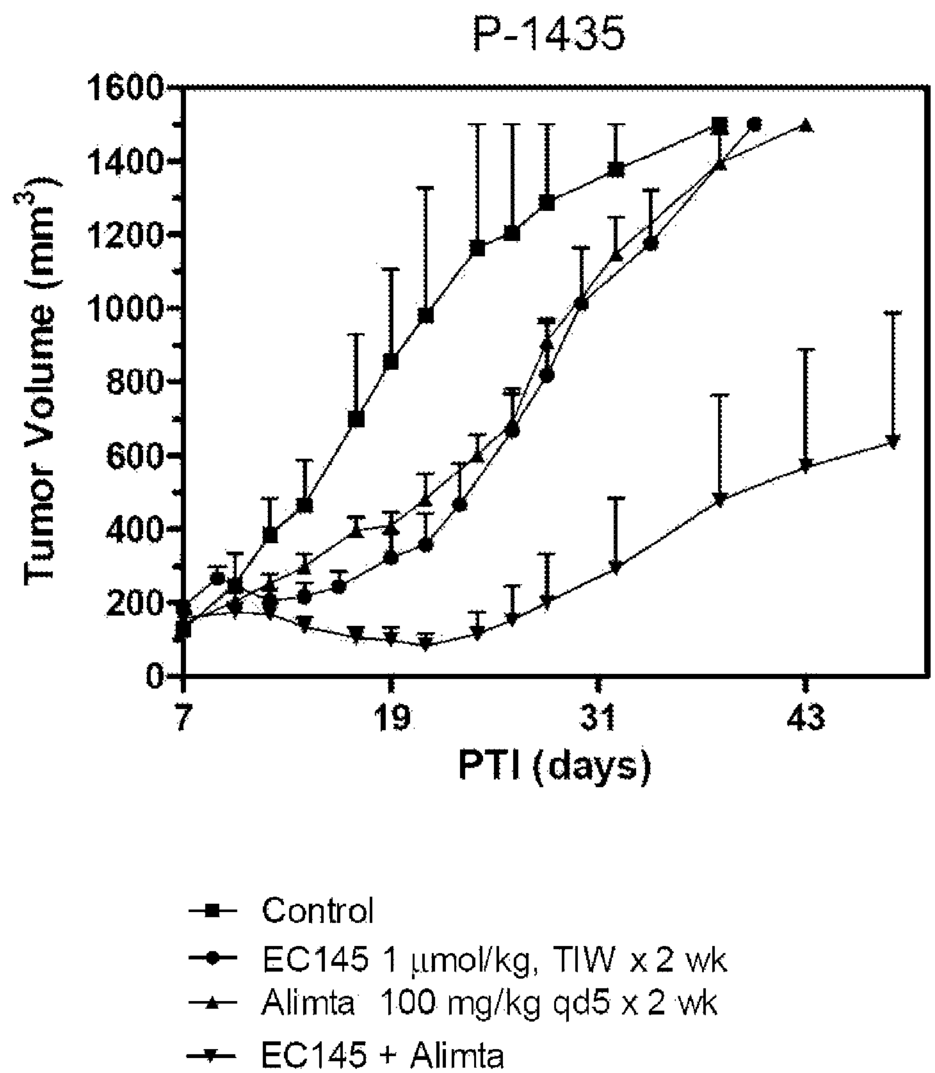
FIG. 56. Tumor volume (average for the five animals in each treatment group) measured for nu/nu mice with KB tumors (109-188 $mm^3$ range) that were (■) untreated; or treated with either: (●) EC145 at 1 μmol/kg/injection, TIW for 2 weeks; or (▲) Alimta at 100 mg/kg, qd5 for 2 weeks or (▼) EC145 at 1 μmol/kg/injection, TIW for 2 weeks+Alimta at 100 mg/kg, qd5 for 2 weeks. All cohorts received 5MTHF=320 μg/kg (705 nmol/kg) via oral gavage during study days 2-19 (5 days before treatment to last day of treatment).
Figure 57:
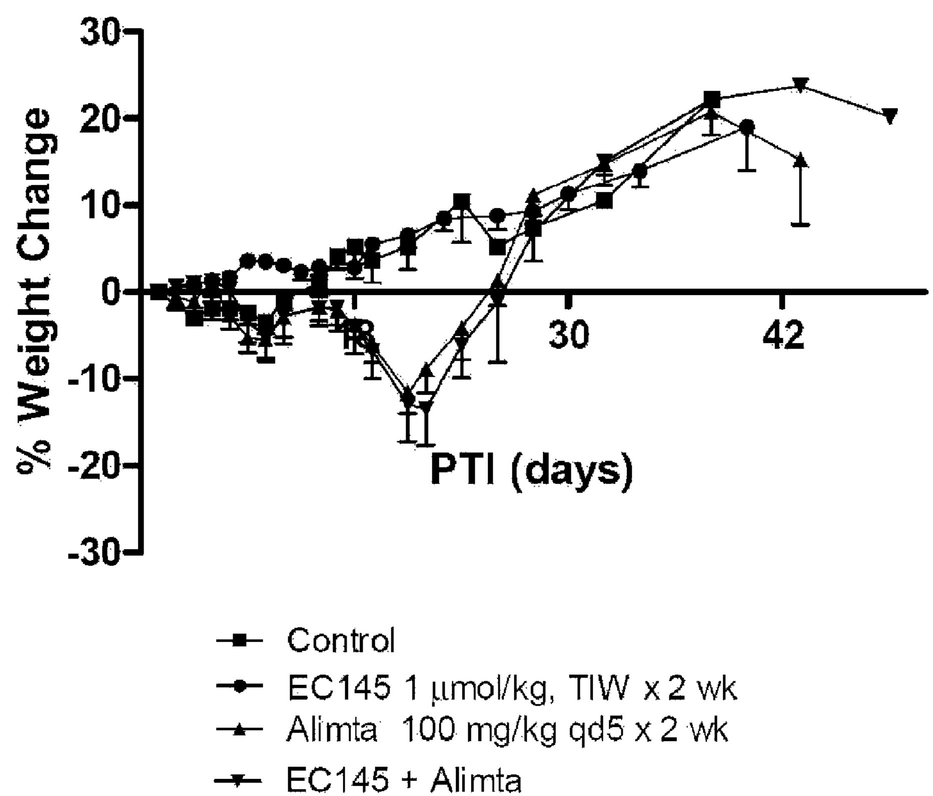
FIG. 57. Percentage weight change (average for the five animals in each treatment group) measured for nu/nu mice with KB tumors (109-188 $mm^3$ range) that were (■) untreated; or treated with either: (■) EC145 at 1 μmol/kg/injection, TIW for 2 weeks; or (▲) Alimta at 100 mg/kg, qd5 for 2 weeks or (▼) EC145 at 1 μmol/kg/injection, TIW for 2 weeks+Alimta at 100 mg/kg, qd5 for 2 weeks. All cohorts received 5MTHF=320 μg/kg (705 nmol/kg) via oral gavage during study days 2-19 (5 days before treatment to last day of treatment).
Figure 58:
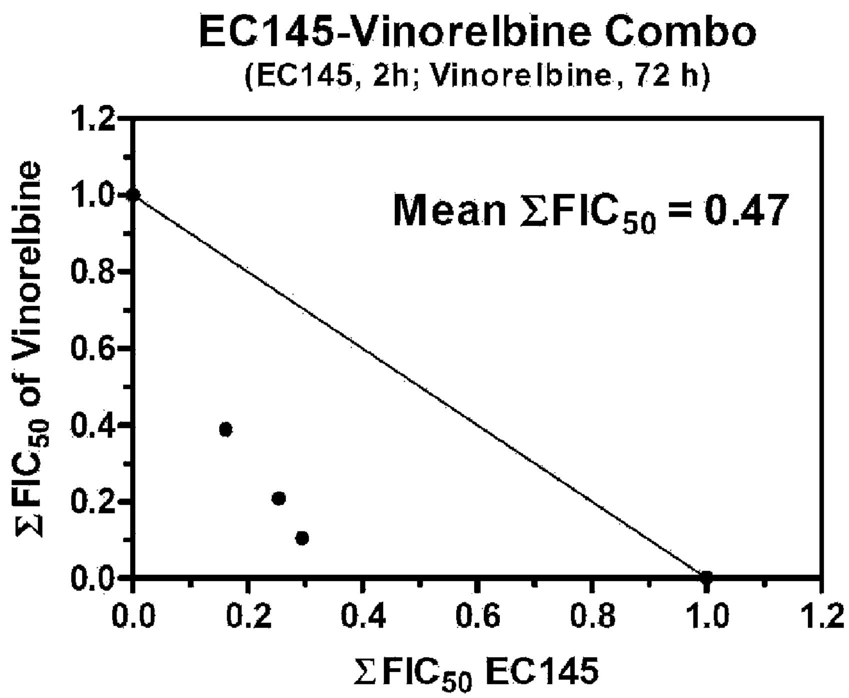
FIG. 58. Isobologram ($IC_{50}$ values) for in vitro activity for a combination of EC145 (2 hour treatment) and Vinorelbine (72 hour treatment) against KB tumor cells.
Figure 59:
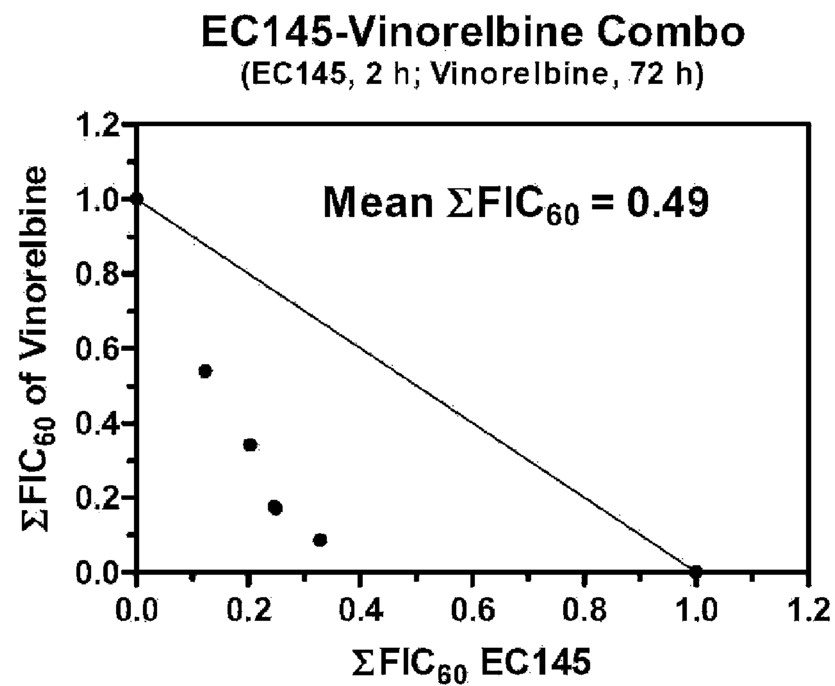
FIG. 59. Isobologram ($IC_{60}$ values) for in vitro activity for a combination of EC145 (2 hour treatment) and Vinorelbine (72 hour treatment) against KB tumor cells.

Randomized nu/nu mice with KB tumors (109-188 $mm^3$ range) were (■) untreated; or treated with either: (●) EC145 at 1 μmol/kg/injection, TIW for 2 weeks; or (▲) Alimta at 100 mg/kg, qd5 for 2 weeks or (▼) EC145 at 1 μmol/kg/injection, TIW for 2 weeks+Alimta at 100 mg/kg, qd5 for 2 weeks. All cohorts received 5MTHF=320 μg/kg (705 nmol/kg) via oral gavage during study days 2-19 (5 days before treatment to last day of treatment). See FIG. 56 for tumor response and FIG. 57 for percentage weight change.

Example

Combination Therapy of EC145 with Topotecan

Figure 8:
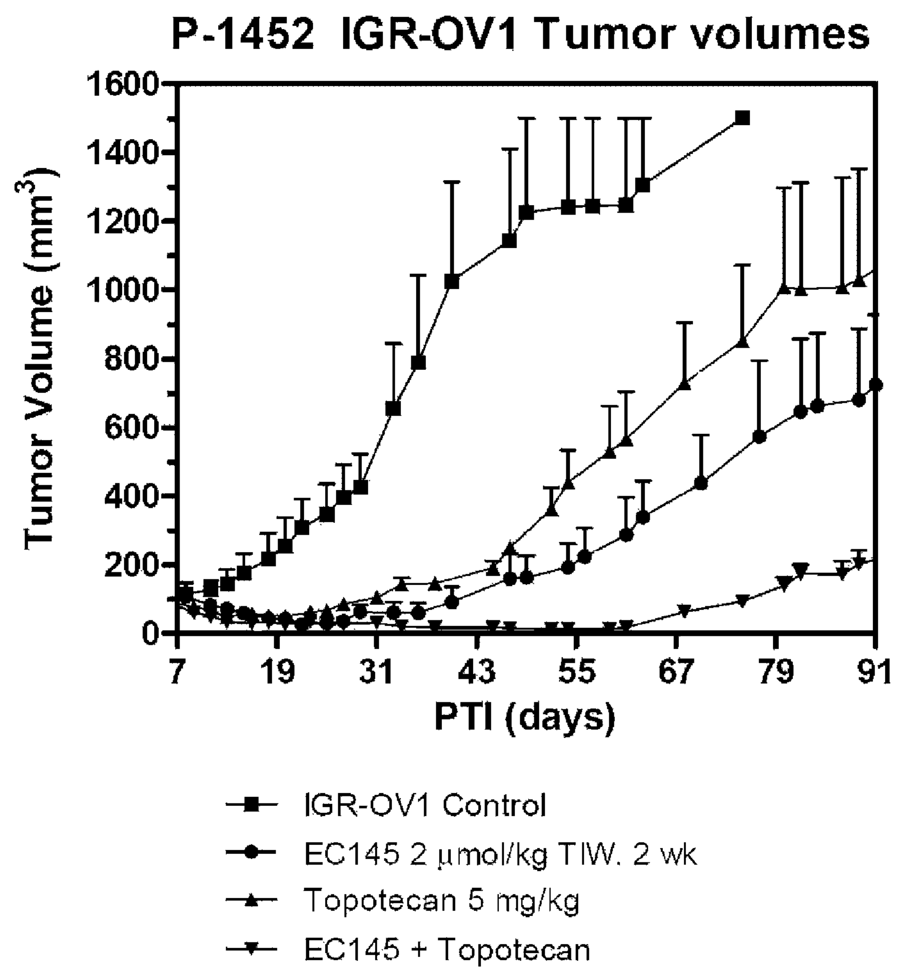
FIG. 8. Tumor volume measured for mice with IGR-OV1 tumors that were (■) untreated; or treated with either: (●) EC145 at 2 μmol/kg/injection, TIW for 2 weeks; or (▲) topotecan at 5 mg/kg, BIW for 2 weeks or (▼) EC145 at 2 μmol/kg/injection, TIW for 2 weeks+topotecan at 5 mg/kg, BIW for 2 weeks.
Figure 9:
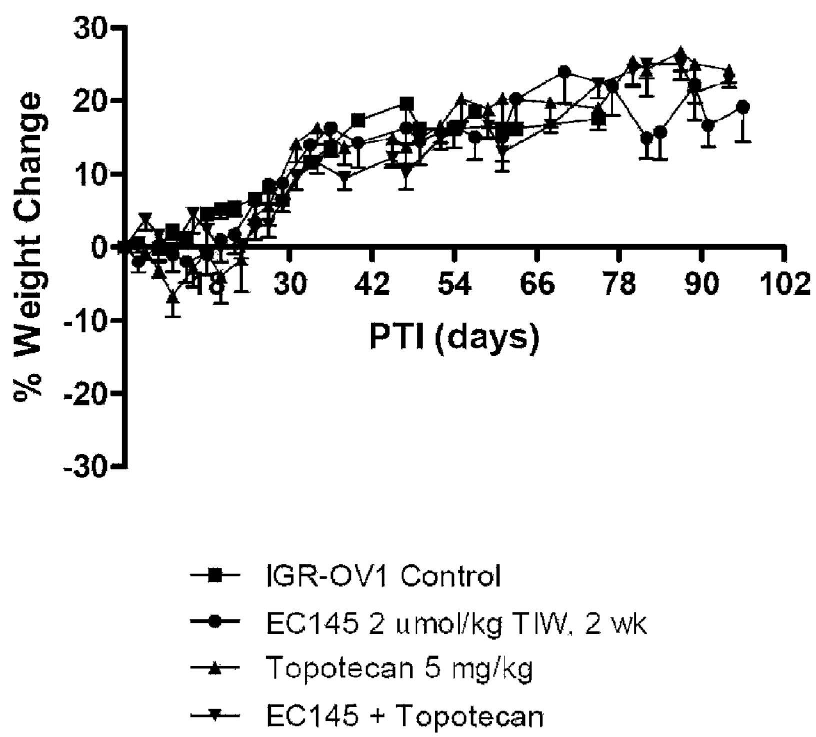
FIG. 9. Percentage weight change mice with IGR-OV1 tumors that were (■) untreated; or treated with either: (●) EC145 at 2 μmol/kg/injection, TIW for 2 weeks; or (▲) topotecan at 5 mg/kg, BIW for 2 weeks or (▼) EC145 at 2 μmol/kg/injection, TIW for 2 weeks+topotecan at 5 mg/kg, BIW for 2 weeks.

Randomized nu/nu mice with IGR-OV1 tumors were (■) untreated; or treated with either: (●) EC145 at 2 μmol/kg/injection, TIW for 2 weeks; or (▲) topotecan at 5 mg/kg, BIW for 2 weeks or (▼) EC145 at 2 μmol/kg/injection, TIW for 2 weeks+topotecan at 5 mg/kg, BIW for 2 weeks. See FIG. 8 for tumor response and FIG. 9 for percentage weight change.

Example

Combination Therapy of EC145 with DOXIL

Figure 42:
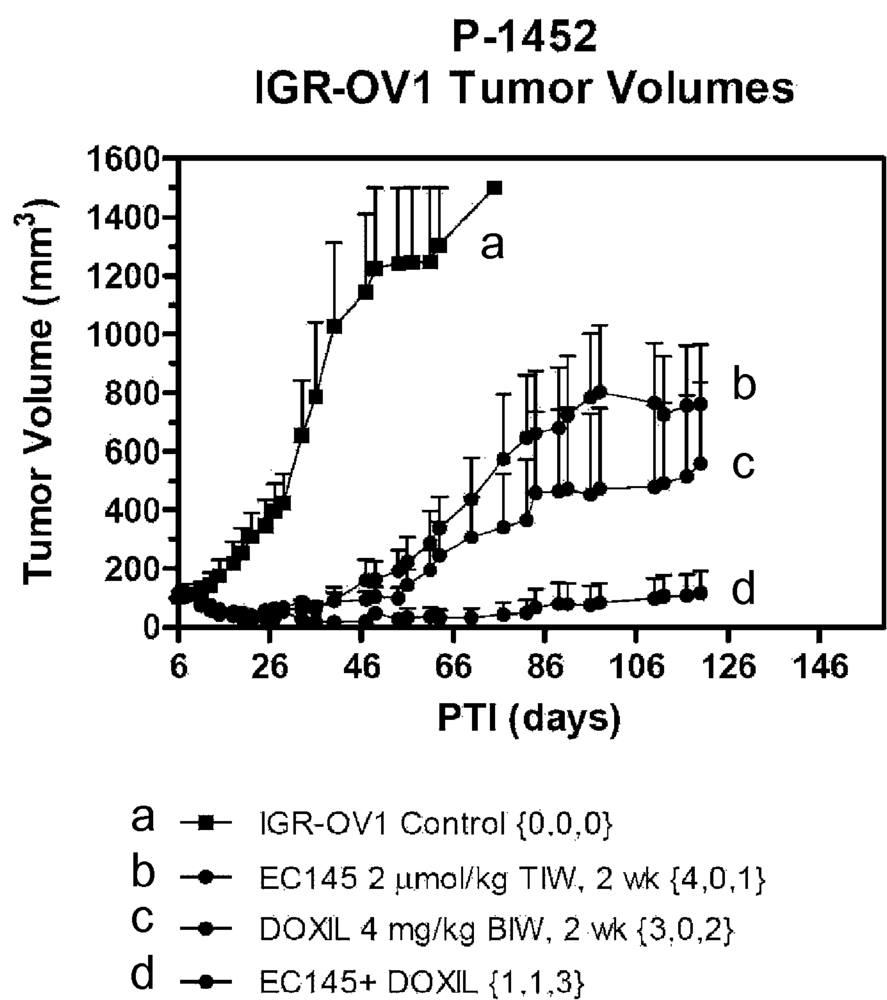
FIG. 42. Tumor volume (average for the five animals in each treatment group) measured for mice with IGR-OV1 tumors that were (a) untreated; or treated with either: (b) EC145 at 2 μmol/kg/injection, TIW for 2 weeks; or (c) DOXIL at 4 mg/kg, BIW for 2 weeks or (d) EC145 at 2 μmol/kg/injection, TIW for 2 weeks+DOXIL at 4 mg/kg, BIW for 2 weeks.
Figure 43:
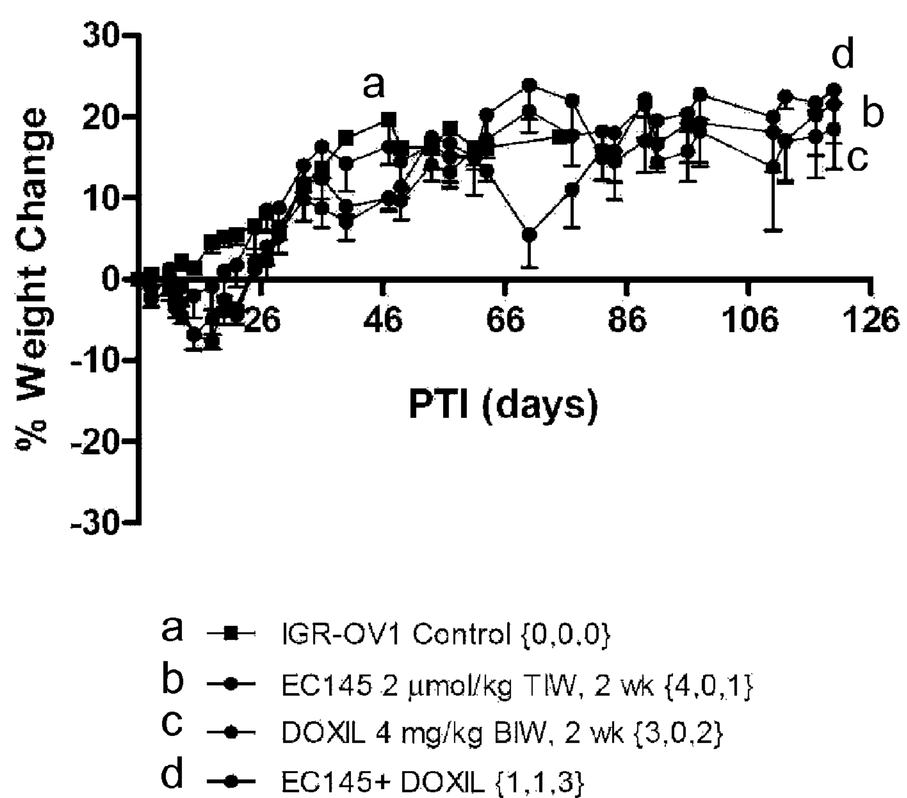
FIG. 43. Percentage weight change (average for the five animals in each treatment group) measured for mice with IGR-OV1 tumors that were (a) untreated; or treated with either: (b) EC145 at 2 μmol/kg/injection, TIW for 2 weeks; or (c) DOXIL at 4 mg/kg, BIW for 2 weeks or (d) EC145 at 2 μmol/kg/injection, TIW for 2 weeks+DOXIL at 4 mg/kg, BIW for 2 weeks.

Randomized nu/nu mice with IGR-OV1 tumors were (a) untreated; or treated with either: (b) EC145 at 2 μmol/kg/injection, TIW for 2 weeks; or (c) DOXIL at 4 mg/kg, BIW for 2 weeks or (d) EC145 at 2 μmol/kg/injection, TIW for 2 weeks+DOXIL at 4 mg/kg, BIW for 2 weeks. See FIG. 42 for tumor response and FIG. 43 for percentage weight change.

Example

Combination Therapy of EC145 with DOXIL

Randomized Balb/c mice with M109 tumors were (a) untreated; or treated with either: (b) EC145 at 1 μmol/kg/injection, TIW for 2 weeks; or (c) DOXIL at 4 mg/kg, BIW for 2 weeks or (d) EC145 at 1 μmol/kg/injection, TIW for 2 weeks+DOXIL at 4 mg/kg, BIW for 2 weeks. Treatment with EC145 alone and Doxil alone each resulted in 3 cures out of 5 animals. The combination treatment resulted in 5 cures out of 5 animals.

Example

Combination Therapy of EC145 with DOXIL

Figure 44:
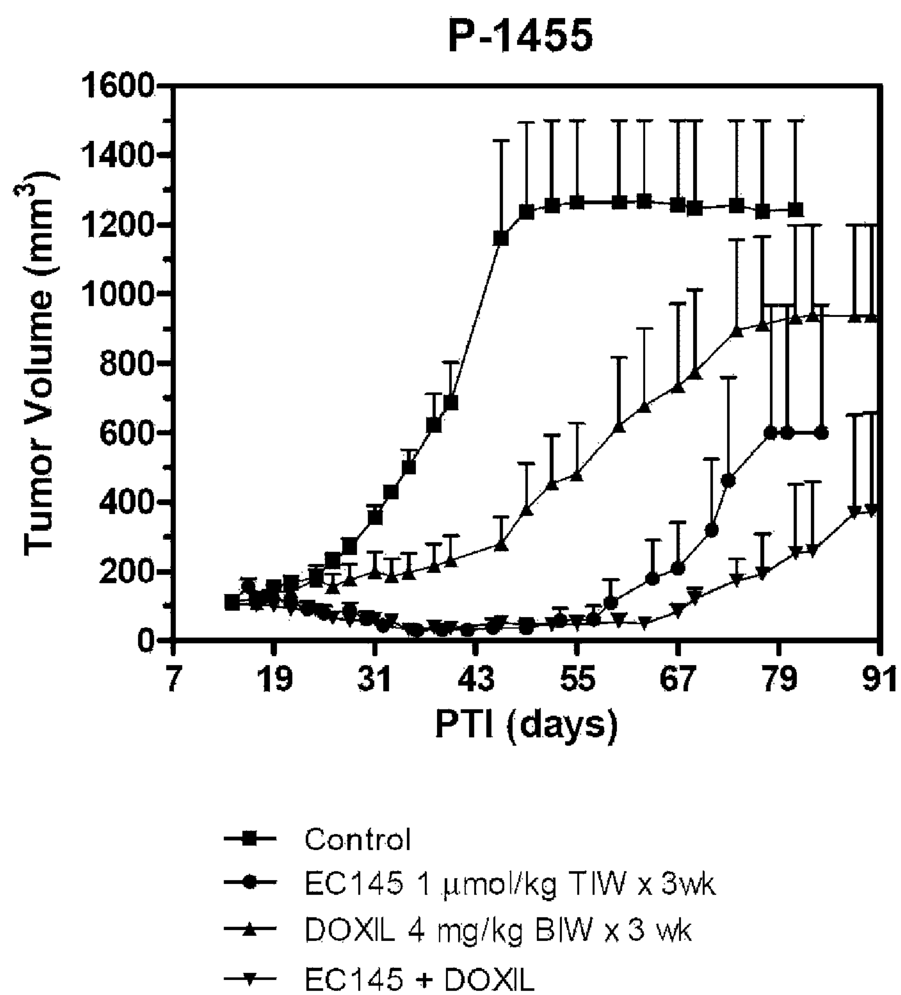
FIG. 44. Tumor volume (average) measured for mu/mu mice with OV90 tumors that were (■) untreated; or treated with either: (●) EC145 at 1 μmol/kg/injection, TIW for 3 weeks; or (▲) DOXIL at 4 mg/kg, BIW for 3 weeks or (▼) EC145 at 1 μmol/kg/injection, TIW for 3 weeks+DOXIL at 4 mg/kg, BIW for 3 weeks.
Figure 45:
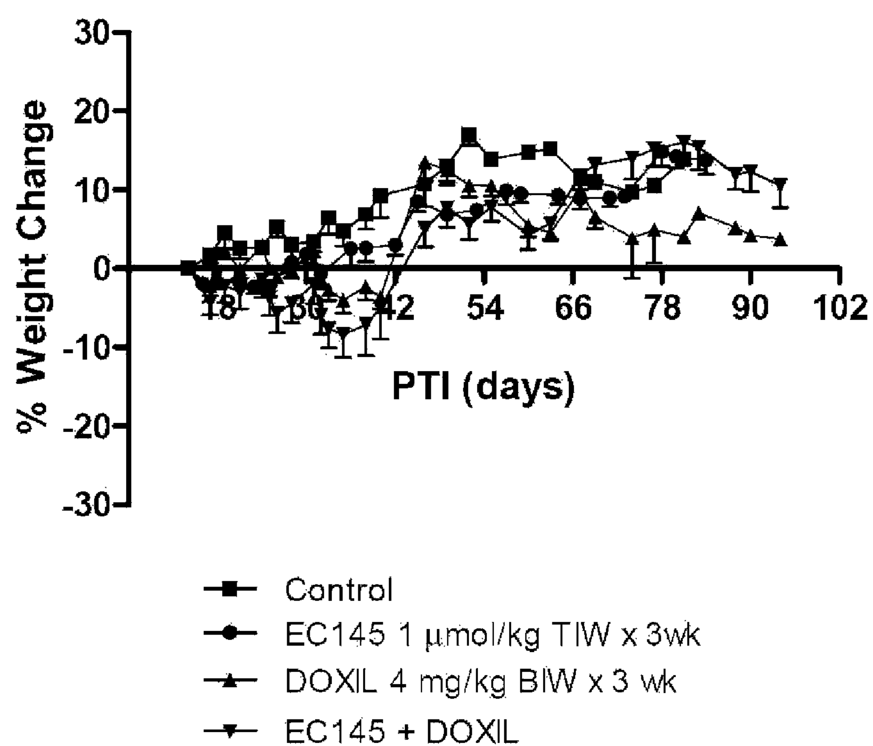
FIG. 45. Percentage weight change (average) measured for mu/mu mice with OV90 tumors that were (■) untreated; or treated with either: (●) EC145 at 1 μmol/kg/injection, TIW for 3 weeks; or (▲) DOXIL at 4 mg/kg, BIW for 3 weeks or (▼) EC145 at 1 μmol/kg/injection, TIW for 3 weeks+DOXIL at 4 mg/kg, BIW for 3 weeks.

Randomized mu/mu mice with OV90 tumors were (■) untreated; or treated with either: (●) EC145 at 1 μmol/kg/injection, TIW for 3 weeks; or (▲) DOXIL at 4 mg/kg, BIW for 3 weeks or (▼) EC145 at 1 μmol/kg/injection, TIW for 3 weeks+DOXIL at 4 mg/kg, BIW for 3 weeks. See FIG. 44 for tumor response and FIG. 45 for percentage weight change.

Example

Combination Therapy of EC145 with DOXIL

Figure 46:
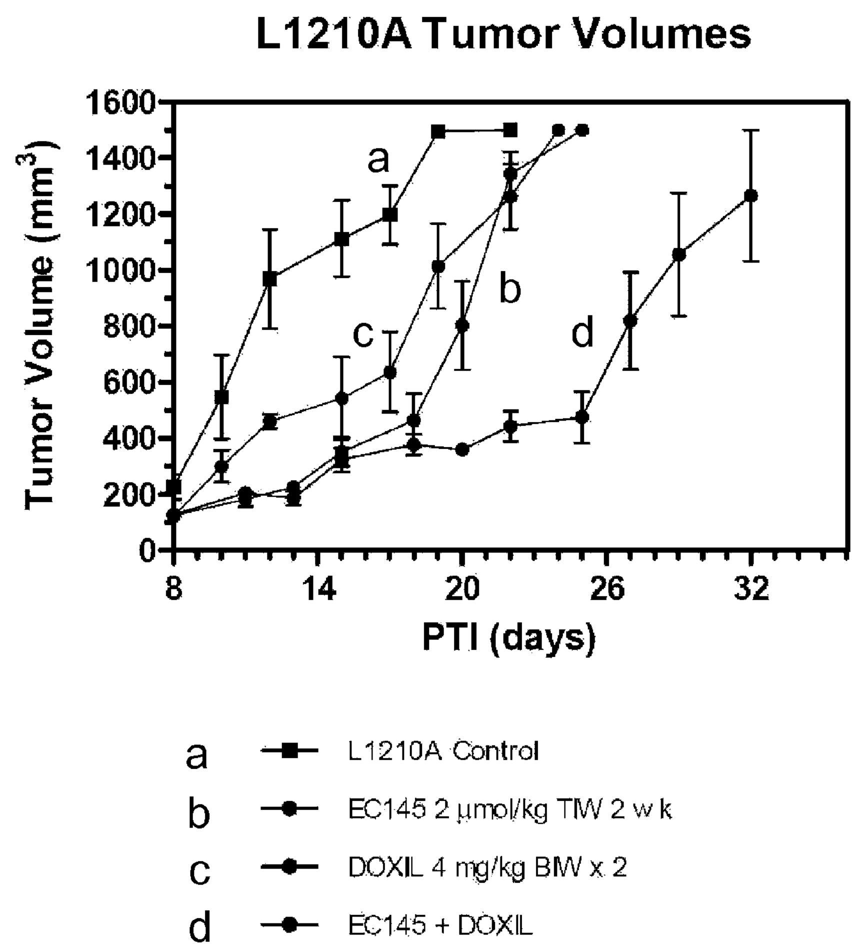
FIG. 46. Tumor volume (average) measured for mice with L1210A tumors (lymphocytic leukemia) that were (a) untreated; or treated with either: (b) EC145 at 2 μmol/kg/injection, TIW for 2 weeks; or (c) DOXIL at 4 mg/kg, BIW for 2 weeks or (d) EC145 at 2 μmol/kg/injection, TIW for 2 weeks+DOXIL at 4 mg/kg, BIW for 2 weeks.
Figure 47:
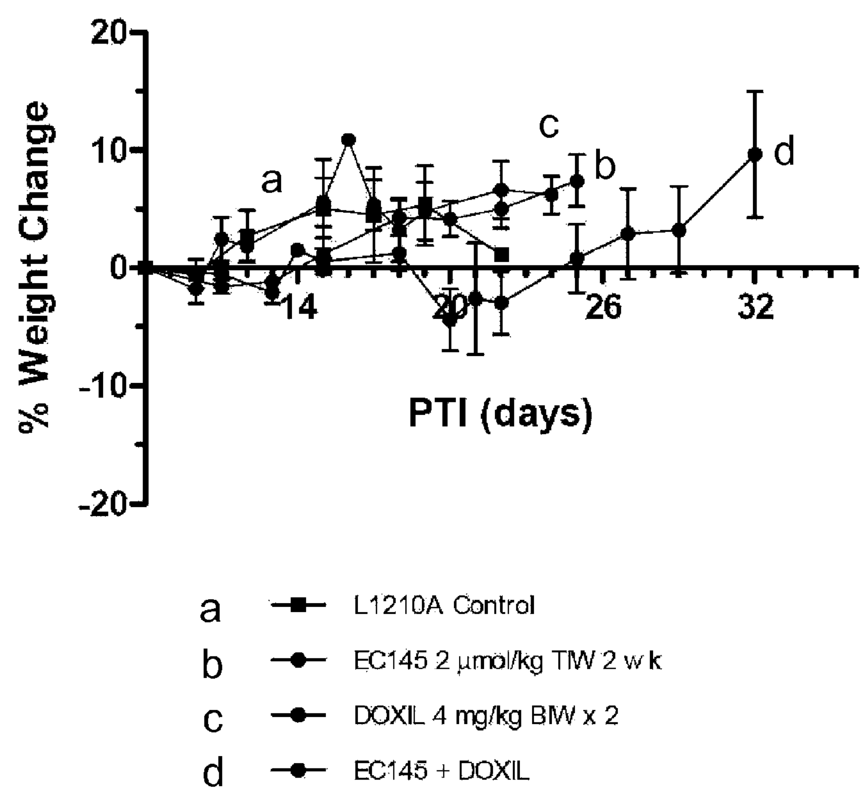
FIG. 47. Percentage weight change (average) measured for mice with L1210A tumors (lymphocytic leukemia) that were (a) untreated; or treated with either: (b) EC145 at 2 μmol/kg/injection, TIW for 2 weeks; or (c) DOXIL at 4 mg/kg, BIW for 2 weeks or (d) EC145 at 2 μmol/kg/injection, TIW for 2 weeks+DOXIL at 4 mg/kg, BIW for 2 weeks.

Randomized DBA mice with L1210A tumors (lymphocytic leukemia) were (a) untreated; or treated with either: (b) EC145 at 2 μmol/kg/injection, TIW for 2 weeks; or (c) DOXIL at 4 mg/kg, BIW for 2 weeks or (d) EC145 at 2 μmol/kg/injection, TIW for 2 weeks+DOXIL at 4 mg/kg, BIW for 2 weeks. See FIG. 46 for tumor response and FIG. 47 for percentage weight change.

Compound Examples

Materials

EC145 API (active drug product) is prepared according the description of U.S. Pat. No. 7,601,332 or of WO 2011/014821 or as described below (PCT/US2011/037134).

Other materials, instruments and equipment are obtained from commercial sources, including the following: Water for injection (WFI); Trisodium Citrate Dihydrate, EMD 1.06432.0500; Citric Acid, J T Baker 0122-01; Mannitol, J T Baker 2553-01; Argon; Nitrogen; Filter, Pall 12122; Tubing; Vials, Wheaton #223685/W008230, 5 mL, 20 mm, Tubing, Type I Glass; Stoppers, (West pharmaceutical #19700021 or 19700022) 20 mm, S-10-F451, 4432/50 Gray w/B2-40 coating (serum stopper); Crimps, Blue (with serum stopper); Stoppers, West 20 mm 4432/50, S-87-J, Gray w/B2-44 coating (split skirt lyophilization stopper); Crimps, Helvoet Pharma 110009704, Brown 6028 (with split skirt lyophilization stopper); Milli-Q water, Millipore Direct Q 3 UV System; Sodium phosphate monobasic monohydrate, Mallinckrodt 7868; Sodium phosphate dibasic dihydrate, Fisher S472-500; Sodium chloride, Mallinckrodt 7581; Potassium chloride, Fisher P330-500; Sodium Citrate Dihydrate, Aldrich 39, 807-1; Sucrose, Sigma S3929-1KG; Sodium Hydroxide, J T Baker 3278-01; Hydrochloric Acid, EMD HX0603P-S; Glacial Acetic Acid, EMD AX0074-6; Triethylamine Acetate, Fisher, 04885-1; 5 N Ammonium Hydroxide, Acros, AC612570010; Acetonitrile, Sigma-Aldrich 34851-4L; HPLC column Waters Symmetry C18, 3.5 μm, 4.6×75 mm, P/N WAT066224; Guard column Waters Symmetry C18, 5 μm, 3.9×20 mm, P/N WAT054225.

Instruments and Equipment

HPLC: Waters Alliance 2695 with Waters 2487 Dual X Absorbance Detector; HPLC: Agilent 1200 with PDA detector; pH meter, pH-08, Corning 340; Autoclave, Hotpack Steam Sterilizer, PE5-004; Oven, VWR 1370FM; Oven, Gruenberg dry heat oven; Balance, Sartorius R3005; Balance, Sartorius CP34001; Pump, Watson Marlow 505S; Pipettor, Eppendorf Repeater Plus, with 50 mL Combitips; Lyophilizer: FTS LyoStar II with LyoManager II Data Collection; Capper, Westcapper NPW-500, 5A-018.

Commonly used abbreviations for e.g., solvents, reagents and protecting groups, are used herein. CDSI is used to denote the carbamoyl disulfide intermediate (4).

HPLC Methods used for fraction and sample evaluation in the examples include the following:

EC145-CMC-IP-0001

Sample preparation: dilute material to approximately 0.5 mg/mL with 8 M guanidine HCl.

Column: Waters XBridge BEH C18, 3.5 μm, 2.1×100 mm.

Mobile Phases: A) 500 mM ammonium bicarbonate, pH 9.2; B) 75:25 acetonitrile-methanol.

Injection volume: 10 μL

UV detection: 280 nm

Column temperature: 50° C.

Sample temperature 5° C.

| | Time (min) | Flow (mL/min) | % A | % B |
|---|---|---|---|---|
| Gradient: | 0.0 | 0.55 | 95 | 5 |
| | 0.5 | 0.55 | 95 | 5 |
| | 1.0 | 0.55 | 80 | 20 |
| | 5.0 | 0.55 | 73.5 | 26.5 |
| | 21.0 | 0.55 | 71.5 | 28.5 |
| | 27.0 | 0.55 | 70 | 30 |
| | 29.0 | 0.55 | 55 | 45 |
| | 30.0 | 0.55 | 30 | 70 |
| | 33.0 | 0.55 | 30 | 70 |
| | 33.1 | 0.75 | 95 | 5 |
| | 40.0 | 0.75 | 95 | 5 |

EC145-CMC-AM-0001 (Version 2.3)

Sample preparation: dilute material to approximately 1 mg/mL with phosphate buffered saline or 1:1 acetonitrile-water (v/v).

Column: Waters Symmetry C18, 3.5 μm, 4.6×75 mm.

Mobile Phases: A) 10 mMtriethylammonium acetate, pH 7.5; B) acetonitrile.

Injection volume: 10 μL

UV detection: 280 nm

Column temperature: 25° C.

Sample temperature 5° C.

| | Time (min) | Flow (mL/min) | % A | % B |
|---|---|---|---|---|
| Gradient: | 0.0 | 1.0 | 85 | 15 |
| | 20.0 | 1.0 | 50 | 50 |
| | 25.0 | 1.0 | 20 | 80 |
| | 30.0 | 1.0 | 20 | 80 |
| | 31.0 | 1.0 | 85 | 15 |
| | 41.0 | 1.0 | 85 | 15 |

Example

Preparation of EC 119

EC119 is synthesized using Fmoc-based solid phase chemistry as follows:

1st Coupling

Add 2-chlorotrityl chloride resin to a peptide synthesis vessel. Swell in DMF (10 mL/g resin). Wash with DMF 2 times (10 mL/g resin). Add 0.8 equivalent of Fmoc-Cys(Trt)-OH in DCM/DMF. Add 2 equivalents of DIPEA. Stir for 30 min. Add methanol (1 mL/g resin) and stir for 10 min. Wash with DMF 3 times. Wash with MTBE 3 times. Wash with DMF 3 times. Add 6% piperazine in 0.1M HOBt in DMF and stir for 10-20 min. Add 6% piperazine in 0.1M HOBt in DMF and stir for 10-20 min. Wash with DMF 3 times. Wash with MTBE 3 times. Perform Kaiser test to confirm completion of the coupling.

2nd Coupling

Wash with DMF 3 times (10 mL/g resin). Add 2 equivalents of Fmoc-Asp(OtBu)-OH in DMF. Add 2 equivalents of HOBt in DMF. Add 2 equivalents of DIC. Stir for 1.5-3 h. Confirm the coupling with Kaiser test. Wash with MTBE 2 times. Wash with DMF 2 times. Add 6% piperazine in 0.1M HOBt in DMF and stir for 10-20 min. Add 6% piperazine in 0.1M HOBt in DMF and stir for 10-20 min. Wash with DMF 3 times. Wash with MTBE 3 times. Perform Kaiser test.

3rd Coupling

Wash with DMF 3 times. Add 2 equivalents of Fmoc-Asp (OtBu)-OH in DMF. Add 2 equivalents of HOBt in DMF. Add 2 equivalents of DIC. Stir for 1.5-3 h. Confirm the coupling with Kaiser test. Wash with MTBE 2 times. Wash with DMF 2 times. Add 6% piperazine in 0.1M HOBt in DMF and stir for 10-20 min. Add 6% piperazine in 0.1M HOBt in DMF and stir for 10-20 min. Wash with DMF 3 times. Wash with MTBE 3 times. Perform Kaiser test.

4th Coupling

Wash with DMF. Add 2 equivalents of Fmoc-Arg(Pbf)-OH in DMF. Add 2 equivalents of HOBt in DMF. Add 2 equivalents of DIC. Stir for 1.5-3 h. Confirm the coupling with Kaiser test. Wash with MTBE 2 times. Wash with DMF 2 times. Add 6% piperazine in 0.1M HOBt in DMF and stir for 10-20 min. Add 6% piperazine in 0.1M HOBt in DMF and stir for 10-20 min. Wash with DMF 3 times. Wash with MTBE 3 times. Perform Kaiser test.

5th Coupling

Wash with DMF 3 times. Add 2 equivalents of Fmoc-Asp (OtBu)-OH in DMF. Add 2 equivalents of HOBt in DMF. Add 2 equivalents of DIC. Stir for 1.5-3 h. Confirm the coupling with Kaiser test. Wash with MTBE 2 times. Wash with DMF 2 times. Add 6% piperazine in 0.1M HOBt in DMF and stir for 10-20 min. Add 6% piperazine in 0.1M HOBt in DMF and stir for 10-20 min. Wash with DMF 3 times. Wash with MTBE 3 times. Perform Kaiser test.

(EC119)

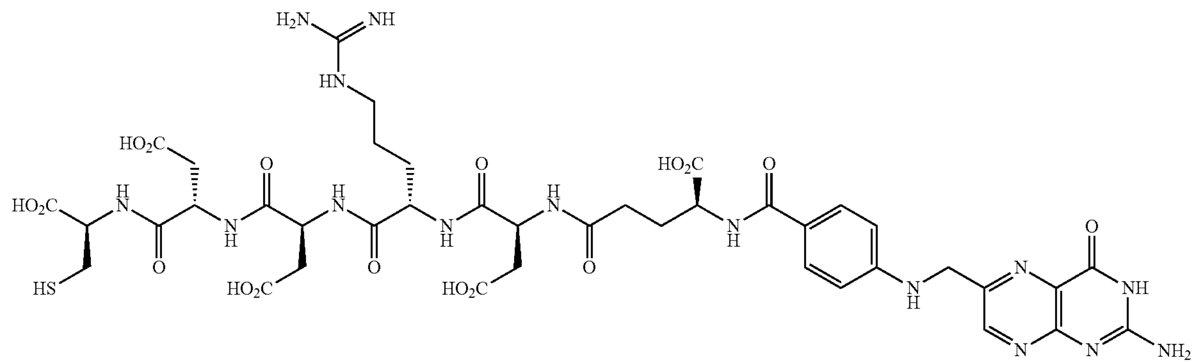

$6^{t1}$ Coupling

Wash with DMF 3 times. Add 2 equivalents of Fmoc-Glu-OtBu in DMF. Add 2 equivalents of HOBt in DMF. Add 2 equivalents of DIC. Confirm the coupling with Kaiser test. Wash with MTBE 2 times. Wash with DMF 2 times. Add 6% piperazine in 0.1M HOBt in DMF and stir for 10-20 min. Add 6% piperazine in 0.1M HOBt in DMF and stir for 10-20 min. Wash with DMF 3 times. Wash with MTBE 3 times. Perform Kaiser test.

$7^{th}$ Coupling

Wash with DMF 3 times. Add 1.2 equivalents of $N^{10}$-TFA-Pte-OH in minimum amount of DMSO. Add 1.2 equivalents of HOBt in DMF. Add 1.2 equivalents of PyBOP in DMF. Add 2.4 equivalents of DIPEA. Stir for 3-5 h. Confirm the coupling with Kaiser test. Wash with DMF 2 times. Wash with MTBE 2 times.

Deprotecting—Removal of Trifluoroacetyl Group

Wash with DMF 2 times. Add 2% hydrazine in DMF and stir for 5 min. Add 2% hydrazine in DMF and stir for 5 min. Add 2% hydrazine in DMF and stir for 5 min. Wash with DMF 3 times. Wash with MTBE 3 times. Dry the resin under vacuum at room temperature.

Cleaving from the Resin

Add cleaving reagent (10 mL/g resin) containing 85% TFA, 2.5% triisopropylsilane, 2.5% water and 10% ethanedithiol to a flask. Cool the mixture in an ice-bath. Add the resin and allow to react for 2-3 hours at room temperature. Filter and collect the filtrate. Add the filtrate to cold MTBE (10 mL of MTBE per 1 mL of filtrate). Stir at 0-5° C. for 30±10 min. Filter the precipitated product through a medium porosity glass filter. Wash the precipitate with cold MTBE 3 times. Dry the product under vacuum at room temperature. Store under nitrogen at −20° C.

Purification

Crude EC 119 is purified by preparative HPLC using a reverse phase C18 column (6-inch column, 2.8 kg, 10 µm, 100 Å). The mobile phases are 0.5% $NH_4OAc$ (A) and 0.5% $NH_4OAc$/ACN (1:4) (B). 40 g of the crude EC119 is dissolved in 1-5% TFA, filtered through a 1 µm glass fiber filter and load on the 6-inch column. Fractions are collected and sampled for HPLC analysis. The pH of each fraction is adjusted to 3-4 immediately after collection using 50% AcOH under nitrogen to precipitate the product. The precipitated product is centrifuged, washed with 0.1% AcOH and stored at 2-8° C. until further processing. The containers are blanked with nitrogen during centrifugation operation to reduce the potential for oxidation. The pool criteria are purity ≥98%, isomers of D-$Arg^4$, D-$Glu^2$ and D-$Asp^3$≤0.25%, other impurity ≤0.5%. The isomers of D-$Asp^5$, D-$Asp^6$ and D-Cys cannot be removed by Prep-HPLC and should be suppressed in the synthesis process. The materials that meet the pool criteria are lyophilized as soon as possible (the EC 119 solution and the wet precipitate are not stable). The purity of the final product is greater than 98%. The overall yield of pure EC119 including solid phase synthesis and purification is approximately 40%. The product is packed in an amber glass bottle under nitrogen and stored at −20° C.

Example

A. Typical Conversion of Vinblastine Sulfate into Desacetylvinblastine Hydrazide

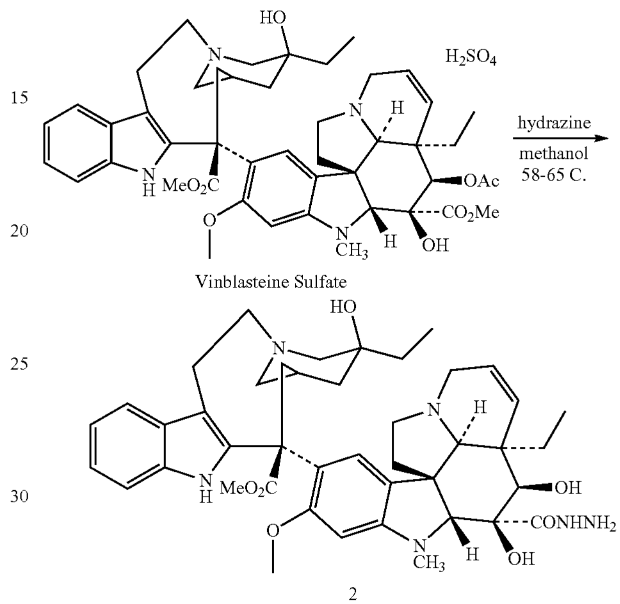

Materials

Vinblastine Sulfate: USP; FW=909.05 g/mole; Methanol: anhydrous; Hydrazine: anhydrous; FW=32 g/mol; De-ionized water; Ethyl acetate: LC/GC grade; Toluene: LC/GC grade; Monobasic sodium phosphate: ≥99.0%; FW=120 g/mole; Dibasic sodium phosphate: ≥99.0%; FW=142 g/mole; Sodium chloride: reagent grade; FW=58.4 g/mole; Sodium sulfate: anhydrous; 5-norbornen-2-carboxylic acid.

Procedure

The reaction, extractive work-up and isolation are run under a nitrogen or argon atmosphere. Pressure filters are used to remove the sodium sulfate and capture the product. The sodium chloride solutions used in the quench and wash are sparged with nitrogen or argon until the dissolved oxygen level is not more than 0.9 ppm.

Vinblastine sulfate and anhydrous methanol are charged to an argon purged reactor. 5-Norbornene-2-carboxylic acid and anhydrous hydrazine are added to the reactor. The mixture is stirred, and after the solids dissolve, heat the mixture to around 60° C. By HPLC analysis, when the reaction is complete, it is cooled, quenched and extracted into ethyl acetate. After drying, the product is crystallized from ethyl acetate and toluene. The solids are dried under vacuum overnight at room temperature.

The buffered NaCl contains: 10.0 g NaCl, 7.10-7.30 g $NaH_2PO_4$, 4.40-4.60 g of $Na_2HPO_4$ and 90 mL of water. The solution is sparged with argon or nitrogen (dissolved oxygen content <0.9 ppm).

A typical isolated yield is 50-60% of the theoretical maximum.

B. Steps 2 and 3 of the EC145 Process
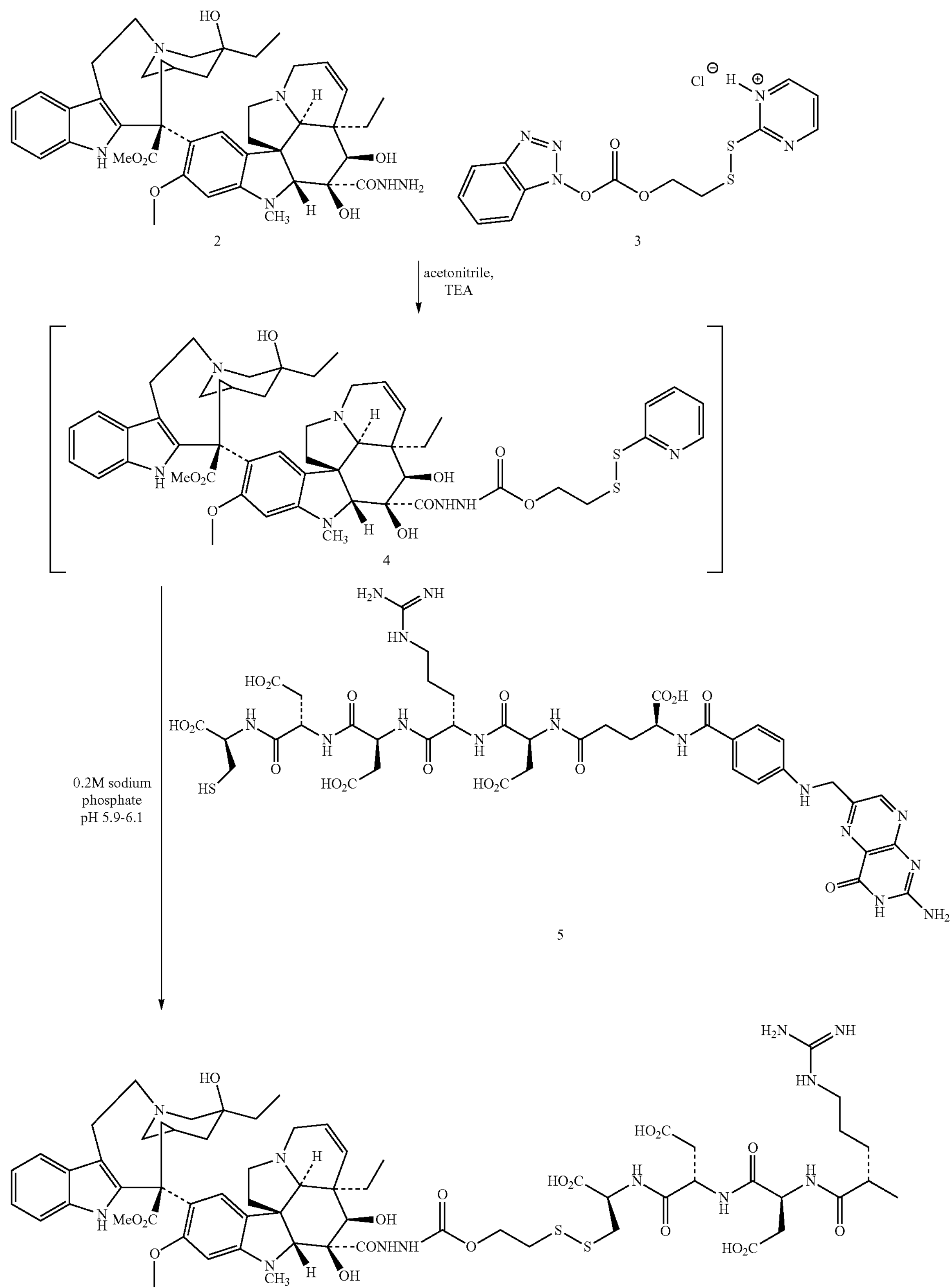

-continued

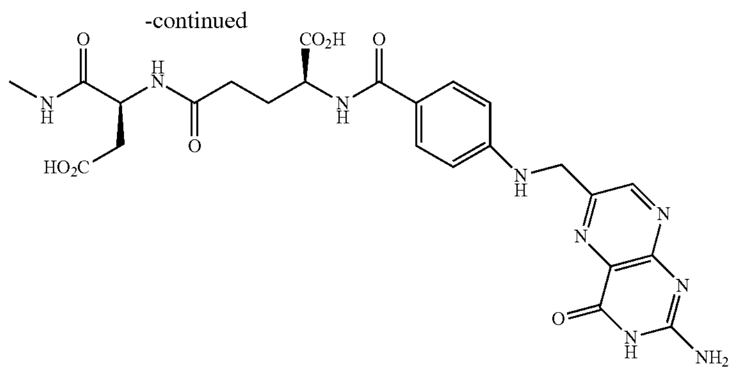

Step 2 and Step 3 Processes

Materials

Desacetylvinblastine hydrazide: FW=768.9 g/mol; 20.5 g, 26.7 mmol; Mixed Carbonate (3): FW=384.9 g/mol; 10.7 g, 27.8 mmol; Acetonitrile: q.s.: Triethylamine: FW=101.2 g/mol; 2.67 g, 26.4 mmol; $Na_2PO_4.7H_2O$: 47.84 g; EC119: 29.9 g 28.6 mmole; 0.5 N HCl: q.s.; WFI: q.s.

Procedure

Note that all of the water used in this process is water for injection (WFI).

Purge an appropriate vessel with argon. Charge 20.5±0.3 g of des-acetyl-vinblastine hydrazide; this charge is potency adjusted, i.e., if the potency were 90.0%, the charge would be 22.8 g. Charge 10.7±0.2 g of Mixed Carbonate (potency adjusted). Charge 800±30 mL of acetonitrile and 2.67±0.11 g of triethylamine. Mix under argon at 10-14° C. for 20-28 hours. Take a sample for HPLC (EC145-CMC-AM-0001, version 2.3). The expected result is the ratio of CDSI to hydrazide ≥25:1. If not, continue mixing under argon at 10-14° C. for 2-4 hours and sample again.

Sparge 780-820 mL of water with argon until the dissolved oxygen level is less than 0.9 ppm; record dissolved oxygen level. Dissolve 47.8±0.5 g of sodium phosphate dibasic heptahydrate in the deoxygenated water. To a suitable container, add 29.8±0.5 g of EC119; (charge is potency adjusted). Add the sodium phosphate solution to the EC119 and mix under argon. Measure the solution's pH and adjust the pH to 5.8-6.2 with 0.5 N HCl if necessary.

Add the buffered EC119 solution to the reaction mixture. Mix under argon at 20-25° C. for 60-75 minutes. Take a sample for HPLC (EC145-CMC-AM-0001, version 2.3). If the ratio of EC145 to CDSI ≥25:1, proceed. If not, continue mixing under argon at 20-25° C. and sample again. If the ratio of EC145 to CDSI ≥25:1, proceed. If not, add an additional 1 g of EC 119 and mix under argon at 20-25° C. for 30 minutes and sample again.

Prepare 6.9 L-7.1 L of 25 mM phosphate buffer, 185-195 mM NaCl, pH 7.2-7.5 made from water sparged with argon until the dissolved oxygen level is less than 0.9 ppm. Dilute the reaction mixture with this buffer. If the mixture develops more than a faint haze, the product solution needs to be filtered (Whatman Polycap TC75 or TC150, 0.45 or 1.0 micron); this filtration may be done while loading the product onto the Biotage column.

Liquid Chromatographic Purification

Use a Biotage 150M, C18 cartridge. This size cartridge can accommodate a reaction mixture twice the size of the one currently described.

Column Preparation:

a. Flush the column with
   i. 12-13 L of acetonitrile
   ii. 12-13 L of 80% acetonitrile and 20% water (v/v)
   iii. 12-13 L of 50% acetonitrile and 50% water (v/v)
   iv. 12-13 L of 10% acetonitrile and 90% water (v/v)

Purification:

Prepare a 25 mM phosphate buffer, (185-195 mmol) NaCl, pH 7.3-7.5

Sparge the buffer with argon until the dissolved oxygen content is ≤0.9 ppm.

Prepare: 41 L of 10% acetonitrile in buffered saline (v/v); 13 L of 16% acetonitrile in buffered saline (v/v), 52 L of 27% acetonitrile in buffered saline (v/v).

Check the dissolved oxygen content of the mobile phase solutions. If the dissolved oxygen content is greater than 0.9 ppm, sparge the mobile phase with argon or nitrogen until the dissolved oxygen level is ≤0.9 ppm.

Flush the column with 26-27 L of the 10% acetonitrile mobile phase.

Load the Product Solution onto the Column

Elute the product using the following sequence of mobile phases:
   i. 13-14 L of the 10% acetonitrile mobile phase.
   ii. 13 L of the 16% acetonitrile mobile phase.
   iii. 51-52 L of the 27% acetonitrile mobile phase.

Notes: An inline uv detector is helpful; Product should come out starting at 15-19 L of the 27% acetonitrile mobile phase with a bandwidth of 8-13 L.

Fraction Evaluation
   i. HPLC Method EC145-CMC-IP-0001
   ii. Passing fraction=≥97.0% EC145 and no impurity ≥0.8%

Post-Run Column Treatment:

The column can be reused once. If the column will be used for a second run, perform ii-iv.
   i. Flush column with 12-13 L of 1:1 acetonitrile-water.
   ii. Flush column with 20-22 L of acetonitrile
   iii. Repeat column preparation steps ii-iv Ultra-Filtration Sparge q.s. water with argon or nitrogen until the dissolved oxygen level is less than 0.9 ppm. Passing chromatography fractions are combined and diluted with an equivalent volume of sparged water. Assemble an ultra-filtration apparatus using a Millipore regenerated cellulose membrane with nominal MW cutoff of 1000 (cat#CDUF002LA) and rinse it with 9 L of deoxygenated water. Start ultra-filtration of the product solution. Maintain a backpressure of 30-50 psi. Continue ultra-filtration until the retentate volume is 2 to 3 L. Add 11 to 12 L of deoxygenated water. Continue ultra-filtration until the retentate volume is 2 to 3 L. Add 11 to 12 L of deoxygenated water. Continue ultra-filtration until the retentate volume is 2 to 3 L. Add 8 to 10 L of deoxygenated water. Continue the ultra-filtration until the retentate volume is 2 L. The ultra-filtration endpoint must be determined by analyzing a sample of the retentate via GC and concentration. The specification is ≤50 micrograms of acetonitrile per milligram of EC145. If not achieved, perform another cycle of the ultra-filtration.

The API solution's concentration must be adjusted so that the packaged material is 6 to 12 mg/mL. At the completion of the ultra-filtration, the apparatus will be rinsed with 1 liter of water. Therefore, continue ultra-filtration or add water as necessary. Once the product solution is out of the ultra-filtration apparatus, rinse the ultra-filtration apparatus with 1 L of deoxygenated water and combine with the product solution.

After the rinse is combined with the product solution, this solution must be filtered through a 0.2 micron absolute filter, and this filtrate is packaged (performed under an inert atmosphere).

A typical yield of isolated product is 50-60% of the theoretical maximum.

Example

Lyophilized EC145

Two vials of an aqueous solution of EC145 with a total volume of 22 mL were thawed at ambient temperature and transferred into four 20 mL lyophilization vials. The vials were transferred to a freezer for approximately 1.5 hours. Lyophilization was conducted using a LABCONCO freeze-drier which was pre-chilled to −72° C. (shelf temperature) before the samples were loaded. Samples were lyophilized for ~30 minutes at −20° C., followed by another 38.5 hours at 20° C. The resulting fluffy pale yellow solid was combined into one vial for further characterization.

Formulations

Aqueous Formulations:

Provided below are formulations which may be used to provide EC145 at a concentration of 1.4 mg/mL of EC145. Single vials are used to provide a 2.5 mg bolus dose of EC145.

Example pH 7.4, Phosphate-Buffered EC145 Formulation

The following formulation provides a EC145 drug product (DP) for intravenous (IV) administration as 2.0 mL of an aqueous sterile liquid formulation, pH 7.4, in single-use clear glass vials with Fluorotech™-coated rubber stoppers, which is stored frozen under inert gas. Each vial contains 1.4 mg/mL of EC145. The quantitative composition of the drug product is shown in the table below. Single vials are used to provide a 2.5 mg bolus dose of EC145. This formulation provides 10 mM phosphate buffer, pH 7.4; 138 mM sodium chloride, and 2.7 mM potassium chloride.

EC145 Drug Product Components

| | Function | Grade | Amount per vial (mg) |
|---|---|---|---|
| EC145 | Active | In-house | 2.8 |
| Sodium phosphate, monobasic monohydrate | pH control tonicity | USP | 1.1 |
| Disodium phosphate, dibasic dihydrate | pH control Tonicity | USP | 2.14 |
| Sodium chloride | Tonicity | USP | 16.12 |
| Potassium chloride | Tonicity | USP | 0.4 |
| Water for Injection | Solvent | WFI | QS to 2.0 mL |

Example pH 6.2 Citrate-Buffered EC145 Formulation

The following formulation provides a solution which is a 50 mM citrate buffered pH 6.2 EC145 solution.

EC145 Drug Product Components

| | Function | Grade | Amount per vial (mg) |
|---|---|---|---|
| EC145 | Active | In-house | 2.8 |
| Trisodium citrate dihydrate | pH control tonicity | USP | 27 |
| Citric acid | pH control Tonicity | USP | 1.5 |
| Water for Injection | Solvent | WFI | QS to 2.0 mL |

Formulations for Lyophilization

Example pH 6.2 Citrate-Buffered EC145 Formulation with 3% Mannitol

The following formulation provides a solution which is a pH 6.2 citrate-buffered EC145 solution containing 3% mannitol as bulking agent useful for lyophilization and reconstitution.

EC145 Drug Product Components

| | Function | Grade | Amount per vial (mg) |
|---|---|---|---|
| EC145 | Active | In-house | 2.8 |
| Trisodium citrate dihydrate | pH control tonicity | USP | 27 |
| Citric acid | pH control Tonicity | USP | 1.5 |
| Mannitol | Bulking agent, Stabilizing Agent Tonicity | USP | 60 |
| Water for Injection | Solvent | WFI | QS to 2.0 mL |

Example pH 6.2 Citrate-Buffered EC145 Formulation with 4% Mannitol/1% Sucrose

The same formulation as for 3% mannitol above, but with 80 mg mannitol and 20 mg sucrose.

Example

Placebo pH 6.2 Citrate-Buffered Formulation with 3% Mannitol

The following formulation provides a placebo solution lacking which is a pH 6.2 citrate-buffered solution containing 3% mannitol as bulking agent useful for lyophilization and reconstitution.

Placebo Product Components

| | Function | Grade | Amount per vial (mg) |
|---|---|---|---|
| Trisodium citrate dihydrate | pH control tonicity | USP | 27 |
| Citric acid | pH control Tonicity | USP | 1.5 |
| Mannitol | Bulking agent, Stabilizing Agent Tonicity | USP | 60 |
| Water for Injection | Solvent | WFI | QS to 2.0 mL |

Example

Preparation of Lyophilized EC145 and Placebo Pharmaceutical Compositions

Lyophilization cycles were run with EC145 vials containing 3% mannitol, EC145 vials containing 4% mannitol/1% sucrose, and placebo vials (without EC145 API). Probes were placed within EC145 solution vials and placebo vials to record the solution temperature during the cycle. Before exposing the final product to air, all of the cycles were back-filled with Argon with the vials stoppered in the lyophilizer. Immediately after stoppering, the vials were crimped and labeled.

In a number of lyophilization runs of varying parameters, no visible differences could be seen between the vials that contained 3% mannitol and the vials that contained 4% mannitol/1% sucrose.

Example

Description of Formulation Process

A large flask is charged with excess WFI and sparged with inert gas for 30 minutes to reduce the oxygen content to <1.0 ppm. An in-process test is used to confirm the oxygen content before formulation is started. A constant, positive pressure inert gas blanket is maintained on the formulation solution throughout the formulation process.

Frozen EC145 drug substance (API) solution is removed from a freezer and thawed in a 20° C.-25° C. controlled temperature circulating water bath. The thawed API solution is added to a tared, inert gas purged vessel to determine the amount of API solution to be formulated. Based on the density and the EC145 concentration in the solution, the weight of solution added to the tared vessel is used to define the total final solution available for filling at 1.4 mg EC145/mL.

A vessel with stir bar is weighed and charged with 62.5% of the total volume of the final fill volume of WFI. Mannitol is added to provide a final concentration of 3% mannitol. Sodium citrate is added to the vessel followed by a rinse with sparged WFI. Citric acid is added to the vessel followed by a rinse with sparged WFI. The sparged solution is mixed until all the citric acid was dissolved.

A pH meter is standardized with pH 4 and 7 buffer standards to measure the pH of the solution. If the pH is not 6.0-6.2, then the pH is adjusted with 1.0M citric acid or 1.0M sodium citrate.

The vessel is wrapped in foil to shield the EC145 from light. The EC145 drug substance solution is added to the formulation vessel with stirring and sparging with inert gas. The drug substance containing vessel is rinsed twice with WFI solution. The mixture is stirred with sparging until a visually homogeneous mixture is obtained. The final target formulation weight is determined and the solution is charged with WFI to the target weight.

The solution is filtered through a 0.22 micron sterile filter, pre-wetted and bubble-point tested, using a peristaltic pump. An inert gas purge of the receiving vessel is maintained throughout the filtration process. Post filtration, the bubble point test is repeated to ensure that effective filtration was maintained throughout the process.

A fill head is calibrated to deliver 2.03 grams (2.0 mL, 2.8 mg EC145) of EC145 formulation solution to each vial. The fill amount is checked routinely during the fill process.

Stoppers are seated half-way on vials through the filling process.

Thermocouples are placed in appropriate vials in lyophilization trays, and the trays are lyophilized as per the cycle defined.

Example

Lyophilization Cycle

The following lyophilization cycle, using the pH 6.2 citrate-buffered EC145 solution containing 3% mannitol described above (2 mL in a 5 mL vial) provides the lyophilized EC145 formulation with a satisfactory cake appearance, which reconstitutes easily in water, and which retains a high API purity (>95%).

Vials are sparged with argon, filled with 2 mL of EC145 formulation, stoppered with a split skirt lyophilization stopper in the half seated position. As soon as a tray is filled and stoppered, it is placed in the lyophilizer at 5° C.

1. Pre-cool lyophilizer shelves to 5° C.
2. Load filled trays onto pre-cooled shelves.
3. Initiate lyophilization cycle after loading is complete.
4. Hold shelf temperature at 5° C. for 30-60 minutes Alternatively, pre-cooling the shelves to −50° C. to 5° C. allows reduced time to precool the filled trays; and step 4 may not be needed.

5. Immediately ramp the shelf temperature to −50° C.
6. Hold the shelf temperature at −50° C. for 60 to 360 minutes.
7. Reduce the chamber pressure to 50 to 150 mTorr.
8. Hold the shelf temperature at −50° C. for 180 to 1740 minutes.
9. Ramp the shelf temperature to −37° C. over 73 minutes (0.20° C./minute).
10. Hold the shelf temperature at −37° C. for 60 to 720 minutes.
11. Ramp the shelf temperature to −20° C. over 150 minutes (0.11° C./minute).
12. Hold the shelf temperature at −20° C. for 60 to 360 minutes.
13. Ramp the shelf temperature to 20° C. to 30° C. over 60 to 360 minutes.
14. Hold the shelf temperature at 20° C. to 30° C. for 60 to 600 minutes.
15. Backfill the chamber with argon or nitrogen to 12.5 psia (870 mbar).

16. Collapse the shelves (fully stopper vials).
17. Backfill to atmospheric pressure with filtered air.
18. Unload lyophilizer.

A particular example of the above lyophilization cycle, with the initial cooling for 30 minutes at 5° C., may be represented in summary form as follows:

| | Initial Freezing | | |
|---|---|---|---|
| | 1 | 2 | 3 |
| Temp (° C.) | 5 | −50 | −50 |
| Time (min) | 30 | 0 | 360 |

| | Primary and Secondary Drying | | | | | | |
|---|---|---|---|---|---|---|---|
| | 1 | 2 | 3 | 4 | 5 | 6 | 7 |
| Temp (° C.) | −50 | −37 | −37 | −20 | −20 | 20 | 20 |
| Time (min) | 1740 | 73 | 720 | 150 | 360 | 360 | 600 |
| Vacuum (mTorr) | 100 | 100 | 100 | 100 | 100 | 100 | 100 |

The vials are then capped to provide the final product as a satisfactory cake in each vial.

While certain embodiments of the present invention have been described and/or exemplified above, it is contemplated that considerable variation and modification thereof are possible. Accordingly, the present invention is not limited to the particular embodiments described and/or exemplified herein.

What is claimed is:

1. A method of treatment of a folate receptor expressing cancer, the method comprising the steps of administering EC145 to a patient; and administering to the patient one or more additional chemotherapeutic agents having a mode of action selected from the group consisting of angiogenesis inhibition, microtubule assembly inhibition, DNA cross-linking, topoisomerase inhibition, DNA intercalation, DNA synthesis inhibition, and tyrosine kinase inhibition, wherein the EC145 and the additional chemotherapeutic agent are in sterile containers or packages.

2. The method of claim 1 wherein the additional chemotherapeutic agent is selected from the group consisting of cisplatin, carboplatin, topotecan, irinotecan, bevacizumab, erlotinib, lapatinib, and pemetrexed.

3. The method of claim 2 wherein the additional chemotherapeutic agent is selected from the group consisting of carboplatin and bevacizumab.

4. The method of claim 3 wherein the additional chemotherapeutic agent is carboplatin.

5. The method of claim 3 wherein the additional chemotherapeutic agent is bevacizumab.

6. The method of claim 1 wherein the cancer is an epithelial cancer.

7. The method of claim 6 wherein the epithelial cancer is an ovarian, an endometrial, or a non-small cell lung cancer.

8. The method of claim 7 wherein the epithelial cancer is an ovarian cancer.

9. The method of claim 7 wherein the epithelial cancer is a non-small cell lung cancer.

10. The method of claim 1 wherein the additional chemotherapeutic agent is administered at a dose that is 50 to 80% of the maximum tolerated dose for the chemotherapeutic agent.

11. The method of claim 1 wherein the EC145 and the chemotherapeutic agent are administered in therapeutically effective amounts.

12. The method of claim 11 wherein the effective amounts range from about 1 μg/m2 to about 500 mg/m2 of body surface area.

13. The method of claim 11 wherein the effective amounts range from about 1 μg/m2 to about 300 mg/m2 of body surface area.

14. The method of claim 11 wherein the effective amounts range from about 10 μg/kg to about 100 μg/kg of patient body weight.

15. The method of claim 1 wherein the cancer is a platinum-resistant ovarian cancer.

16. The method of claim 1 wherein the EC145 and the additional chemotherapeutic agent have a purity of at least 90% based on weight percentage.

17. The method of claim 1 wherein the EC145 is in the form of a reconstitutable lyophilizate.

18. The method of claim 1 wherein the EC145 and the additional chemotherapeutic agent are in sterile, pyrogen-free aqueous solutions.

19. The method of claim 1 wherein the EC145 and the additional chemotherapeutic agent are administered at doses lower than their maximum tolerable doses.

20. A kit comprising EC145 and one or more additional chemotherapeutic agents having a mode of action selected from the group consisting of angiogenesis inhibition, microtubule assembly inhibition, DNA cross-linking, topoisomerase inhibition, DNA intercalation, DNA synthesis inhibition, and tyrosine kinase inhibition, wherein the EC145 and the one or more chemotherapeutic agents are in therapeutically effective amounts for the treatment of a folate receptor expressing cancer.

21. The kit of claim 20 wherein the additional chemotherapeutic agent is selected from the group consisting of cisplatin, carboplatin, topotecan, irinotecan, bevacizumab, erlotinib, lapatinib, and pemetrexed.

22. The kit of claim 21 wherein the additional chemotherapeutic agent is selected from the group consisting of carboplatin and bevacizumab.

23. The kit of claim 22 wherein the additional chemotherapeutic agent is carboplatin.

24. The kit of claim 22 wherein the additional chemotherapeutic agent is bevacizumab.

25. The kit of claim 20 wherein the EC145 and the additional chemotherapeutic agent are in sterile containers or packages.

26. The kit of claim 20 wherein the EC145 and the additional chemotherapeutic agent have a purity of at least 90% based on weight percentage.

27. The kit of claim 20 wherein the EC145 and the additional chemotherapeutic agent have a purity of at least 95% based on weight percentage.

28. The kit of claim 20 wherein the EC145 is in the form of a reconstitutable lyophilizate.

29. The kit of claim 20 wherein the EC145 and the additional chemotherapeutic agent are in sterile, pyrogen-free aqueous solutions.

* * * * *